United States Patent
Frank et al.

(10) Patent No.: US 11,104,874 B2
(45) Date of Patent: Aug. 31, 2021

(54) COATING A BIOREACTOR

(71) Applicant: Terumo BCT, Inc., Lakewood, CO (US)

(72) Inventors: Nathan D. Frank, Arvada, CO (US); Brian J. Nankervis, Golden, CO (US); Dennis J. Hlavinka, Arvada, CO (US); Thomas G. Dilorenzo, Arvada, CO (US)

(73) Assignee: Terumo BCT, Inc., Lakewood, CO (US)

( * ) Notice: Subject to any disclaimer, the term of this patent is extended or adjusted under 35 U.S.C. 154(b) by 0 days.

(21) Appl. No.: 15/616,876

(22) Filed: Jun. 7, 2017

(65) Prior Publication Data

US 2017/0349873 A1    Dec. 7, 2017

Related U.S. Application Data

(60) Provisional application No. 62/347,012, filed on Jun. 7, 2016, provisional application No. 62/347,025, filed on Jun. 7, 2016.

(51) Int. Cl.
    *C12M 1/00*    (2006.01)
    *C12M 1/36*    (2006.01)
    (Continued)

(52) U.S. Cl.
    CPC .............. *C12M 23/20* (2013.01); *B05D 7/22* (2013.01); *C12M 23/50* (2013.01); *C12M 25/10* (2013.01);
    (Continued)

(58) Field of Classification Search
    CPC ...... C12M 23/20; C12M 25/10; C12M 41/48; C12M 29/16; C12M 41/00; C12M 23/50;
    (Continued)

(56) References Cited

U.S. PATENT DOCUMENTS 3,821,087 A    6/1974   Knazek et al.
3,896,061 A    7/1975   Tanzawa et al.
               (Continued)

FOREIGN PATENT DOCUMENTS

CN    102406926 A    4/2012
DE    3833925 A1     9/1989
               (Continued)

OTHER PUBLICATIONS

Gloeckner, H.; Lemke, H.-D. New Miniaturized Hollow-Fiber Bioreactor for in Vivo Like Cell Culture, Cell Expansion, and Production of Cell-Derived Products. Biotechnology Progress 2001, 17 (5), 828-831. (Year: 2001).*

(Continued)

*Primary Examiner* — William P Fletcher, III
(74) *Attorney, Agent, or Firm* — Terumo BCT, Inc. IP Law Department

(57) ABSTRACT

Embodiments provide for introducing a first fluid into a bioreactor and while introducing the first fluid into the bioreactor, circulating a second fluid with a reagent at a first flow rate through the bioreactor. The bioreactor may be maintained in a first orientation for a first period of time to allow at least a first portion of the reagent to coat the bioreactor. The second fluid may then be circulated at a second flow rate slower than the first flow rate to allow a second portion of the reagent to coat the bioreactor. Introduction of the first fluid may promote coating of the bioreactor by ultrafiltration. The introduction of the first fluid may be stopped. A third fluid may be circulated through the bioreactor to remove a portion of the reagent not coated on the bioreactor.

19 Claims, 34 Drawing Sheets

(51) Int. Cl.
*C12M 1/34* (2006.01)
*C12Q 3/00* (2006.01)
*C12N 5/0775* (2010.01)
*C12M 1/12* (2006.01)
*B05D 7/22* (2006.01)
*C12M 3/04* (2006.01)

(52) U.S. Cl.
CPC ............ *C12M 25/12* (2013.01); *C12M 27/10* (2013.01); *C12M 29/10* (2013.01); *C12M 29/16* (2013.01); *C12M 29/18* (2013.01); *C12M 41/00* (2013.01); *C12M 41/48* (2013.01); *C12N 5/0662* (2013.01); *C12N 5/0663* (2013.01); *C12Q 3/00* (2013.01); *B05D 2254/00* (2013.01); *B05D 2259/00* (2013.01)

(58) Field of Classification Search
CPC ...... C12M 29/18; C12M 27/10; C12M 29/10; C12M 25/12; C12N 5/0662; C12N 5/0663; C12Q 3/00; B05D 7/22; B05D 2259/00; B05D 2254/00
USPC .................................................. 427/230–239
See application file for complete search history.

(56) References Cited

U.S. PATENT DOCUMENTS

| | | | |
|---|---|---|---|
| 4,391,912 A | 7/1983 | Yoshida et al. | |
| 4,439,322 A | 3/1984 | Sonoda et al. | |
| 4,618,586 A | 10/1986 | Walker et al. | |
| 4,629,686 A | 12/1986 | Gruenberg | |
| 4,647,539 A | 3/1987 | Bach | |
| 4,650,766 A | 3/1987 | Harm et al. | |
| 4,705,918 A | 11/1987 | Harmon | |
| 4,722,902 A | 2/1988 | Harm et al. | |
| 4,804,628 A | 2/1989 | Cracauer et al. | |
| 4,885,087 A | 12/1989 | Kopf | |
| 4,889,812 A | 12/1989 | Guinn et al. | |
| 4,894,342 A | 1/1990 | Guinn et al. | |
| 4,918,019 A | 4/1990 | Guinn | |
| 4,940,541 A | 7/1990 | Aoyagi | |
| 4,973,558 A | 11/1990 | Wilson et al. | |
| 5,064,764 A * | 11/1991 | Besnainon | C12M 23/26 210/321.8 |
| 5,079,168 A | 1/1992 | Amiot | |
| 5,126,238 A | 6/1992 | Gebhard et al. | |
| 5,162,225 A | 11/1992 | Sager et al. | |
| 5,202,254 A | 4/1993 | Amiot | |
| 5,330,915 A | 7/1994 | Wilson et al. | |
| 5,399,493 A | 3/1995 | Emerson et al. | |
| 5,416,022 A | 5/1995 | Amiot | |
| 5,437,994 A | 8/1995 | Emerson et al. | |
| 5,459,069 A | 10/1995 | Palsson et al. | |
| 5,510,257 A | 4/1996 | Sirkar et al. | |
| 5,541,105 A | 7/1996 | Melink et al. | |
| 5,605,822 A | 2/1997 | Emerson et al. | |
| 5,622,857 A | 4/1997 | Goffe | |
| 5,631,006 A | 5/1997 | Melink et al. | |
| 5,635,386 A | 6/1997 | Palsson et al. | |
| 5,635,387 A | 6/1997 | Fei et al. | |
| 5,643,794 A | 7/1997 | Liu et al. | |
| 5,646,043 A | 7/1997 | Emerson et al. | |
| 5,656,421 A | 8/1997 | Gebhard et al. | |
| 5,670,147 A | 9/1997 | Emerson et al. | |
| 5,670,351 A | 9/1997 | Emerson et al. | |
| 5,688,687 A | 11/1997 | Palsson et al. | |
| 5,763,194 A | 6/1998 | Slowiaczek et al. | |
| 5,763,261 A | 6/1998 | Gruenberg | |
| 5,763,266 A | 6/1998 | Palsson et al. | |
| 5,882,918 A | 3/1999 | Goffe | |
| 5,888,807 A | 3/1999 | Palsson et al. | |
| 5,955,353 A * | 9/1999 | Amiot | C12M 25/10 210/321.81 |
| 5,958,763 A | 9/1999 | Goffe | |
| 5,981,211 A | 11/1999 | Hu et al. | |
| 5,985,653 A | 11/1999 | Armstrong et al. | |
| 5,994,129 A | 11/1999 | Armstrong et al. | |
| 5,998,184 A | 12/1999 | Shi | |
| 6,001,585 A | 12/1999 | Gramer | |
| 6,048,721 A | 4/2000 | Armstrong et al. | |
| 6,096,532 A | 8/2000 | Armstrong et al. | |
| 6,197,575 B1 | 3/2001 | Griffith et al. | |
| 6,228,635 B1 | 5/2001 | Armstrong et al. | |
| 6,238,908 B1 | 5/2001 | Armstrong et al. | |
| 6,326,198 B1 | 12/2001 | Emerson et al. | |
| 6,372,495 B1 | 1/2002 | Flendrig | |
| 6,566,126 B2 | 5/2003 | Cadwell | |
| 6,582,955 B2 | 6/2003 | Martinez et al. | |
| 6,616,912 B2 | 9/2003 | Eddleman et al. | |
| 6,642,019 B1 | 11/2003 | Anderson et al. | |
| 6,667,034 B2 | 12/2003 | Palsson et al. | |
| 6,680,166 B1 | 1/2004 | Mullon et al. | |
| 6,835,566 B2 | 12/2004 | Smith et al. | |
| 6,844,187 B1 | 1/2005 | Weschler et al. | |
| 6,943,008 B1 | 9/2005 | Ma | |
| 6,969,308 B2 | 11/2005 | Doi et al. | |
| 6,979,308 B1 | 12/2005 | McDonald et al. | |
| 7,033,823 B2 | 4/2006 | Chang | |
| 7,041,493 B2 | 5/2006 | Rao | |
| 7,112,441 B2 | 9/2006 | Uemura et al. | |
| 7,172,696 B1 | 2/2007 | Martinez et al. | |
| 7,270,996 B2 | 9/2007 | Cannon et al. | |
| 7,531,351 B2 | 5/2009 | Marx et al. | |
| 7,534,601 B2 * | 5/2009 | Wikswo | B01L 3/502746 435/289.1 |
| 7,682,822 B2 | 3/2010 | Noll et al. | |
| 7,718,430 B2 | 5/2010 | Antwiler | |
| 8,288,159 B2 | 10/2012 | Warren et al. | |
| 8,298,823 B2 | 10/2012 | Warren et al. | |
| 8,309,347 B2 | 11/2012 | Antwiler | |
| 8,383,397 B2 | 2/2013 | Wojciechowski et al. | |
| 8,399,245 B2 | 3/2013 | Leuthaeuser et al. | |
| 8,540,499 B2 | 9/2013 | Page et al. | |
| 8,785,181 B2 | 7/2014 | Antwiler | |
| 8,895,291 B2 | 11/2014 | DiLorenzo et al. | |
| 9,057,045 B2 | 6/2015 | Gibbons et al. | |
| 9,109,193 B2 | 8/2015 | Galliher et al. | |
| 9,175,259 B2 | 11/2015 | Nankervis | |
| 9,441,195 B2 | 9/2016 | Wojciechowski et al. | |
| 9,534,198 B2 | 1/2017 | Page et al. | |
| 9,732,313 B2 | 8/2017 | Hirschel et al. | |
| 10,093,956 B2 * | 10/2018 | Hirschel | C07K 16/065 |
| 10,494,421 B2 | 12/2019 | Castillo | |
| 10,577,575 B2 | 3/2020 | Frank | |
| 2004/0027914 A1 | 2/2004 | Vrane | |
| 2006/0019388 A1 | 1/2006 | Hutmacher et al. | |
| 2006/0166364 A1 | 7/2006 | Senesac | |
| 2006/0233834 A1 | 10/2006 | Guehenneux et al. | |
| 2007/0122904 A1 | 5/2007 | Nordon | |
| 2007/0160583 A1 | 7/2007 | Lange et al. | |
| 2007/0231305 A1 | 10/2007 | Noll et al. | |
| 2007/0238169 A1 | 10/2007 | Abilez et al. | |
| 2007/0298497 A1 | 12/2007 | Antwiler | |
| 2008/0050770 A1 | 2/2008 | Zhang et al. | |
| 2008/0220522 A1 | 9/2008 | Antwiler | |
| 2008/0220523 A1 * | 9/2008 | Antwiler | C12M 25/10 435/394 |
| 2008/0227190 A1 | 9/2008 | Antwiler | |
| 2008/0248572 A1 | 10/2008 | Antwiler | |
| 2008/0254533 A1 | 10/2008 | Antwiler | |
| 2009/0215022 A1 | 8/2009 | Page et al. | |
| 2009/0269841 A1 | 10/2009 | Wojciechowski et al. | |
| 2010/0042260 A1 | 2/2010 | Antwiler | |
| 2010/0105138 A1 | 4/2010 | Dodd et al. | |
| 2010/0120136 A1 * | 5/2010 | Larsen | C12M 27/10 435/297.1 |
| 2010/0144037 A1 | 6/2010 | Antwiler | |
| 2011/0159584 A1 | 6/2011 | Gibbons et al. | |
| 2011/0212493 A1 | 9/2011 | Hirschel et al. | |
| 2012/0086657 A1 * | 4/2012 | Stanton, IV | C12M 23/42 345/173 |
| 2012/0315696 A1 | 12/2012 | Luitjens et al. | |
| 2013/0058907 A1 | 3/2013 | Wojciechowski et al. | |

(56) References Cited

U.S. PATENT DOCUMENTS

| | | | |
|---|---|---|---|
| 2013/0143313 A1 | 6/2013 | Niazi | |
| 2014/0051162 A1* | 2/2014 | Nankervis | C12N 5/00 |
| | | | 435/366 |
| 2014/0051167 A1 | 2/2014 | Nankervis et al. | |
| 2015/0111252 A1 | 4/2015 | Hirschel et al. | |
| 2015/0140653 A1 | 5/2015 | Jones et al. | |
| 2015/0175950 A1 | 6/2015 | Hirschel et al. | |
| 2015/0225685 A1 | 8/2015 | Hirschel et al. | |
| 2015/0259749 A1 | 9/2015 | Santos et al. | |
| 2015/0275170 A1* | 10/2015 | Nankervis | C12M 41/48 |
| | | | 435/325 |
| 2016/0090569 A1 | 3/2016 | Vang | |
| 2016/0362650 A1 | 12/2016 | Wojciechowski et al. | |
| 2016/0362652 A1 | 12/2016 | Page et al. | |
| 2017/0349869 A1 | 12/2017 | Frank et al. | |
| 2017/0349872 A1 | 12/2017 | Frank | |
| 2018/0010082 A1 | 1/2018 | Jaques et al. | |
| 2018/0030398 A1 | 2/2018 | Castillo | |
| 2018/0155668 A1 | 6/2018 | Hirschel et al. | |
| 2019/0194628 A1 | 6/2019 | Rao et al. | |

FOREIGN PATENT DOCUMENTS

| | | |
|---|---|---|
| EP | 0220650 A2 | 5/1987 |
| EP | 1538196 A1 | 6/2005 |
| EP | 2027247 B1 | 1/2011 |
| EP | 2481819 A1 | 8/2012 |
| JP | H02245177 A | 9/1990 |
| JP | 2003510068 A | 3/2003 |
| JP | 2005278564 A * | 10/2005 |
| JP | 2005278564 A | 10/2005 |
| JP | 2006223273 A | 8/2006 |
| JP | 2007000038 A | 1/2007 |
| JP | 2012506257 A | 3/2012 |
| JP | 5548207 B2 | 7/2014 |
| JP | 2019516029 A | 6/2019 |
| JP | 2019525765 A | 9/2019 |
| KR | 101228026 B1 | 1/2013 |
| KR | 20150002762 A | 1/2015 |
| KR | 101504392 B1 | 3/2015 |
| KR | 101548790 B1 | 8/2015 |
| KR | 101553040 B1 | 9/2015 |
| KR | 20170076679 A | 7/2017 |
| KR | 20180027501 A | 3/2018 |
| KR | 102027596 B1 | 10/2019 |
| KR | 20200034790 A | 3/2020 |
| KR | 20200058433 A | 5/2020 |
| WO | 86/02379 A1 | 4/1986 |
| WO | 88/01643 A1 | 3/1988 |
| WO | 89/12676 A1 | 12/1989 |
| WO | 90/02171 A1 | 3/1990 |
| WO | 91/07485 A1 | 5/1991 |
| WO | 92/10564 A1 | 6/1992 |
| WO | 95/04813 A1 | 2/1995 |
| WO | 95/21911 A1 | 8/1995 |
| WO | 95/24468 A1 | 9/1995 |
| WO | 97/16527 A1 | 5/1997 |
| WO | 98/22588 A2 | 5/1998 |
| WO | 98/53046 A1 | 11/1998 |
| WO | 00/46354 A1 | 8/2000 |
| WO | 00/75275 A2 | 12/2000 |
| WO | 01/23520 A1 | 4/2001 |
| WO | 02/28996 A1 | 4/2002 |
| WO | 03/039459 A2 | 5/2003 |
| WO | 03/105663 A2 | 12/2003 |
| WO | 2004024303 A2 | 3/2004 |
| WO | 2004/090112 A2 | 10/2004 |
| WO | 2005087915 A2 | 9/2005 |
| WO | 2005/104755 A2 | 11/2005 |
| WO | 2006/037022 A2 | 4/2006 |
| WO | 2007/038572 A2 | 4/2007 |
| WO | 2007/059473 A2 | 5/2007 |
| WO | 2007/117765 A2 | 10/2007 |
| WO | 2007/136821 A1 | 11/2007 |
| WO | 2007/139742 A1 | 12/2007 |
| WO | 2007/139746 A1 | 12/2007 |
| WO | 2007/139747 A1 | 12/2007 |
| WO | 2007/139748 A2 | 12/2007 |
| WO | 2008/073635 A2 | 6/2008 |
| WO | 2008/109674 A2 | 9/2008 |
| WO | 2009/034186 A2 | 3/2009 |
| WO | 2010/036760 A1 | 4/2010 |
| WO | 2011/098592 A1 | 8/2011 |
| WO | 2011/130617 A2 | 10/2011 |
| WO | 2012/171026 A2 | 12/2012 |
| WO | 2012/171030 A2 | 12/2012 |
| WO | 2013/085682 A1 | 6/2013 |
| WO | 2015/059714 A1 | 4/2015 |
| WO | 2015/069943 A1 | 5/2015 |
| WO | 2015/073913 A1 | 5/2015 |
| WO | 2015/118148 A1 | 8/2015 |
| WO | 2015/118149 A1 | 8/2015 |
| WO | 2016/130940 A1 | 8/2016 |
| WO | 2017/072201 A2 | 5/2017 |
| WO | 2017/158611 A1 | 9/2017 |
| WO | 2017/207822 A1 | 12/2017 |
| WO | 2018/183426 A1 | 10/2018 |
| WO | 2019/155032 A1 | 8/2019 |
| WO | 2019/238919 A1 | 12/2019 |
| WO | 2020/020569 A1 | 1/2020 |
| WO | 2020/079274 A1 | 4/2020 |

OTHER PUBLICATIONS

U.S. Appl. No. 15/616,745, U.S. 2017/0349872 (now U.S. Pat. No. 10,577,575).

U.S. Appl. No. 15/616,635, U.S. 2017/0349869.

U.S. Appl. No. 16/845,686.

Biovest International, "AutovaxIDTM: advanced hollow fibre bioreactors with automated lactate control yield higher density monoclonal antibody production", VWRbioMarke, No. 21, Sep. 2008, pp. 10-11.

Clausen et al., "Lactate as an Indicator of Terminating Time in Insect Cell Culture Baculovirus Expression Vector Systems", Biotechnology Techniques, vol. 10, No. 10, Oct. 1996, pp. 721-726.

Gerlach, J.C et al., "Comparison of hollow fibre membranes for hepatocyte immobilization in bioreactors," The International Journal of Artificial Organs, 1996, vol. 19 No. 10, pp. 610-616.

Gloeckner et al., "New Miniaturized Hollow-Fiber Bioreactor for in Vivo Like Cell Culture, Cell Expansion, and Production of Cell-Derived Products", Biotechnol. Prog., Aug. 21, 2001, vol. 17, No. 5, pp. 828-831.

Grayson et al., "Effects of Hypoxia on Human Mesenchymal Stem Cell Expansion and Plasticity in 3D Constructs", J. Cellular Physiology, 2006, 207:331-339.

Lloyd, J R et al., "Hollow-Fibre bioreactors compared to batch and chemostat culture for the production of a recombinant toxoid by a marine Vibrio," Appl. Microbiol Biotechnol, Aug. 1997, vol. 48, pp. 155-161.

Neumann, Detlef et al., "Bioreaktorsteuerung mit grafischer Bedienoberflache," ATP Automatisierungstechnische Praxis, Mar. 1995, pp. 16-23, vol. 37, No. 3, Munchen, DE. (English language translation provided).

Notice of Allowance and Fee(s) Due, U.S. Appl. No. 15/616,635, dated Feb. 5, 2020.

Notice of Allowance and Fee(s) Due, U.S. Appl. No. 15/616,635, dated Apr. 22, 2020.

Notice of Allowance and Fee(s) Due, U.S. Appl. No. 15/616,745, dated Nov. 14, 2019.

Office Action, U.S. Appl. No. 15/616,635, filed Jun. 24, 2019.

Office Action, U.S. Appl. No. 15/616,745, filed Jun. 10, 2019.

Ozturk et al., "Real-Time Monitoring and Control of Glucose and Lactate Concentrations in a Mammalian Cell Perfusion Reactor", Biotechnology and Bioengineering, vol. 53, No. 4, Feb. 20, 1997, pp. 372-378.

Sauer, I. et al., "Extracorporeal liver support based on primary human liver cells and albumin dialysis—treatment of patient with primary graft non function," Journal of Hepatology, Oct. 2003, vol. 39 No. 4, pp. 649-653.

(56) References Cited

OTHER PUBLICATIONS

Wang et al., "Influence of Oxygen on the Proliferation and Metabolism of Adipose Derived Adult Stem Cells", J. Cellular Physiology, 2005, 204:184-161.
Zhao et al., "Effects of Oxygen Transport on 3-D human Mesenchymal Stem Cell Metabolic Activity in Perfusion and Static Cultures: Experiments and Mathematical Model", Biotechnol. Prog, 2005, 27, 1269-1280.
Chang et al., "Membrane Bioreactors: Present and Prospects", Advances in Biochemical Engineering, 1991, pp. 27-64, vol. 44.
Chang, Ho Nam, "Membrane Bioreactors: Engineering Aspects", Biotech. Adv., 1987, pp. 129-145, vol. 5.
Edgington, Stephen M., "New Horizons for Stem-Cell Bioreactors", Biotechnology, Oct. 1992, pp. 1099-1106, vol. 10.
Gastens et al., "Good Manufacturing Practice-Compliant Expansion of Marrow-Derived Stem and Progenitor Cells for Cell Therapy", Cell Transplantation, 2007, pp. 685-696, vol. 16.
Gramer et al., "Screening Tool for Hollow-Fiber Bioreactor Process Development", Biotechnol. Prog., 1998, pp. 203-209, vol. 14.
Hirschel et al., "An Automated Hollow Fiber System for the Large Scale Manufacture of Mammalian Cell Secreted Product", Large Scale Cell Culture Technology, ed. Bjorn K. Lydersen, 1987, pp. 113-144, Hanser Publishers.
Infanger et al., "Simulated weightlessness changes the cytoskeleton and extracellular matrix proteins in papillary thyroid carcinoma cells", Cell and Tissue Research, 2006, 324(2): 267-277.
Jones et al., "Genetic stability of bone marrow-derived human mesenchymal stromal cells in the Quantum System", Cytotherapy, 2013; 15: 1323-1339.
Liu et al., "Ex vivo Expansion of Hematopoietic Stem Cells Derived from Umbilical Cord Blood in Rotating Wall Vessel", Journal of Biotechnology, 2006, 124:592-601.
Nankervis et al., "Shear Stress Conditions in the Quantum Cell Expansion System", Poster Session—TERMIS AM Annual Conference 2013, Nov. 12, 2013.
Nguyen et al., "QUANTUM® Cell Expansion System: Automated Expansion of Human Mesenchymal Stem Cells from Precultured Cells Using the Quantum Cell Expansion System", Terumo BCT, Inc., 2012.
Nielsen, Lars Keld, "Bioreactors for Hematopoietic Cell Culture", Annu. Rev. Biomed. Eng., 1999, vol. 1, pp. 129-152.
Pörtner et al., "An Overview on Bioreactor Design, Prototyping and Process Control for Reproducible Three-Dimensional Tissue Culture", Drug Testing in Vitro: Breakthroughs and Trends in Cell Culture Technology, ed. Uwe Marx and Volker Sandig, 2007, Wiley-VCH, pp. 53-78.
Zhao et al., "Perfusion Bioreactor System for Human Mesenchymal Stem Cell Tissue Engineering: Dynamic Cell Seeding and Construct Development", Biotechnology and Bioengineering, Aug. 20, 2005, vol. 91, No. 4, pp. 482-493.
Garlie et al., "T Cells Coactivated with Immobilized Anti-CD3 and Anti-CD28 as Potential Immunotherapy for Dancer," Journal of Immunotherapy, vol. 22, No. 4, pp. 336-345, 1999.
Ge Healthcare Uk Limited, "The Effect of Rocking Rate and Angle on T Cell Cultures Grown in Xuri(TM) Cell Expansion Systems," Cell therapy bioreactor systems, Application note 29-1166-55 AA, pp. 1-4, vww.gelifesciences.com/xuri, Aug. 2014.
Ueda et al., "Interaction of Natural Killer Cells with Neutrophils Exerts a Significant Antitumor Immunity in Hematopoietic Stem Cell Transplantation Recipients," Cancer Medicine, vol. 5, No. 1, pp. 49-60, 2016.
Urbich et al., "Fluid Shear Stress-induced Transcriptional Activation of the Vascular Endothelial Growth Factor Receptor-2 Gene Requires Sp1-Dependent DNA Binding," FEBS Letters, 535, pp. 87-93, 2003.
Von Laer, D., "Loss of CD38 Antigen on CD34 CD38 Cells during Short-term Culture," Leukemia, Correspondence, pp. 947-948, 1999.

Wagner et al., "Phase I/II Trial of StemRegenin-1 Expanded Umbilical Cord Blood Hematopoietic Stem Cells Supports Testing as a Stand-alone Graft," Cell Stem Cell, vol. 18, pp. 144-155, Jan. 7, 2016.
Weaver et al., "An Analysis of Engraftment Kinetics as a Function of the CD34 Content of Peripheral Blood Progenitor Cell Collections in 692 Patients after the Administration of Myeloablative Chemotherapy," Blood, vol. 86, No. 10, pp. 3961-3969, Nov. 15, 1995.
Kang et al., "Suspension Culture of Mammalian Cells Using Thermosensitive Microcarrier that Allows Cell Detachment without Proteolytic Enzyme Treatment," Cell Transplantation, vol. 19, pp. 1123-1132, Aug. 18, 2010.
Yi et al., "A Readily Modified Polyethersulfone with Amino-Substituted Groups: Its Amphiphilic Copolymer Synthesis and Membrane Application," Polymer, vol. 53, pp. 350-358, Dec. 2, 2011.
Zheng et al., "Differential Effects of Cyclic and Static Stretch on Coronary Microvascular Endothelial Cell Receptors and Vasculogenic/Angiogenic Responses," American Journal of Physiology—Heart and Circulatory Physiology, vol. 295, H794-H800, Aug. 2008.
Abumiya et al., "Shear Stress Induces Expression of Vascular Endothelial Growth Factor Receptor Flk-1/KDR Through the CT-Rich Sp1 Binding Site," Ateriosclerosis, Thrombosis, and Vascular Biology, vol. 22, pp. 907-913, Jun. 2002.
Akiyama et al., "Ultrathin Poly(N-isopropylacrylamide) Grafted Layer on Polystyrene Surfaces for Cell Adhesion/Detachment Control," Langmuir, vol. 20, No. 13, pp. 5506-5511, May 26, 2004.
Akram et al., "Mesenchymal Stem Cells Promote Alveolar Epithelial Cell Wound Repair in vitro through Distinct Migratory and Paracrine Mechanisms," Respiratory Research, vol. 14, No. 9, pp. 1-16, 2013.
Alenazi et al., "Modified Polyether-sulfone Membrane: a Mini Review," Designed Monomers And Polymers, vol. 20, No. 1, pp. 532-546, 2017.
Anamelechi et al., "Streptavidin Binding and Endothelial Cell Adhesion to Biotinylated Fibronectin," Langmuir, vol. 23, No. 25, pp. 12583-12588, Dec. 4, 2007.
Azar et al., "Heart Rates of Male and Female Sprague-Dawley and Spontaneously Hypertensive Rats Housed Singly or in Groups," Journal of the American Association for Laboratory Animal Science, vol. 50, No. 2, pp. 175-184, Mar. 2011.
Bai et al., "Expansion of Primitive Human Hematopoietic Stem Cells by Culture in a Zwitterionic Hydrogel," Nature Medicine, vol. 25, pp. 1566-1575, Oct. 2019.
Barker et al., "CD34+ Cell Content of 126 341 Cord Blood Units in the US Inventory: Implications for Transplantation and Banking," Blood Advances, vol. 3, No. 8, pp. 1267-1271, Apr. 23, 2019.
Beacher-Allan et al., "CD4+CD25high Regulatory Cells in Human Peripheral Blood," The Journal of Immunology, vol. 167, pp. 1245-1253, 2001.
Boitano et al., "Aryl Hydrocarbon Receptor Antagonists Promote the Expansion of Human Hematopoietic Stem Dells," Science, vol. 329, No. 5997, pp. 1345-1348, Sep. 10, 2010. Corrected May 6, 2011.
Brunstein et al., "Infusion of ex vivo Expanded T Regulatory Cells in Adults Transplanted with Umbilical Cord Blood Safety Profile and Detection Kinetics," Blood, vol. 117, No. 3, pp. 1061-1070, Jan. 20, 2011.
Bryce et al., "In vitro Micronucleus Assay Scored by Flow Cytometry Provides a Comprehensive Evaluation of Cytogenetic Damage and Cytotoxicity," Mutation Research, vol. 630, pp. 78-91, Mar. 19, 2007.
Bryce et al., "Interlaboratory Evaluation of a Flow Cytometric, High Content in vitro Micronucleus Assay," Mutation Research, vol. 650, pp. 181-195, Jan. 7, 2008.
Camacho Villa et al., "CD133+CD34+ and CD133+CD38+ Blood Progenitor Cells as Predictors of Platelet Engraftment in Patients Undergoing Autologous Peripheral Blood Stem Cell Transplantation," Transfusion and Apheresis Science, vol. 46, pp. 239-244, 2012.

(56) References Cited

OTHER PUBLICATIONS

Cano et al., "Immobilization of endo-1,4-β-xylanase on Polysulfone Acrylate Membranes: Synthesis and Characterization," Journal of Membrane Science, vol. 280, pp. 383-388, Feb. 28, 2006.
Carvell and Dowd, "On-line Measurements and Control of Viable Cell Density in Cell Culture Manufacturing Processes Using Radio Frequency Impedance," Cytotechnology, vol. 50, pp. 35-48, 2006.
Carvell et al., "Monitoring Live Biomass in Disposable Bioreactors," BioProcess International, vol. 14, No. 3, pp. 40-48, Mar. 2016.
Cuchiara et al., "Covalent Immobilization of SCF and SDF1α for in vitro Culture of Hematopoietic Progenitor Cells," Acta Biomaterials, vol. 9, No. 12, pp. 9258-9269, Dec. 2013.
Da Silva et al., "Smart Thermoresponsive Coatings and Surfaces for Tissue Engineering: Switching Cell-Material Boundaries," TRENDS in Biotechnology, vol. 15, No. 12, pp. 577-583, 2007.
Hao et al., "A Functional Comparison of CD34+ CD38- Cells in Cord Blood and Bone Marrow," Blood, vol. 86, No. 10, pp. 3745-3753, Nov. 15, 1995.
Harimoto et al., "Novel Approach for Achieving Double-Layered Cell Sheets Co-Culture: Overlaying Endothelial Cell Sheets onto Monolayer Hepatocytes Utilizing Temperature-Responsive Culture Dishes," Journal of Biomedical Materia Research, vol. 62, pp. 464-470, 2002.
Högstedt et al., "Frequency and Size Distribution of Micronuclei in Lymphocytes Stimulated with Phytohemagglutinin and Pokeweed Mitogen in Workers Exposed to Piperazine," Hereditas, vol. 109, pp. 139-142, 1988.
Horwitz et al., "Phase I/II Study of Stem-Cell Transplantation Using a Single Cord Blood Unit Expanded Ex Vivo with Nicotinamide," Journal of Clinical Oncology, vol. 37, No. 5, pp. 367-376, Dec. 4, 2018.
Itkin and Lapidot, "SDF-1 Keeps HSC Quiescent at Home," Blood, vol. 117, No. 2, pp. 373-374, Jan. 13, 2011.
Jang et al., "Syndecan-4 Proteoliposomes Enhance Fibroblast Growth Factor-2 (FGF-2)-Induced Proliferation, Migration, and Neovascularization of Ischemic Muscle," PNAS, vol. 109, No. 5, pp. 1679-1684, Jan. 31, 2012.
Johansson et al., "Pancreatic Islet Survival and Engraftment Is Promoted by Culture on Functionalized Spider Silk Matrices," PLoS ONE, pp. 1-21, Jun. 19, 2015.
Klein et al., "Affinity Membranes Prepared from Hydrophilic Coatings on Microporous Polysulfone Hollow Fibers," Journal of Membrane Science, vol. 90, pp. 69-80, 1994.
Koesienbauer et al., "Protocols for Hematopoietic Stem Cell Expansion from Umbilical Cord Blood," Cell Transplantation, vol. 18, pp. 1059-1068, May 6, 2009.
Koller et al., "Clinical-scale Human Umbilical Cord Blood Cell Expansion in a Novel Automated Perfusion Culture System," Bone Marrow Transplantation, vol. 21, pp. 653-663, 1998.
Lang et al., "Generation of Hematopoietic Humanized Mice in the Newborn BALB/C-Rag2null Il2rynull Mouse Model: A Multivariable Optimization Approach," Clinical Immunology, vol. 140, pp. 102-116, Apr. 14, 2011.
Lataillade et al., "Chemokine SDF-1 Enhances Circulating CD341 Cell Proliferation in Synergy with Cytokines: Possible Role in Progenitor Survival," Blood, vol. 95, No. 3, pp. 756-768, Feb. 1, 2000.
Lee et al., "Long-Term Outcomes Following CD19 CAR T Cell Therapy for B-ALL Are Superior in Patients Receiving a Fludarabine/ Cyclophosphamide Preparative Regimen and Post-CAR Hematopoietic Stem Cell Transplantation," Blood, vol. 128, No. 22, Ab. 218, Dec. 2, 2016.
Li et al., "Heparin-induced Conformation Changes of Fibronectin within the Extracellular Matrix Promote hMSC Osteogenic Differentiation," Biomaterials Science, vol. 3, pp. 73-84, 2015.
Malin et al., "Noninvasive Prediction of Glucose by Near-Infrared Diffuse Reflectance Spectroscopy," Clinical Chemistry, vol. 45, No. 9, 1651-1658, 1999.
Marek-Trzonkowska et al., "Administration of CD4+ CD25high CD127- Regulatory T Cells Preserves β-Cell Function in Type 1 Diabetes in Children," Diabetes Care, vol. 35, No. 9, pp. 1817-1820, Sep. 2012.
Murugappan et al., "Human Hematopoietic Progenitor Cells Grow Faster under Rotational Laminar Flows," Biotechnology Progress—Cell Culture & Tissue Engineering, Online, Apr. 22, 2010.
Nelson et al., "Emergent Patterns of Growth Controlled by Multicellular Form and Mechanics," PNAS, vol. 102, No. 33, p. 11594-11599, Aug. 16, 2005.
Nicolette et al., "In Vitro Micronucleus Screening of Pharmaceutical Candidates by Flow Cytometry in Chinese Hamster V79 Cells," Environmental and Molecular Mutagenesis, vol. 52, pp. 355-362, Oct. 20, 2010.
Nugent et al., "Adventitial Endothelial Implants Reduce Matrix Metalloproteinase-2 Expression and Increase Luminal Diameter in Porcine Arteriovenous Grafts," Journal of Vascular Surgery, vol. 46, No. 3, pp. 548-556.e2, Sep. 2007.
Okano et al., "Mechanism of Cell Detachment from Temperature-Modulated, Hydrophilic-Hydrophobic Polymer Surfaces," Biomaterials, vol. 16, No. 4, pp. 297-303, 1995.
Putnam et al., "Expansion of Human Regulatory T-Cells from Patients with Type 1 Diabetes," Diabetes, vol. 58, pp. 352-662, Mar. 2009.
Rahmahwati et al., "The Synthesis of Polyethersulfone (PES) Derivatives for the Immobilization of Lipase Enzyme," Key Engineering Materials, vol. 811, pp. 14-21, Jul. 8, 2019.
Rodrigues et al., "Stem Cell Cultivation in Bioreactors," Biotechnology Advances, vol. 29, pp. 815-829, Jun. 25, 2011.
Ronco et al., "Blood and Dialysate Flow Distributions in Hollow-Fiber Hemodialyzers Analyzed by Computerized Helical Scanning Technique," Journal of the American Society of Nephrology, vol. 13, pp S53-S61, 2002.
Ryu and Gomelsky, "Near-infrared Light Responsive Synthetic c-di-GMP Module for Optogenetic Applications," ACS Synthetic Biology, vol. 3, pp. 802-810, Jan. 28, 2014.
Shimizu et al., "Fabrication of Pulsatile Cardiac Tissue Grafts Using a Novel 3-Dimensional Cell Sheet Manipulation Technique and Temperature-Responsive Cell Culture Surfaces," Circulation Research, vol. 90, e40-e48, pp. 1-9, Feb. 22, 2002.
Smith et al., "Expansion of Neutrophil Precursors and Progenitors in Suspension Cultures of CD34+ Cells Enriched from Human Bone Marrow," Experimental Hematology, vol. 21, pp. 870-877, 1993.
Streltsova et al., "Recurrent Stimulation of Natural Killer Cell Clones with K562 Expressing Membrane-Bound Interleukin-21 Affects Their Phenotype, Interferon-γ Production, and Lifespan," International Journal of Molecular Sciences, vol. 20, No. 443, pp. 1-18, 2019.
Takezawa et al., "Cell Culture on a Thermo-responsive Polymer Surface," Nature, Bio/Technology, vol. 8, pp. 354-856, Sep. 1990.
Tiziani et al., "Metabolomic Profiling of Drug Response in Acute Myeloid Leukaemia Cell lines," PLoS ONE, vol. 4, Issue 1, e4251, Jan. 22, 2009.

* cited by examiner

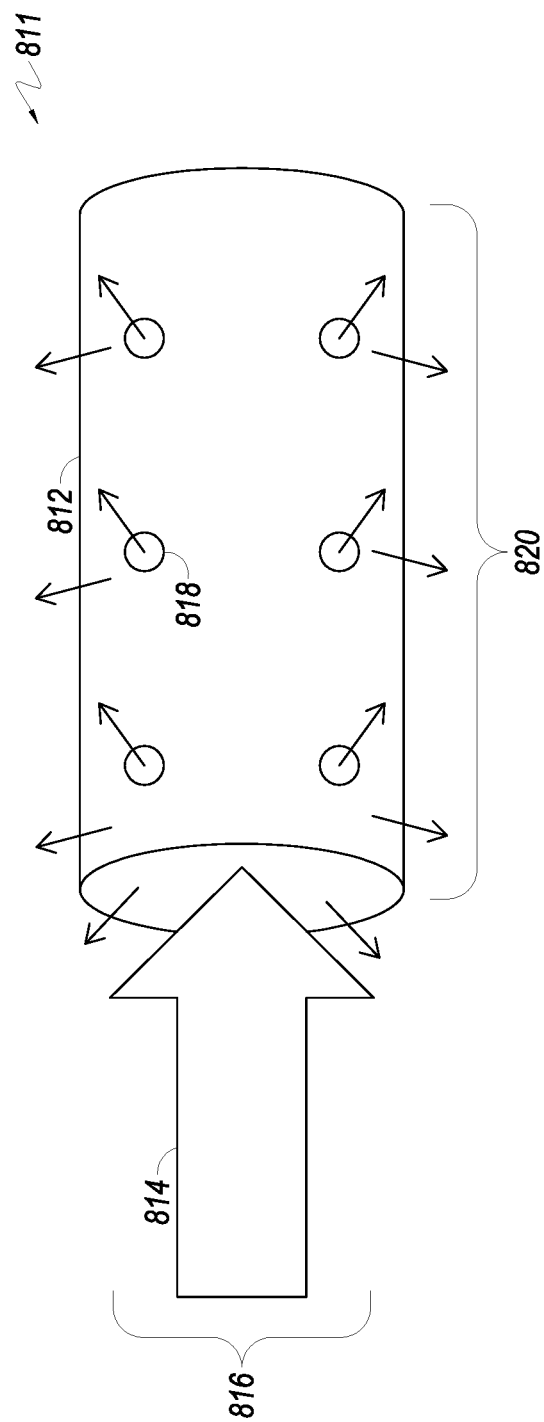

| IC Inlet: (100mL SDE CPPT) | Step 1 | Step 2 | Step 3 |
|---|---|---|---|
| IC Inlet Rate (mL/min) | Reagent | Wash | Wash |
|  | 10 | 10 | 50 |
| IC Circulation Rate (mL/min) | 100 | 100 | -25 |
| EC Inlet | None | None | Wash |
| EC Inlet Rate (mL/min) | 0 | 0 | 0.1 |
| EC Circulation Rate (mL/min) | 30 | 30 | 30 |
| Outlet | EC Outlet | EC Outlet | EC Outlet |
| Rocker Control | Stationary (0) | Stationary (0) | Stationary (0) |
| Stop Condition | Empty Bag | IC Volume: 22mL | Time: 10.0 min |

FIG. 8C

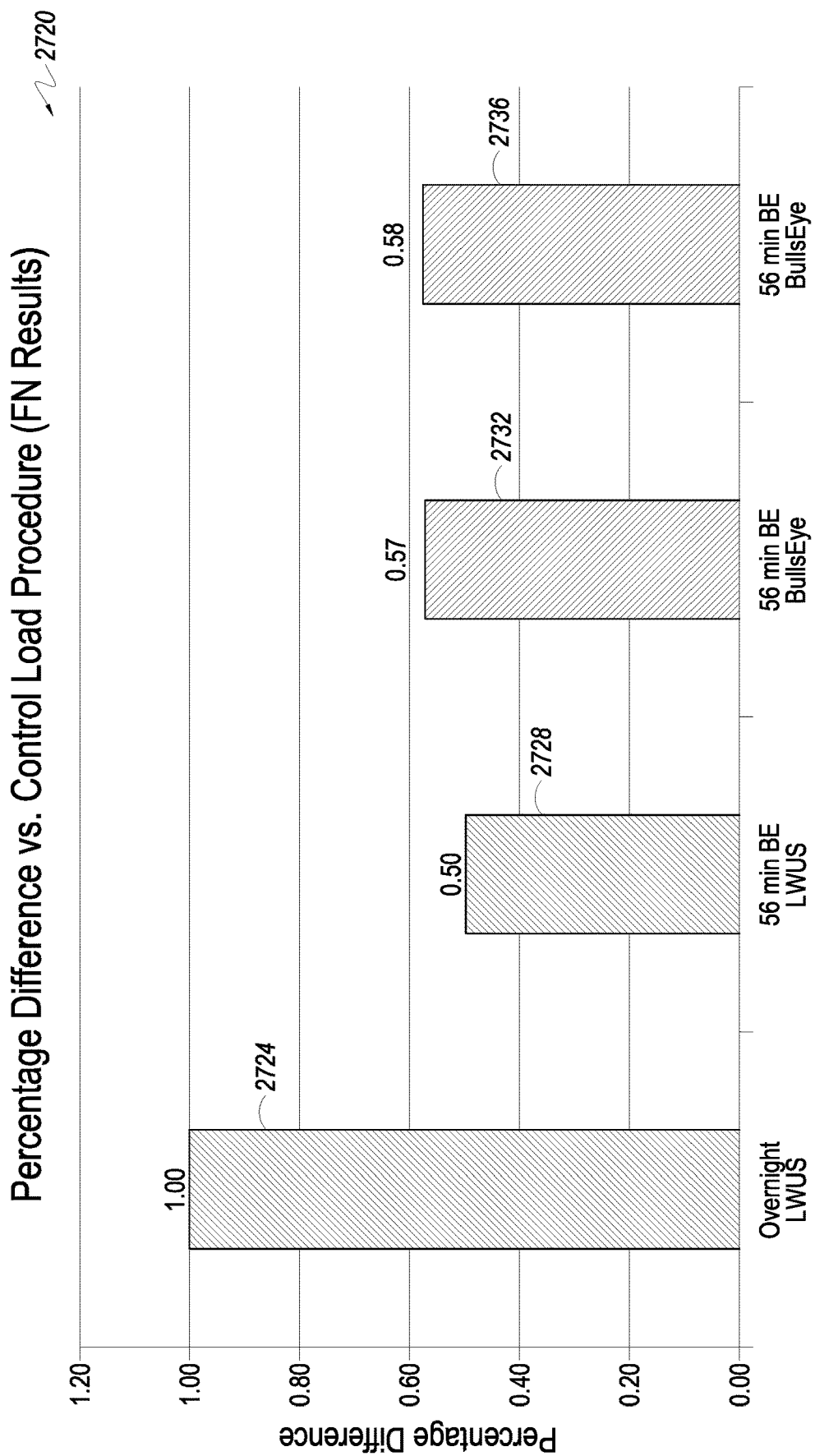

COATING A BIOREACTOR

CROSS-REFERENCE TO RELATED APPLICATION

This application claims priority to, and the benefit of, U.S. Provisional Application Ser. No. 62/347,025, filed on Jun. 7, 2016, and entitled, "Growth Surface Coating," and U.S. Provisional Application Ser. No. 62/347,012, filed on Jun. 7, 2016, and entitled, "Coating a Bioreactor." The disclosure of the two above-identified provisional applications are hereby incorporated by reference in their entirety as if set forth herein in full for all that they teach and for all purposes.

BACKGROUND

Cell Expansion Systems (CESS) may be used to expand and differentiate cells. Cell expansion systems may be used to expand, e.g., grow, a variety of adherent and suspension cells. For example, cell expansion systems may be used to expand mesenchymal stem cells (MSCs) and other types of cells, such as bone marrow cells. Stem cells which are expanded from donor cells may be used to repair or replace damaged or defective tissues and have broad clinical applications for a wide range of diseases. Cells, of both adherent and non-adherent type, may be grown in a bioreactor in a cell expansion system.

SUMMARY

Embodiments of the present disclosure generally relate to a cell expansion system for expanding cells. Such expansion may occur through the use of a bioreactor or cell growth chamber comprising a hollow fiber membrane. In embodiments, a hollow fiber membrane comprises a plurality of hollow fibers. Such hollow fiber membrane may include an extracapillary (EC) space and an intracapillary (IC) space. A cell expansion system may expand a variety of cell types, such as mesenchymal stem cells, cancer cells, T-cells, fibroblasts, and myoblasts. In expanding cells, a compound or coating agent may be applied to a cell growth surface. For example, an adherence-promoting compound may be applied to a cell growth surface to promote contact, e.g., adherence, and subsequent expansion of cells, such as a cell line including human mesenchymal stem cells (hMSCs). In embodiments, for cells to adhere to the surface of the hollow fibers, the surface may be modified in some way, such as by coating at least the cell growth surface with a protein, for example. In embodiments, a coating agent may be applied to the inner surface or inner aspect of bioreactor fibers. For example, a coating agent may be applied to the intracapillary (IC) surface of a hollow fiber(s). In another embodiment, a coating agent may be applied to the extracapillary (EC) surface of a hollow fiber(s). As non-limiting examples of coating agent(s), cryoprecipitate (CPPT), fibronectin (FN), human fibronectin (hFN), and/or combinations of such coating agents may be used. In other embodiments, a plurality of coating agents, or a combination of coating agent(s), may be used.

Embodiments provide for fluid movement in a cell growth chamber or bioreactor to be controlled to actively promote a coating agent(s) to a cell growth surface, e.g., to a surface of a hollow fiber(s). For example, such fluid movement may be controlled so as to move fluid from one side, e.g., IC side, of a hollow fiber to the other side, e.g., EC side, of the hollow fiber. In an embodiment, ultrafiltration may be used to move fluid in a bioreactor. For example, positive ultrafiltration may be used to move fluid from the IC side of a bioreactor to the EC side of the bioreactor. In another embodiment, negative ultrafiltration may be used to move fluid from the EC side of a bioreactor to the IC side of the bioreactor. In embodiments, other types of ultrafiltration or directions of fluid movement may be used. The direction of fluid movement may depend on the surface upon which cells are being expanded.

By controlling fluid movement, a coating solution, e.g., a fluid(s) and a coating agent(s), may be actively pushed to the IC (or EC) loop, and the fluid(s) may be pushed through the pores, for example, of a hollow fiber(s), leaving a residual layer of adherence-promoting protein(s), for example, on the IC (or EC) side of the hollow fiber(s) and therefore facilitating the contact, e.g., attachment, of cells, e.g., adherent cells. Such fluid movement, e.g., ultrafiltration, may decrease the time required for a chemical reaction between a coating agent and the growth surface of the bioreactor to occur to coat the fiber(s). Such fluid movement may be controlled through the adjusting of one or more valve(s), pump(s), or other type of fluid flow control device(s).

Embodiments of the present disclosure provide for implementing such coating procedure(s) through the use of one or more protocols or tasks for use with a cell expansion system. Such protocols or tasks may include pre-programmed protocols or tasks for use with an automated CES, for example. In embodiments, a pre-programmed, default, or otherwise previously saved task may be selected. A task may comprise one or more steps. In other embodiments, such protocols or tasks may include custom or user-defined protocols or tasks for use with an automated CES, for example. Through a user interface (UI) and graphical user interface (GUI) elements, a custom or user-defined protocol or task may be created. In embodiments, a combination of pre-programmed, default, custom, and/or user-defined tasks, for example, may be used.

In addition, ultrafiltration may be combined with other processes for coating a cell growth surface, e.g., a surface of a hollow fiber. For example, some coating processes referred to as a bulls-eye coat process may provide for changing flow rates, flow directions, and rotation of a bioreactor during a coating process to improve distribution of the coating agent throughout the bioreactor. Embodiments provide for combining ultrafiltration, such as by continuously introducing a wash fluid into the bioreactor, while other steps (e.g., changing flow rates, flow directions, and rotation of a bioreactor) are performed.

Other embodiments provide for combining processes of coating a cell growth surface, e.g., a surface of a hollow fiber with processes for loading and attaching cells. For example, a bulls-eye coat process may be combined with a bulls-eye load process. The coating process may provide for changing flow rates, flow directions, and rotation of a bioreactor during a coating process, while the bulls-eye load may provide for changing flow rates, flow directions, and rotation of a bioreactor during a process of loading and attaching cells.

This Summary is included to provide a selection of concepts in a simplified form, in which such concepts are further described below in the Detailed Description. This Summary is not intended to be used in any way to limit the claimed subject matter's scope. Features, including equivalents and variations thereof, may be included in addition to those provided herein.

BRIEF DESCRIPTION OF THE DRAWINGS

Embodiments of the present disclosure may be described by referencing the accompanying figures. In the figures, like numerals refer to like items.

FIG. 8B depicts a schematic of applying an agent to a cell growth surface of a hollow fiber in accordance with embodiments of the present disclosure.

FIG. 8C illustrates example steps and parameters for applying an agent to a cell growth surface in accordance with an embodiment of the present disclosure.

FIG. 27B depicts example results of expanding cells using various coating and cell loading procedures in accordance with embodiments.

DETAILED DESCRIPTION

Figure 1A:
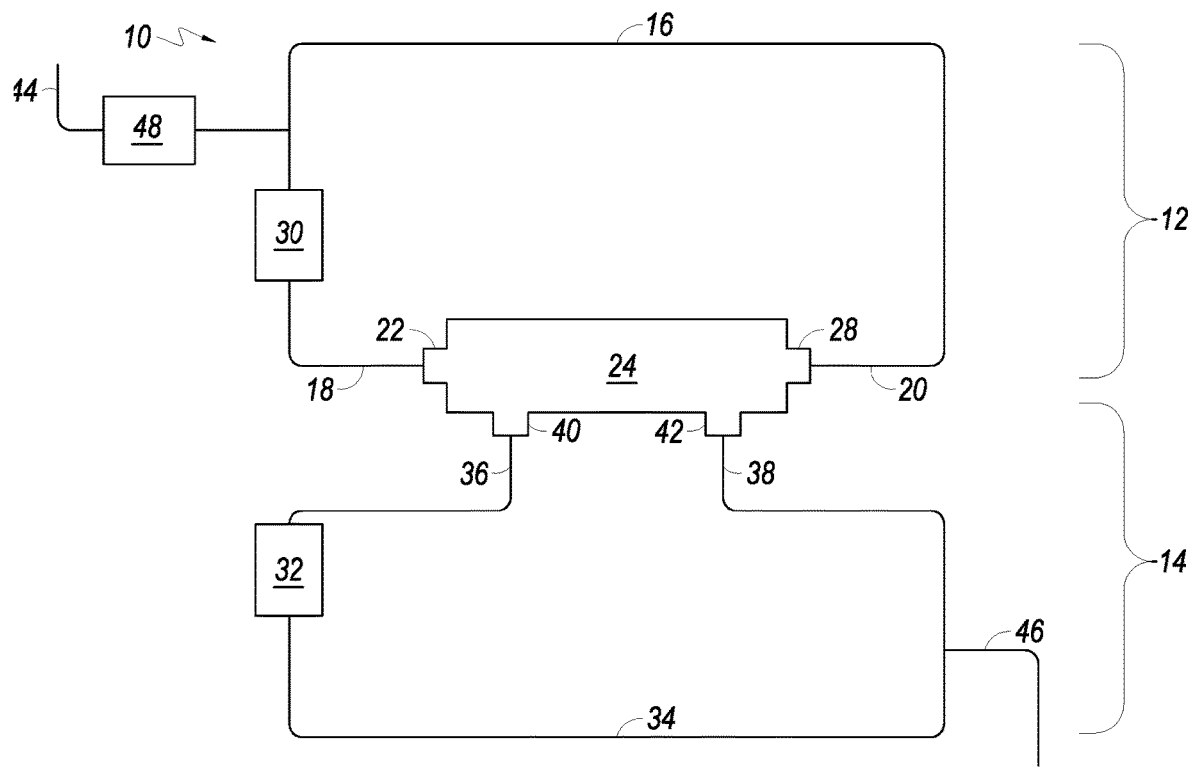
FIG. 1A depicts an embodiment of a cell expansion system (CES).

The following Detailed Description provides a discussion of illustrative embodiments with reference to the accompanying drawings. The inclusion of specific embodiments herein should not be construed as limiting or restricting the present disclosure. Further, while language specific to features, acts, and/or structures, for example, may be used in describing embodiments herein, the claims are not limited to the features, acts, and/or structures described. A person of skill in the art will appreciate that other embodiments, including improvements, are within the spirit and scope of the present disclosure. Further, any alternatives or additions, including any listed as separate embodiments, may be used or incorporated with any other embodiments herein described.

Embodiments of the present disclosure are generally directed to methods and systems for applying a coating agent or reagent to a cell growth surface to promote cell contact, e.g., adherence, and subsequent expansion of cells. In an embodiment, such application comprises an active promotion of a coating agent or reagent to the cell growth surface, such as the cell growth surface of a hollow fiber(s) where a hollow fiber bioreactor may be used for cell expansion in a cell expansion system. Controlling fluid movement in a bioreactor or cell growth chamber allows for the active promotion of a coating agent or reagent to a cell growth surface.

Passive coating processes may involve the passive application of a coating agent to a cell growth surface, in which a coating agent(s) may be passively applied to a cell growth chamber of an automated cell expansion system using circulating flow, for example. A coating agent(s) may be loaded into an intracapillary or extracapillary side of a bioreactor, for example. The coating agent(s) may then be circulated in the intracapillary or extracapillary loop for a particular, e.g., first, time period. As such, the bioreactor may be passively coated using circulating flow in the IC (or EC) loop, in which such process may take multiple hours, for example. Such coating procedure may take from about four (4) hours to about twenty-four (24) hours, for example, of circulation of a coating agent to achieve coating of the cell growth surface. As an example, a bioreactor coating protocol may load a coating agent into the intracapillary side of a bioreactor in a cell expansion system. The coating agent may then be circulated in the intracapillary circulation loop for a minimum of sixteen (16) hours. A user utilizing such process may therefore use at least two cell expansion systems, in which the user may begin, in a second cell expansion system, any additional expansion of a population of cells harvested from a first cell expansion system (where cells may not be stored in a non-cryopreserved state for up to sixteen (16) hours, for example).

Embodiments herein provide for the active pushing or active promotion of a coating agent solution to a cell growth surface. Rather than passively coating the bioreactor using circulating flow in the IC loop, for example, for many hours, a coating solution, e.g., a fluid(s) and a coating agent(s), can be actively pushed into the IC loop, and the fluid(s) may be pushed through the pores of the bioreactor, leaving a residual layer of adherence promoting proteins on the IC side of the bioreactor fibers to facilitate the attachment of adherent cells. In an embodiment, ultrafiltration may be used to allow a coating agent or reagent to be promoted to the growth surface of a hollow fiber, for example. Ultrafiltration, e.g., positive ultrafiltration, may be used to move fluid from a first side of a hollow fiber to a second side of a hollow fiber. For example, utilizing positive ultrafiltration of a fluid, the fluid may be moved from the IC side of a hollow fiber or hollow fiber membrane to the EC side of the hollow fiber or hollow fiber membrane. Such fluid movement may decrease the time it takes for a chemical reaction to occur between a coating agent or reagent and a growth surface of the bioreactor to coat the cell growth surface. The molecular barrier created by the specified construction of the hollow fibers in the bioreactor may be such that the coating agent or reagent may not be able to pass through the fiber wall along with the fluid in which it is suspended. The adherence promoting proteins of the coating agent may remain in a residual layer on a first side of the hollow fiber(s) as the solution is pushed through the pores of the fibers to a second side of the hollow fiber(s). Moving the fluid using ultrafiltration, e.g., positive ultrafiltration, may thus result in "actively" promoting the coating agent or reagent to the surface of the hollow fiber(s), according to embodiments.

For example, a coating agent(s) may be introduced to the fibers of a hollow fiber bioreactor on the IC (or EC) side. Such coating agent(s) may be suspended in a solution, e.g., coating solution. The IC outlet or waste valve may be closed, with the EC outlet or waste valve open. The IC inlet rate may be set to wash the IC side with media, such as phosphate buffered saline (PBS), for example. Such fluid may have no pathway but through the pores of the fibers (IC outlet valve closed). Accordingly, the solution may flow through the pores of the fibers from the IC side to the EC side. The coating agent, e.g., CPPT, may be hydrostatically deposited onto the inner wall(s) of the bioreactor fiber for a defined time period. For example, such time period may be about ten (10) minutes, according to an embodiment. Such membrane ultrafiltration method allows adherence promoting proteins to be physisorbed on the bioreactor fibers as the solution flows through the pores of the fiber from the IC side to the EC side, for example.

In an embodiment, such active moving of the coating agent to the cell growth surface(s) may significantly decrease the amount of time it may take to coat the cell growth surface as compared to other methods of coating a cell growth surface. In embodiments, such coating procedure using ultrafiltration may be referred to as an expedited coating procedure. Such expedited coating procedure using active moving of the coating agent to the cell growth surface(s) through ultrafiltration may use less time to coat the cell growth surface than procedures using passive coating procedures which may take overnight or about twelve (12) hours to about sixteen (16) hours to coat the bioreactor. For example, such expedited coating procedure may take less than or equal to about four (4) hours. In embodiments, such expedited coating procedure may take any time period in a range from above or equal to about five (5) minutes to less than or equal to about sixty (60) minutes, or any other range therein, depending on the procedure. For example, such coating procedure may take less than or equal to about ten (10) minutes, less than or equal to about twelve (12) minutes, less than or equal to about fifteen (15) minutes, less than or equal to about twenty (20) minutes, less than or equal to about thirty (30) minutes, less than or equal to about forty-five (45) minutes, less than or equal to about sixty (60) minutes, etc.

Embodiments are directed to a cell expansion system, as described above. In embodiments, such cell expansion system is closed, in which a closed cell expansion system comprises contents that are not directly exposed to the atmosphere. Such cell expansion system may be automated. In embodiments, cells, of both adherent and non-adherent or suspension type, may be grown in a bioreactor in the cell expansion system. According to embodiments, the cell expansion system may include base media or other type of media. Methods for replenishment of media are provided for cell growth occurring in a bioreactor of the closed cell expansion system. In embodiments, the bioreactor used with such systems is a hollow fiber bioreactor. Many types of bioreactors may be used in accordance with embodiments of the present disclosure.

The system may include, in embodiments, a bioreactor that further includes a first fluid flow path having at least opposing ends, a first opposing end of the first fluid flow path fluidly associated with a first port of a hollow fiber membrane and a second end of the first fluid flow path fluidly associated with a second port of the hollow fiber membrane, in which the first fluid flow path comprises an intracapillary portion of the hollow fiber membrane. In embodiments, a hollow fiber membrane comprises a plurality of hollow fibers. The system may further include a fluid inlet path fluidly associated with the first fluid flow path, in which a plurality of cells are introduced into the first fluid flow path through a first fluid inlet path. A first pump for circulating fluid in the first fluid flow path of the bioreactor may also be included. In embodiments, the system includes a controller for controlling operation of the first pump. In an embodiment, the controller is a computing system, including a processor, for example. The controller is configured, in embodiments, to control the pump to circulate a fluid at a first rate within the first fluid flow path. In some embodiments, a second pump for transferring intracapillary inlet fluid from an intracapillary media bag to the first fluid flow path and a second controller for controlling operation of the second pump are included. The second controller, in embodiments, controls the second pump to transfer cells from a cell inlet bag to the first fluid flow path, for example. Additional controllers, e.g., third controller, fourth controller, fifth controller, sixth controller, etc., may be used in accordance with embodiments. Further, additional pumps, e.g., third pump, fourth pump, fifth pump, sixth pump, etc., may be used in accordance with embodiments of the present disclosure. In addition, while the present disclosure may refer to a media bag, a cell inlet bag, etc., multiple bags, e.g., a first media bag, a second media bag, a third media bag, a first cell inlet bag, a second cell inlet bag, a third cell inlet bag, etc., and/or other types of containers, may be used in embodiments. In other embodiments, a single media bag, a single cell inlet bag, etc., may be used. Further, additional or other fluid paths, e.g., a second fluid flow path, a second fluid inlet path, etc., may be included in embodiments.

In other embodiments, the system is controlled by, for example: a processor coupled to the cell expansion system; a display device, in communication with the processor, and operable to display data; and a memory, in communication with and readable by the processor, and containing a series of instructions. In embodiments, when the instructions are executed by the processor, the processor receives an instruction to coat the bioreactor, for example. In response to the instruction to coat the bioreactor, the processor may execute a series of steps to coat the bioreactor and may next receive an instruction to load cells into the bioreactor, for example. In response to the instruction to load cells, the processor may execute a series of steps to load the cells from a cell inlet bag, for example, into the bioreactor.

A schematic of an example cell expansion system (CES) is depicted in FIG. 1A, in accordance with embodiments of the present disclosure. CES 10 includes first fluid circulation path 12 and second fluid circulation path 14. First fluid flow path 16 has at least opposing ends 18 and 20 fluidly associated with a hollow fiber cell growth chamber 24 (also referred to herein as a "bioreactor"), according to embodiments. Specifically, opposing end 18 may be fluidly associated with a first inlet 22 of cell growth chamber 24, and opposing end 20 may be fluidly associated with first outlet 28 of cell growth chamber 24. Fluid in first circulation path 12 flows through the interior of hollow fibers 116 (see FIG. 1B) of hollow fiber membrane 117 (see FIG. 1B) disposed in cell growth chamber 24 (cell growth chambers and hollow fiber membranes are described in more detail infra). Further, first fluid flow control device 30 may be operably connected to first fluid flow path 16 and may control the flow of fluid in first circulation path 12.

Second fluid circulation path 14 includes second fluid flow path 34, cell growth chamber 24, and a second fluid flow control device 32. The second fluid flow path 34 has at least opposing ends 36 and 38, according to embodiments. Opposing ends 36 and 38 of second fluid flow path 34 may be fluidly associated with inlet port 40 and outlet port 42 respectively of cell growth chamber 24. Fluid flowing through cell growth chamber 24 may be in contact with the outside of hollow fiber membrane 117 (see FIG. 1B) in the cell growth chamber 24, in which a hollow fiber membrane comprises a plurality of hollow fibers. Second fluid circulation path 14 may be operably connected to second fluid flow control device 32.

Figure 1B:
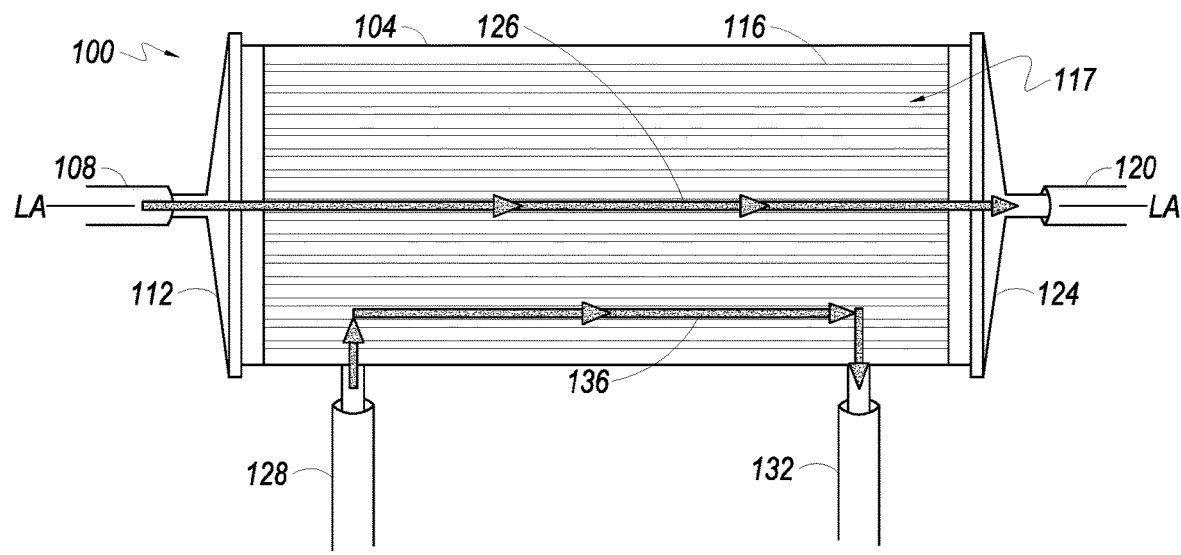
FIG. 1B illustrates a front elevation view of an embodiment of a bioreactor showing circulation paths through the bioreactor.

First and second fluid circulation paths 12 and 14 may thus be separated in cell growth chamber 24 by a hollow fiber membrane 117 (see FIG. 1B). Fluid in first fluid circulation path 12 flows through the intracapillary ("IC") space of the hollow fibers in the cell growth chamber 24. First circulation path 12 may be referred to as the "IC loop." Fluid in second circulation path 14 flows through the extracapillary ("EC") space in the cell growth chamber 24. Second fluid circulation path 14 may be referred to as the "EC loop." Fluid in first fluid circulation path 12 may flow in either a co-current or counter-current direction with respect to the flow of fluid in second fluid circulation path 14, according to embodiments.

Fluid inlet path 44 may be fluidly associated with first fluid circulation path 12. Fluid inlet path 44 allows fluid into first fluid circulation path 12, while fluid outlet path 46 allows fluid to leave CES 10. Third fluid flow control device 48 may be operably associated with fluid inlet path 44. Alternatively, third fluid flow control device 48 may alternatively be associated with first outlet path 46.

Fluid flow control devices as used herein may comprise a pump, valve, clamp, or combination thereof, according to embodiments. Multiple pumps, valves, and/or clamps can be arranged in any combination. In various embodiments, the fluid flow control device is or includes a peristaltic pump. In embodiments, fluid circulation paths, inlet ports, and outlet ports may be constructed of tubing of any material.

Various components are referred to herein as "operably associated." As used herein, "operably associated" refers to components that are linked together in operable fashion and encompasses embodiments in which components are linked directly, as well as embodiments in which additional components are placed between the two linked components. "Operably associated" components can be "fluidly associated." "Fluidly associated" refers to components that are linked together such that fluid can be transported between them. "Fluidly associated" encompasses embodiments in which additional components are disposed between the two fluidly associated components, as well as components that are directly connected. Fluidly associated components can include components that do not contact fluid, but contact other components to manipulate the system (e.g., a peristaltic pump that pumps fluids through flexible tubing by compressing the exterior of the tube).

Generally, any kind of fluid, including buffers, protein containing fluid, and cell-containing fluid, for example, can flow through the various circulations paths, inlet paths, and outlet paths. As used herein, "fluid," "media," and "fluid media" are used interchangeably.

Turning to FIG. 1B, an example of a hollow fiber cell growth chamber 100 which may be used with the present disclosure is shown in front side elevation view. Cell growth chamber 100 has a longitudinal axis LA-LA and includes cell growth chamber housing 104. In at least one embodiment, cell growth chamber housing 104 includes four openings or ports: IC inlet port 108, IC outlet port 120, EC inlet port 128, and EC outlet port 132.

According to embodiments of the present disclosure, fluid in a first circulation path enters cell growth chamber 100 through IC inlet port 108 at a first longitudinal end 112 of the cell growth chamber 100, passes into and through the intracapillary side (referred to in various embodiments as the intracapillary ("IC") side or "IC space" of a hollow fiber membrane) of a plurality of hollow fibers 116 comprising hollow fiber membrane 117, and out of cell growth chamber 100 through IC outlet port 120 located at a second longitudinal end 124 of the cell growth chamber 100. The fluid path between the IC inlet port 108 and the IC outlet port 120 defines the IC portion 126 of the cell growth chamber 100. Fluid in a second circulation path flows in the cell growth chamber 100 through EC inlet port 128, comes in contact with the extracapillary side or outside (referred to as the "EC side" or "EC space" of the membrane) of the hollow fibers 116, and exits cell growth chamber 100 via EC outlet port 132. The fluid path between the EC inlet port 128 and the EC outlet port 132 comprises the EC portion 136 of the cell growth chamber 100. Fluid entering cell growth chamber 100 via the EC inlet port 128 may be in contact with the outside of the hollow fibers 116. Small molecules (e.g., ions, water, oxygen, lactate, etc.) may diffuse through the hollow fibers 116 from the interior or IC space of the hollow fiber to the exterior or EC space, or from the EC space to the IC space. Large molecular weight molecules, such as growth factors, are typically too large to pass through the hollow fiber membrane, and may remain in the IC space of the hollow fibers 116. The media may be replaced as needed, in embodiments. Media may also be circulated through an oxygenator or gas transfer module to exchange gasses as needed. Cells may be contained within a first circulation path and/or a second circulation path, as described below, and may be on either the IC side and/or EC side of the membrane, according to embodiments.

The material used to make the hollow fiber membrane 117 may be any biocompatible polymeric material which is capable of being made into hollow fibers. One material which may be used is a synthetic polysulfone-based material, according to an embodiment of the present disclosure. In order for the cells to adhere to the surface of the hollow fibers, the surface may be modified in some way, either by coating at least the cell growth surface with a protein such as fibronectin or collagen, for example, or by exposing the surface to radiation, according to embodiments. Gamma treating the membrane surface allows for attachment of adherent cells without additionally coating the membrane with fibronectin, cryoprecipitate, or the like. Bioreactors made of gamma treated membranes may be reused. Other coatings and/or treatments for cell attachment may be used in accordance with embodiments of the present disclosure.

Figure 1C:
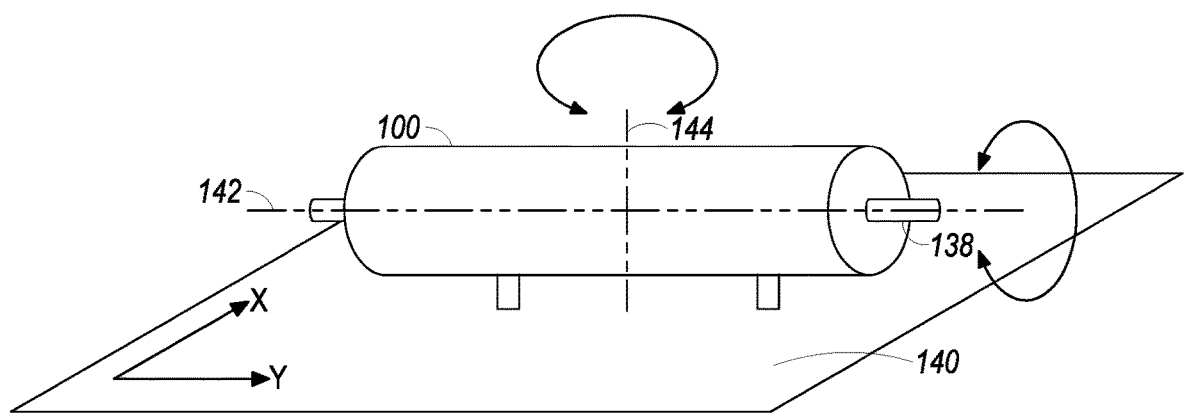
FIG. 1C depicts a rocking device for moving a cell growth chamber rotationally or laterally during operation of a cell expansion system, according to embodiments of the present disclosure.

In embodiments, the CES (such as CES 500 (see FIG. 5) and/or CES 600 (see FIG. 6), for example) may include a device configured to move or "rock" the cell growth chamber relative to other components of the cell expansion system by attaching it to a rotational and/or lateral rocking device. FIG. 1C shows one such device, in which a bioreactor 100 may be rotationally connected to two rotational rocking components and to a lateral rocking component, according to an embodiment.

A first rotational rocking component 138 rotates the bioreactor 100 around central axis 142 of the bioreactor 100. Rotational rocking component 138 may be rotationally associated with bioreactor 100. In embodiments, bioreactor 100 may be rotated continuously in a single direction around central axis 142 in a clockwise or counterclockwise direction. Alternatively, bioreactor 100 may rotate in alternating fashion, first clockwise, then counterclockwise, for example, around central axis 142, according to embodiments.

The CES may also include a second rotational rocking component that rotates bioreactor 100 around rotational axis 144. Rotational axis 144 may pass through the center point of bioreactor 100 and may be normal to central axis 142. Bioreactor 100 may be rotated continuously in a single direction around rotational axis 144 in a clockwise or counterclockwise direction, in embodiments. Alternatively, bioreactor 100 may be rotated around rotational axis 144 in an alternating fashion, first clockwise, then counterclockwise, for example. In various embodiments, bioreactor 100 may also be rotated around rotational axis 144 and positioned in a horizontal or vertical orientation relative to gravity.

In embodiments, lateral rocking component 140 may be laterally associated with bioreactor 100. The plane of lateral rocking component 140 moves laterally in the –x and –y directions, in embodiments. The settling of cells in the bioreactor may be reduced by movement of cell-containing media within the hollow fibers, according to embodiments.

The rotational and/or lateral movement of a rocking device may reduce the settling of cells within the device and reduce the likelihood of cells becoming trapped within a portion of the bioreactor. The rate of cells settling in the cell growth chamber is proportional to the density difference between the cells and the suspension media, according to Stoke's Law. In some embodiments, a 180 degree rotation (fast) with a pause (having a total combined time of 30 seconds, for example) repeated as described above keeps non-adherent red blood cells suspended. A minimum rotation of about 180 degrees would be preferred in an embodiment; however, one could use rotation of up to 360 degrees or greater. Different rocking components may be used separately, or may be combined in any combination. For example, a rocking component that rotates bioreactor 100 around central axis 142 may be combined with the rocking component that rotates bioreactor 100 around axis 144. Likewise, clockwise and counterclockwise rotation around different axes may be performed independently in any combination.

Figure 2:
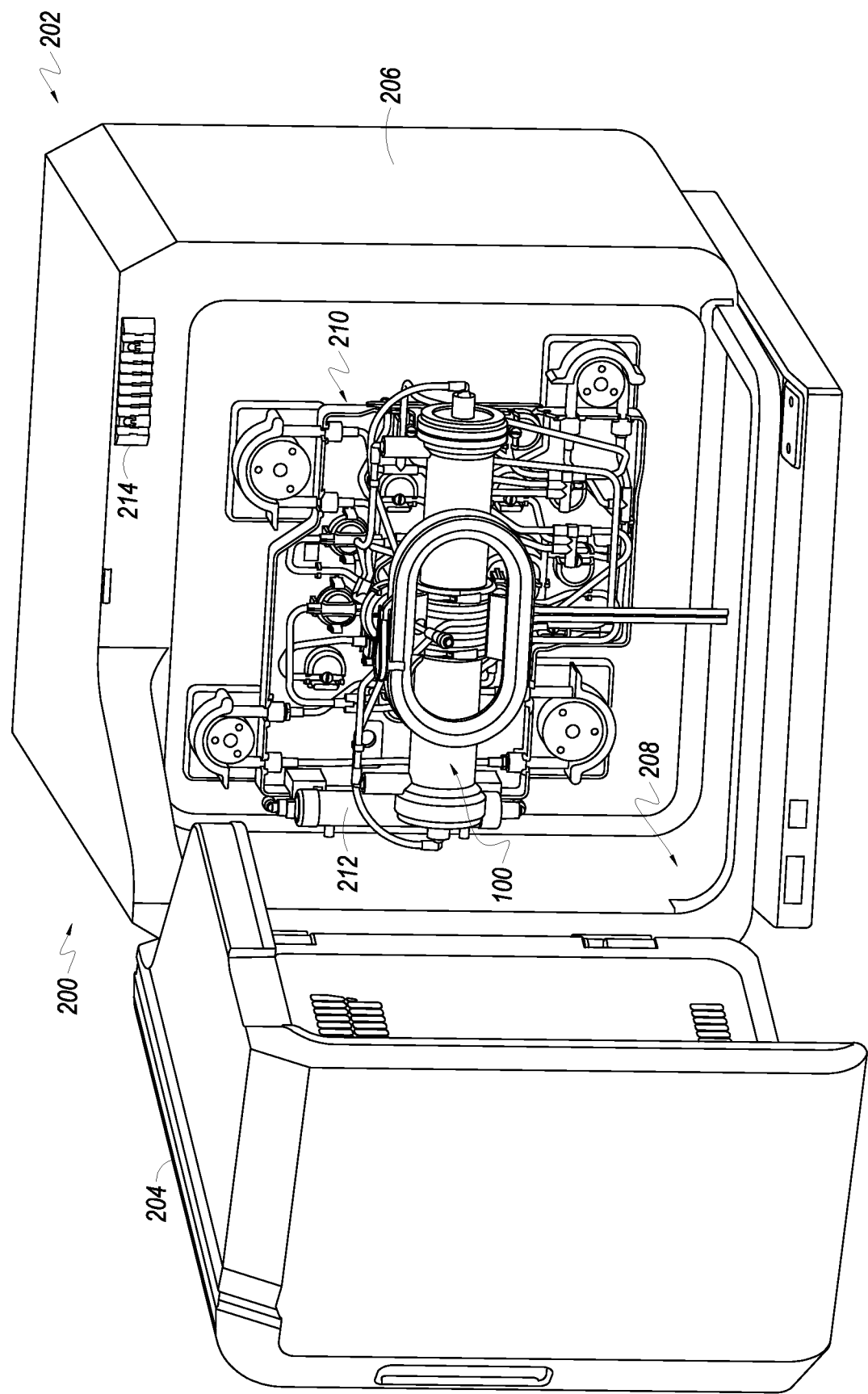
FIG. 2 illustrates a perspective view of a cell expansion system with a pre-mounted fluid conveyance device, in accordance with embodiments of the present disclosure.

Turning to FIG. 2, an embodiment of a cell expansion system 200 with a pre-mounted fluid conveyance assembly is shown in accordance with embodiments of the present disclosure. The CES 200 includes a cell expansion machine 202 that comprises a hatch or closable door 204 for engagement with a back portion 206 of the cell expansion machine 202. An interior space 208 within the cell expansion machine 202 includes features adapted for receiving and engaging a pre-mounted fluid conveyance assembly 210. The pre-mounted fluid conveyance assembly 210 is detachably-attachable to the cell expansion machine 202 to facilitate relatively quick exchange of a new or unused pre-mounted fluid conveyance assembly 210 at a cell expansion machine 202 for a used pre-mounted fluid conveyance assembly 210 at the same cell expansion machine 202. A single cell expansion machine 202 may be operated to grow or expand a first set of cells using a first pre-mounted fluid conveyance assembly 210 and, thereafter, may be used to grow or expand a second set of cells using a second pre-mounted fluid conveyance assembly 210 without needing to be sanitized between interchanging the first pre-mounted fluid conveyance assembly 210 for the second pre-mounted fluid conveyance assembly 210. The pre-mounted fluid conveyance assembly 210 includes a bioreactor 100 and an oxygenator or gas transfer module 212 (also see FIG. 4). Tubing guide slots are shown as 214 for receiving various media tubing connected to pre-mounted fluid conveyance assembly 210, according to embodiments.

Figure 3:
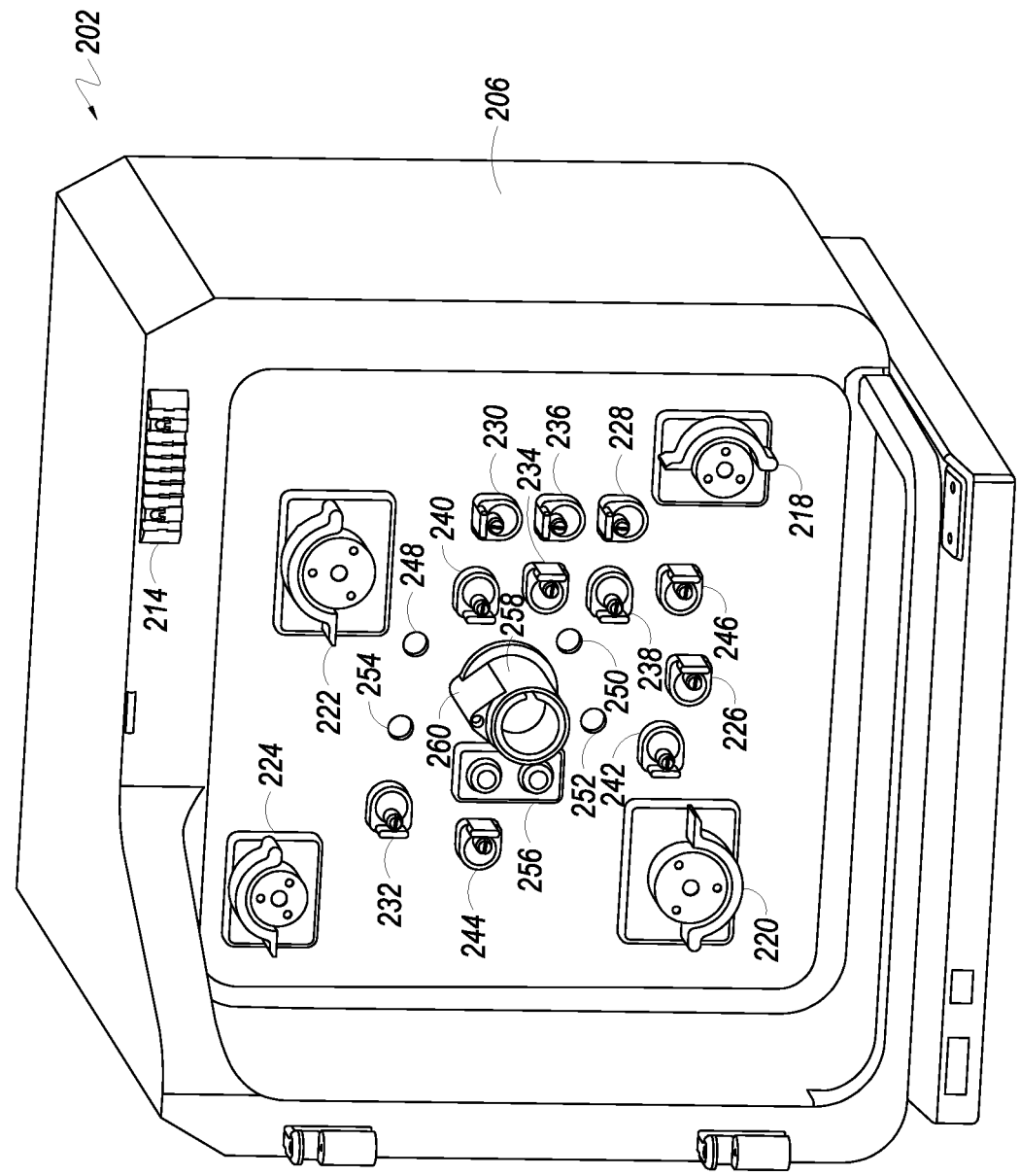
FIG. 3 depicts a perspective view of a housing of a cell expansion system, in accordance with embodiments of the present disclosure.

Next, FIG. 3 illustrates the back portion 206 of cell expansion machine 202 prior to detachably-attaching a pre-mounted fluid conveyance assembly 210 (FIG. 2), in accordance with embodiments of the present disclosure. The closable door 204 (shown in FIG. 2) is omitted from FIG. 3. The back portion 206 of the cell expansion machine 202 includes a number of different structures for working in combination with elements of a pre-mounted fluid conveyance assembly 210. More particularly, the back portion 206 of the cell expansion machine 202 includes a plurality of peristaltic pumps for cooperating with pump loops on the pre-mounted fluid conveyance assembly 210, including the IC circulation pump 218, the EC circulation pump 220, the IC inlet pump 222, and the EC inlet pump 224. In addition, the back portion 206 of the cell expansion machine 202 includes a plurality of valves, including the IC circulation valve 226, the reagent valve 228, the IC media valve 230, the air removal valve 232, the cell inlet valve 234, the wash valve 236, the distribution valve 238, the EC media valve 240, the IC waste or outlet valve 242, the EC waste or outlet valve 244, and the harvest valve 246. Several sensors are also associated with the back portion 206 of the cell expansion machine 202, including the IC outlet pressure sensor 248, the combination IC inlet pressure and temperature sensors 250, the combination EC inlet pressure and temperature sensors 252, and the EC outlet pressure sensor 254. Also shown is an optical sensor 256 for an air removal chamber, according to an embodiment.

In accordance with embodiments, a shaft or rocker control 258 for rotating the bioreactor 100 is shown. Shaft fitting 260 associated with the shaft or rocker control 258 allows for proper alignment of a shaft access aperture, see e.g., 424 (FIG. 4) of a tubing-organizer, see e.g., 300 (FIG. 4) of a pre-mounted conveyance assembly 210 or 400 with the back portion 206 of the cell expansion machine 202. Rotation of shaft or rocker control 258 imparts rotational movement to shaft fitting 260 and bioreactor 100. Thus, when an operator or user of the CES 200 attaches a new or unused pre-mounted fluid conveyance assembly 400 (FIG. 4) to the cell expansion machine 202, the alignment is a relatively simple matter of properly orienting the shaft access aperture 424 (FIG. 4) of the pre-mounted fluid conveyance assembly 210 or 400 with the shaft fitting 260.

Figure 4:
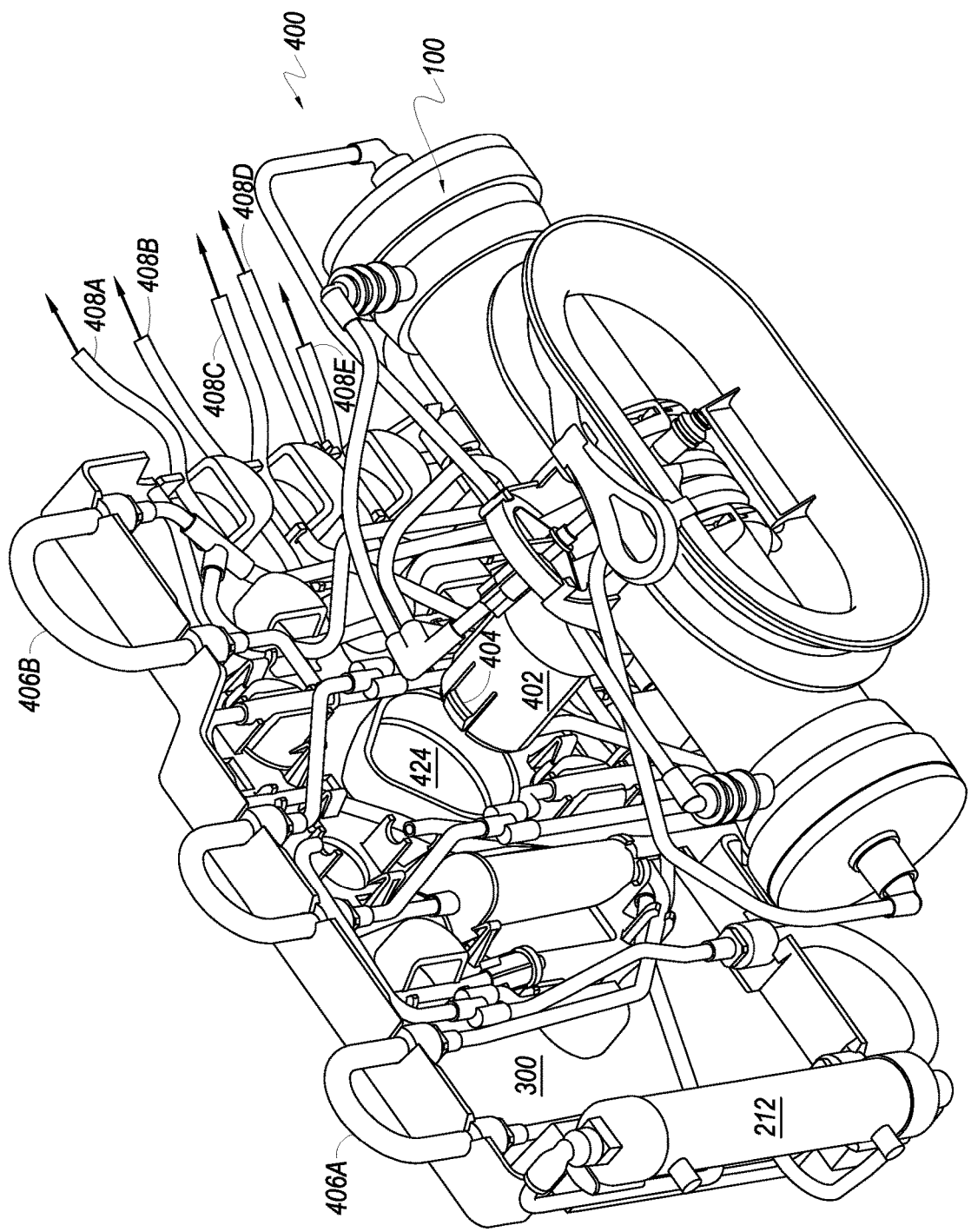
FIG. 4 illustrates a perspective view of a pre-mounted fluid conveyance device, in accordance with embodiments of the present disclosure

Turning to FIG. 4, a perspective view of a detachably-attachable pre-mounted fluid conveyance assembly 400 is shown. The pre-mounted fluid conveyance assembly 400 may be detachably-attachable to the cell expansion machine 202 (FIGS. 2 and 3) to facilitate relatively quick exchange of a new or unused pre-mounted fluid conveyance assembly 400 at a cell expansion machine 202 for a used pre-mounted fluid conveyance assembly 400 at the same cell expansion machine 202. As shown in FIG. 4, the bioreactor 100 may be attached to a bioreactor coupling that includes a shaft fitting 402. The shaft fitting 402 includes one or more shaft fastening mechanisms, such as a biased arm or spring member 404 for engaging a shaft, e.g., 258 (shown in FIG. 3), of the cell expansion machine 202.

According to embodiments, the pre-mounted fluid conveyance assembly 400 includes tubing 408A, 408B, 408C, 408D, 408E, etc., and various tubing fittings to provide the fluid paths shown in FIGS. 5 and 6, as described below. Pump loops 406A and 406B may also be provided for the pump(s). In embodiments, although the various media may be provided at the site where the cell expansion machine 202 is located, the pre-mounted fluid conveyance assembly 400 may include sufficient tubing length to extend to the exterior of the cell expansion machine 202 and to enable welded connections to tubing associated with media bag(s) or container(s), according to embodiments.

Figure 5:
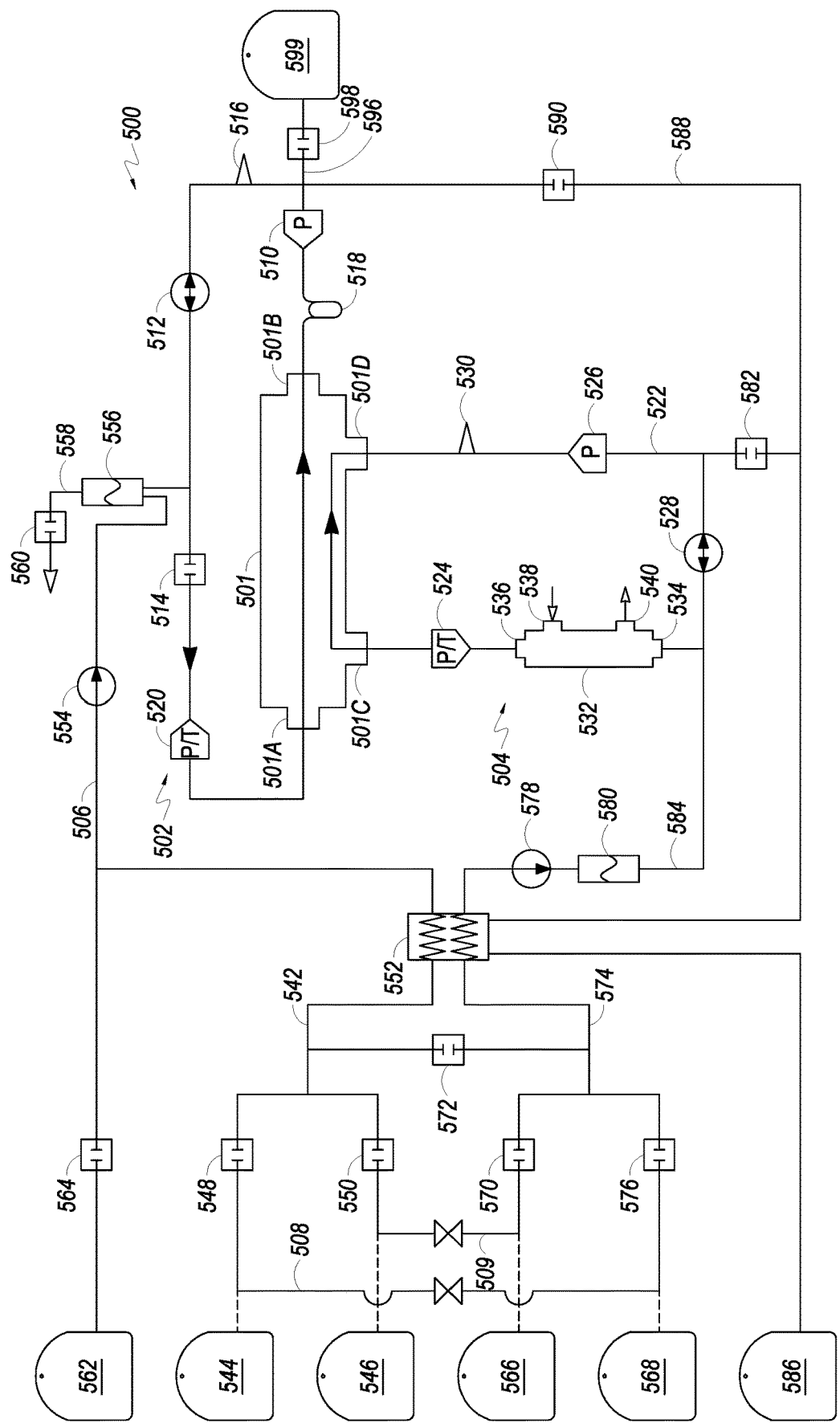
FIG. 5 depicts a schematic of a cell expansion system, in accordance with an embodiment of the present disclosure.
Figure 6:
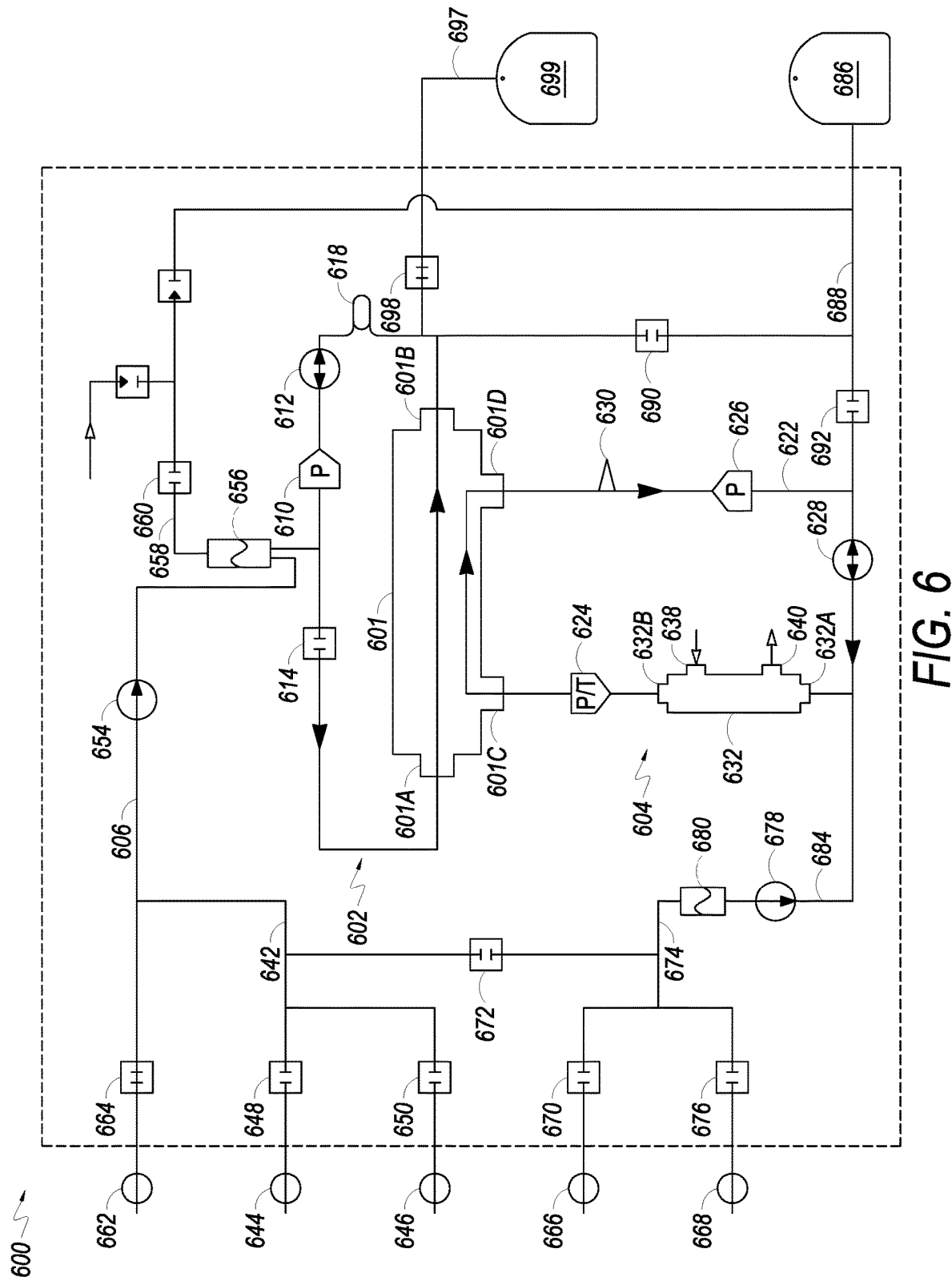
FIG. 6 illustrates a schematic of a cell expansion system, in accordance with another embodiment of the present disclosure.

Next, FIG. 5 illustrates a schematic of an embodiment of a cell expansion system 500, and FIG. 6 illustrates a schematic of another embodiment of a cell expansion system 600. In the embodiments shown in FIGS. 5 and 6, and as described below, the cells are grown in the IC space. However, the disclosure is not limited to such examples and may in other embodiments provide for cells to be grown in the EC space.

FIG. 5 illustrates a CES 500, which includes first fluid circulation path 502 (also referred to as the "intracapillary loop" or "IC loop") and second fluid circulation path 504 (also referred to as the "extracapillary loop" or "EC loop"), according to embodiments. First fluid flow path 506 may be fluidly associated with cell growth chamber 501 to form first fluid circulation path 502. Fluid flows into cell growth chamber 501 through IC inlet port 501A, through hollow fibers in cell growth chamber 501, and exits via IC outlet port 501B. Pressure gauge 510 measures the pressure of media leaving cell growth chamber 501. Media flows through IC circulation pump 512 which may be used to control the rate of media flow. IC circulation pump 512 may pump the fluid in a first direction or second direction opposite the first direction. Exit port 501B may be used as an inlet in the reverse direction. Media entering the IC loop may enter through valve 514. As those skilled in the art will appreciate, additional valves, pressure gauges, pressure/temperature sensors, ports, and/or other devices may be placed at various locations to isolate and/or measure characteristics of the media along portions of the fluid paths. Accordingly, it is to be understood that the schematic shown represents one possible configuration for various elements of the CES 500, and modifications to the schematic shown are within the scope of the one or more present embodiments.

With regard to the IC loop 502, samples of media may be obtained from sample port 516 or sample coil 518 during operation. Pressure/temperature gauge 520 disposed in first fluid circulation path 502 allows detection of media pressure and temperature during operation. Media then returns to IC inlet port 501A to complete fluid circulation path 502. Cells grown/expanded in cell growth chamber 501 may be flushed out of cell growth chamber 501 into harvest bag 599 through valve 598 or redistributed within the hollow fibers for further growth.

Fluid in second fluid circulation path 504 enters cell growth chamber 501 via EC inlet port 501C, and leaves cell growth chamber 501 via EC outlet port 501D. Media in the EC loop 504 may be in contact with the outside of the hollow fibers in the cell growth chamber 501, thereby allowing diffusion of small molecules into and out of the hollow fibers.

Pressure/temperature gauge 524 disposed in the second fluid circulation path 504 allows the pressure and temperature of media to be measured before the media enters the EC space of the cell growth chamber 501, according to an embodiment. Pressure gauge 526 allows the pressure of media in the second fluid circulation path 504 to be measured after it leaves the cell growth chamber 501. With regard to the EC loop, samples of media may be obtained from sample port 530 or a sample coil during operation.

In embodiments, after leaving EC outlet port 501D of cell growth chamber 501, fluid in second fluid circulation path 504 passes through EC circulation pump 528 to oxygenator or gas transfer module 532. EC circulation pump 528 may also pump the fluid in opposing directions. Second fluid flow path 522 may be fluidly associated with oxygenator or gas transfer module 532 via oxygenator inlet port 534 and oxygenator outlet port 536. In operation, fluid media flows into oxygenator or gas transfer module 532 via oxygenator inlet port 534, and exits oxygenator or gas transfer module 532 via oxygenator outlet port 536. Oxygenator or gas transfer module 532 adds oxygen to, and removes bubbles from, media in the CES 500, for example. In various embodiments, media in second fluid circulation path 504 may be in equilibrium with gas entering oxygenator or gas transfer module 532. The oxygenator or gas transfer module 532 may be any appropriately sized oxygenator or gas transfer device. Air or gas flows into oxygenator or gas transfer module 532 via filter 538 and out of oxygenator or gas transfer device 532 through filter 540. Filters 538 and 540 reduce or prevent contamination of oxygenator or gas transfer module 532 and associated media. Air or gas purged from the CES 500 during portions of a priming sequence may vent to the atmosphere via the oxygenator or gas transfer module 532.

In the configuration depicted for CES 500, fluid media in first fluid circulation path 502 and second fluid circulation path 504 flows through cell growth chamber 501 in the same direction (a co-current configuration). The CES 500 may also be configured to flow in a counter-current conformation.

In accordance with at least one embodiment, media, including cells (from bag 562), and fluid media from bag 546 may be introduced to first fluid circulation path 502 via first fluid flow path 506. Fluid container 562 (e.g., Cell Inlet Bag or Saline Priming Fluid for priming air out of the system) may be fluidly associated with the first fluid flow path 506 and the first fluid circulation path 502 via valve 564.

Fluid containers, or media bags, 544 (e.g., Reagent) and 546 (e.g., IC Media) may be fluidly associated with either first fluid inlet path 542 via valves 548 and 550, respectively, or second fluid inlet path 574 via valves 570 and 576. First and second sterile sealable input priming paths 508 and 509 are also provided. An air removal chamber (ARC) 556 may be fluidly associated with first circulation path 502. The air removal chamber 556 may include one or more ultrasonic sensors including an upper sensor and lower sensor to detect air, a lack of fluid, and/or a gas/fluid interface, e.g., an air/fluid interface, at certain measuring positions within the air removal chamber 556. For example, ultrasonic sensors may be used near the bottom and/or near the top of the air removal chamber 556 to detect air, fluid, and/or an air/fluid interface at these locations. Embodiments provide for the use of numerous other types of sensors without departing from the spirit and scope of the present disclosure. For example, optical sensors may be used in accordance with embodiments of the present disclosure. Air or gas purged from the CES 500 during portions of the priming sequence or other protocols may vent to the atmosphere out air valve 560 via line 558 that may be fluidly associated with air removal chamber 556.

EC media (e.g., from bag 568) or wash solution (e.g., from bag 566) may be added to either the first or second fluid flow paths. Fluid container 566 may be fluidly associated with valve 570 that may be fluidly associated with first fluid circulation path 502 via distribution valve 572 and first fluid inlet path 542. Alternatively, fluid container 566 may be fluidly associated with second fluid circulation path 504 via second fluid inlet path 574 and EC inlet path 584 by opening valve 570 and closing distribution valve 572. Likewise, fluid container 568 may be fluidly associated with valve 576 that may be fluidly associated with first fluid circulation path 502 via first fluid inlet path 542 and distribution valve 572. Alternatively, fluid container 568 may be fluidly associated with second fluid inlet path 574 by opening valve 576 and closing distribution valve 572.

An optional heat exchanger 552 may be provided for media reagent or wash solution introduction.

In the IC loop, fluid may be initially advanced by the IC inlet pump 554. In the EC loop, fluid may be initially advanced by the EC inlet pump 578. An air detector 580, such as an ultrasonic sensor, may also be associated with the EC inlet path 584.

In at least one embodiment, first and second fluid circulation paths 502 and 504 are connected to waste or outlet line 588. When valve 590 is opened, IC media may flow through waste line 588 and to waste or outlet bag 586. Likewise, when valve 582 is opened, EC media may flow through waste line 588 to waste or outlet bag 586.

In embodiments, cells may be harvested via cell harvest path 596. Here, cells from cell growth chamber 501 may be harvested by pumping the IC media containing the cells through cell harvest path 596 and valve 598 to cell harvest bag 599.

Various components of the CES 500 may be contained or housed within a machine or housing, such as cell expansion machine 202 (FIGS. 2 and 3), wherein the machine maintains cells and media, for example, at a predetermined temperature.

Turning to FIG. 6, a schematic of another embodiment of a cell expansion system 600 is shown. CES 600 includes a first fluid circulation path 602 (also referred to as the "intracapillary loop" or "IC loop") and second fluid circulation path 604 (also referred to as the "extracapillary loop" or "EC loop"). First fluid flow path 606 may be fluidly associated with cell growth chamber 601 to form first fluid circulation path 602. Fluid flows into cell growth chamber 601 through IC inlet port 601A, through hollow fibers in cell growth chamber 601, and exits via IC outlet port 601B. Pressure sensor 610 measures the pressure of media leaving cell growth chamber 601. In addition to pressure, sensor 610 may, in embodiments, also be a temperature sensor that detects the media pressure and temperature during operation. Media flows through IC circulation pump 612 which may be used to control the rate of media flow. IC circulation pump 612 may pump the fluid in a first direction or second direction opposite the first direction. Exit port 601B may be used as an inlet in the reverse direction. Media entering the IC loop may enter through valve 614. As those skilled in the art will appreciate, additional valves, pressure gauges, pressure/temperature sensors, ports, and/or other devices may be placed at various locations to isolate and/or measure characteristics of the media along portions of the fluid paths. Accordingly, it is to be understood that the schematic shown represents one possible configuration for various elements of the CES 600, and modifications to the schematic shown are within the scope of the one or more present embodiments.

With regard to the IC loop, samples of media may be obtained from sample coil 618 during operation. Media then returns to IC inlet port 601A to complete fluid circulation path 602. Cells grown/expanded in cell growth chamber 601 may be flushed out of cell growth chamber 601 into harvest bag 699 through valve 698 and line 697. Alternatively, when valve 698 is closed, the cells may be redistributed within chamber 601 for further growth.

Fluid in second fluid circulation path 604 enters cell growth chamber 601 via EC inlet port 601C and leaves cell growth chamber 601 via EC outlet port 601D. Media in the EC loop may be in contact with the outside of the hollow fibers in the cell growth chamber 601, thereby allowing diffusion of small molecules into and out of the hollow fibers that may be within chamber 601, according to an embodiment.

Pressure/temperature sensor 624 disposed in the second fluid circulation path 604 allows the pressure and temperature of media to be measured before the media enters the EC space of the cell growth chamber 601. Sensor 626 allows the pressure and/or temperature of media in the second fluid circulation path 604 to be measured after it leaves the cell growth chamber 601. With regard to the EC loop, samples of media may be obtained from sample port 630 or a sample coil during operation.

After leaving EC outlet port 601D of cell growth chamber 601, fluid in second fluid circulation path 604 passes through EC circulation pump 628 to oxygenator or gas transfer module 632. EC circulation pump 628 may also pump the fluid in opposing directions, according to embodiments. Second fluid flow path 622 may be fluidly associated with oxygenator or gas transfer module 632 via an inlet port 632A and an outlet port 632B of oxygenator or gas transfer module 632. In operation, fluid media flows into oxygenator or gas transfer module 632 via inlet port 632A, and exits oxygenator or gas transfer module 632 via outlet port 632B. Oxygenator or gas transfer module 632 adds oxygen to, and removes bubbles from, media in the CES 600, for example. In various embodiments, media in second fluid circulation path 604 may be in equilibrium with gas entering oxygenator or gas transfer module 632. The oxygenator or gas transfer module 632 may be any appropriately sized device useful for oxygenation or gas transfer. Air or gas flows into oxygenator or gas transfer module 632 via filter 638 and out of oxygenator or gas transfer device 632 through filter 640. Filters 638 and 640 reduce or prevent contamination of oxygenator or gas transfer module 632 and associated media. Air or gas purged from the CES 600 during portions of a priming sequence may vent to the atmosphere via the oxygenator or gas transfer module 632.

In the configuration depicted for CES 600, fluid media in first fluid circulation path 602 and second fluid circulation path 604 flows through cell growth chamber 601 in the same direction (a co-current configuration). The CES 600 may also be configured to flow in a counter-current conformation, according to embodiments.

In accordance with at least one embodiment, media, including cells (from a source such as a cell container, e.g., a bag) may be attached at attachment point 662, and fluid media from a media source may be attached at attachment point 646. The cells and media may be introduced into first fluid circulation path 602 via first fluid flow path 606. Attachment point 662 may be fluidly associated with the first fluid flow path 606 via valve 664, and attachment point 646 may be fluidly associated with the first fluid flow path 606 via valve 650. A reagent source may be fluidly connected to point 644 and be associated with fluid inlet path 642 via valve 648, or second fluid inlet path 674 via valves 648 and 672.

Air removal chamber (ARC) 656 may be fluidly associated with first circulation path 602. The air removal chamber 656 may include one or more sensors including an upper sensor and lower sensor to detect air, a lack of fluid, and/or a gas/fluid interface, e.g., an air/fluid interface, at certain measuring positions within the air removal chamber 656. For example, ultrasonic sensors may be used near the bottom and/or near the top of the air removal chamber 656 to detect air, fluid, and/or an air/fluid interface at these locations. Embodiments provide for the use of numerous other types of sensors without departing from the spirit and scope of the present disclosure. For example, optical sensors may be used in accordance with embodiments of the present disclosure. Air or gas purged from the CES 600 during portions of a priming sequence or other protocol(s) may vent to the atmosphere out air valve 660 via line 658 that may be fluidly associated with air removal chamber 656.

An EC media source may be attached to EC media attachment point 668, and a wash solution source may be attached to wash solution attachment point 666, to add EC media and/or wash solution to either the first or second fluid flow path. Attachment point 666 may be fluidly associated with valve 670 that may be fluidly associated with first fluid circulation path 602 via valve 672 and first fluid inlet path 642. Alternatively, attachment point 666 may be fluidly associated with second fluid circulation path 604 via second fluid inlet path 674 and second fluid flow path 684 by opening valve 670 and closing valve 672. Likewise, attachment point 668 may be fluidly associated with valve 676 that may be fluidly associated with first fluid circulation path 602 via first fluid inlet path 642 and valve 672. Alternatively, fluid container 668 may be fluidly associated with second fluid inlet path 674 by opening valve 676 and closing distribution valve 672.

In the IC loop, fluid may be initially advanced by the IC inlet pump 654. In the EC loop, fluid may be initially advanced by the EC inlet pump 678. An air detector 680, such as an ultrasonic sensor, may also be associated with the EC inlet path 684.

In at least one embodiment, first and second fluid circulation paths 602 and 604 are connected to waste or outlet line 688. When valve 690 is opened, IC media may flow through waste line 688 and to waste or outlet bag 686. Likewise, when valve 692 is opened, EC media may flow to waste or outlet bag 686.

After cells have been grown in cell growth chamber 601, they may be harvested via cell harvest path 697. Here, cells from cell growth chamber 601 may be harvested by pumping the IC media containing the cells through cell harvest path 697, with valve 698 open, into cell harvest bag 699.

Various components of the CES 600 may be contained or housed within a machine or housing, such as cell expansion machine 202 (FIGS. 2 and 3), wherein the machine maintains cells and media, for example, at a predetermined temperature. It is further noted that, in embodiments, components of CES 600 and CES 500 (FIG. 5) may be combined. In other embodiments, a CES may include fewer or additional components than those shown in FIGS. 5 and 6 and still be within the scope of the present disclosure. An example of a cell expansion system that may incorporate features of the present disclosure is the Quantum® Cell Expansion System (the "Quantum® System"), manufactured by Terumo BCT, Inc. in Lakewood, Colo.

Examples and further description of cell expansion systems are provided in U.S. patent application Ser. No. 12/042,798 (U.S. Pat. No. 8,309,347), entitled, "Cell Expansion System and Methods of Use," issued on Nov. 13, 2012, which is hereby incorporated by reference herein in its entirety for all that it teaches and for all purposes.

Figure 7:
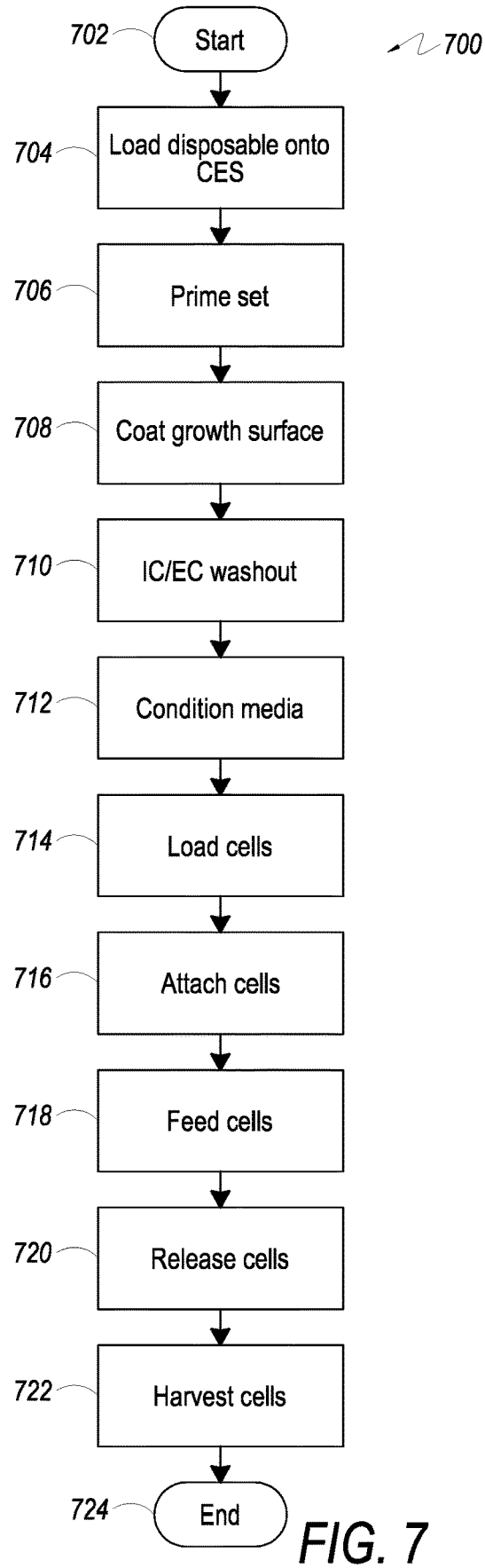
FIG. 7 depicts a flow diagram illustrating the operational characteristics of a process for applying an agent to a cell growth surface in accordance with embodiments of the present disclosure.

While various example embodiments of a cell expansion system and methods associated therewith have been described, FIG. 7 illustrates example operational steps 700 of a process for applying an agent to a cell growth surface that may be used with a cell expansion system, such as CES 500 (FIG. 5) or CES 600 (FIG. 6), in accordance with embodiments of the present disclosure. FIG. 7 will be described in conjunction with example settings and media introduction. However, the embodiments presented herein are not limited to this example; rather, the embodiments can be modified to meet other system designs or configurations. START operation is initiated 702, and process 700 proceeds to load the disposable tubing set 704 onto the cell expansion system. Next, the system may be primed 706. In an embodiment, a user or an operator, for example, may provide an instruction to the system to prime by selecting a task for priming, for example. In an embodiment, such task for priming may be a pre-programmed task. The system 500 (FIG. 5) or 600 (FIG. 6) may be primed, for example, with phosphate-buffered saline (PBS). To prime the bioreactor 501, 601, a bag (e.g., 546) may be attached (for example, to connection point 646) to the system 500, 600. When referring to numerals in the Figures, for example, such as "Numeral, Numeral" (e.g., 500, 600), such nomenclature can mean "Numeral and/or Numeral" (e.g., 500 and/or 600). Valve 550, 650 may be opened. The PBS can then be directed into the first fluid circulation path 502, 602 by the IC inlet pump 554, 654 set to pump the PBS into the first fluid circulation path 502, 602. Valve 514, 614 may be opened while the PBS enters the bioreactor 501, 601 through the inlet 501A, 601A and out the outlet 501B, 601B. Once the bioreactor 501, 601 and/or the first fluid circulation path 502, 602 have media therein with air removed by the air removal chamber 556, 656, the bioreactor 501, 601 is primed, according to an embodiment.

In an embodiment, to further prime the bioreactor 501, 601, a bag (e.g., 568) may be attached (for example, to connection point 668) to the system 500, 600. Valve 576, 676 may be opened. A media, e.g., PBS, can then be directed into the second fluid circulation path 504, 604 by the EC inlet pump 578, 678 set to pump the media into the second fluid circulation path 504, 604. Valve 582, 692 may be closed while the media enters the bioreactor 501, 601 through the inlet 501C, 601C and out the outlet 501D, 601D of the EC loop. Once the bioreactor 501, 601 and/or the second fluid circulation path 504, 604 have media therein with air removed, e.g., by an air removal chamber, the bioreactor 501, 601 is primed, according to an embodiment.

Process 700 then proceeds to coat the cell growth surface, e.g., bioreactor 501, 601, in step 708, in which the cell growth surface may be coated with a coating agent or reagent. Any coating agent(s) or reagent(s), such as fibronectin or cryoprecipitate, for example, understood by those of skill in the art may be used. In embodiments, any combination of coating agent(s) or reagent(s) may be used. In an embodiment, an outlet or waste valve 590, 690 to one of the circulation loops, e.g., IC loop 502, 602, may be closed, while the outlet or waste valve 582, 692 to the other circulation loop, e.g., EC loop 504, 604, may be opened or remains open. For example, the IC waste or outlet valve 590, 690 may be closed while the EC waste or outlet valve 582, 692 is open. In embodiments, a coating agent or reagent may be loaded into a circulation loop, e.g., IC loop 502, 602, of the cell expansion system 500, 600 until the reagent bag (e.g., 544) or container is empty. Next, the reagent may be chased from an air removal chamber 556, 656 into the circulation loop, e.g., IC loop 502, 602. The bioreactor 501, 601, e.g., cell growth surface of hollow fibers where a hollow fiber bioreactor is used, may then be coated by controlling the fluid movement in the bioreactor 501, 601. In embodiments, such control of the fluid movement uses ultrafiltration, e.g., positive ultrafiltration, to move fluid from one side (e.g., the IC side 502, 602) of the bioreactor 501, 601 to the other side (e.g., the EC side 504, 604). For example, where the IC outlet or waste valve 590, 690 may be closed, with the EC outlet or waste valve open 582, 692, a fluid in the bioreactor 501, 601 may have no pathway but through the pores of the fibers (IC outlet valve 590, 690 closed). In an embodiment, the IC inlet rate may be set to wash the IC side 502, 602 with media or a fluid, such as phosphate buffered saline (PBS), for example. Accordingly, the solution may then flow through the pores of the fibers from the IC side 502, 602 to the EC side 504, 604. The coating agent, e.g., CPPT, may be hydrostatically deposited onto the wall(s), e.g., inner wall(s), of the bioreactor fiber for a defined time period. For example, such time period may be about ten (10) minutes, according to an embodiment. Other time periods may apply according to other embodiments of the present disclosure. Such membrane ultrafiltration method allows adherence promoting proteins to be physisorbed on the bioreactor fibers as the solution flows through the pores of the fiber from the IC side 502, 602 to the EC side 504, 604.

An example of the solutions being introduced to the system 500, 600 to coat the bioreactor may be as shown below:

TABLE 1

| Bag (Connection Point) | Solution in Bag | Volume (estimation based on factory default values) |
| --- | --- | --- |
| Cell Inlet 562 (662) | None | N/A |
| Reagent 544 (644) | Reagent (e.g., CPPT or Fibronectin) | e.g., 6-25 mL CPPT in 100 mL total volume w/PBS |
| IC Media 546 (646) | None | N/A |
| Wash 566 (666) | PBS | 1 L |
| EC Media 568 (668) | None | N/A |

The coating of the bioreactor may occur in three stages. An example of the settings for the system 500, 600 for the first stage of introducing the solution(s) above may be as shown below:

TABLE 2

| Component | Setting |
| --- | --- |
| IC Inlet valve configuration | Reagent (e.g., valves 548, 648, 514, 614 open) |
| IC Inlet Rate for Pump 554, 654 | 10 mL/min |
| IC Circulation Rate for Pump 512, 612 | 100 mL/min |
| EC Inlet valve configuration | None |
| EC Inlet Rate for Pump 578, 678 | 0 mL/min |
| EC Circulation Rate for Pump 528, 628 | 30 mL/min |
| Outlet valve configuration | EC Outlet (e.g., valve 582, 692 open) |
| Rocker Control | Stationary (0°) |
| Stop Condition | Empty Bag for bag 544 |

An example of the settings for the system 500, 600 for the second stage of coating the bioreactor, which chases or washes reagent from the air removal chamber 556, 656, may be as shown below:

TABLE 3

| Component | Setting |
| --- | --- |
| IC Inlet valve configuration | Wash (e.g., valves 570, 670, 572, 672, 514, 614, 560, 660 open) |
| IC Inlet Rate for Pump 554, 654 | 10 mL/min |
| IC Circulation Rate for Pump 512, 612 | 100 mL/min |
| EC Inlet valve configuration | None |
| EC Inlet Rate for Pump 578, 678 | 0 mL/min |

TABLE 3-continued

| Component | Setting |
|---|---|
| EC Circulation Rate for Pump 528, 628 | 30 mL/min |
| Outlet valve configuration | EC Outlet (e.g., valve 582, 692 open) |
| Rocker Control | Stationary (0°) |
| Stop Condition | IC Volume (e.g., 22 mL) |

An example of the settings for the system 500, 600 for the third stage of coating the bioreactor, which causes ultrafiltration from the IC side 502, 602 to the EC side 504, 604, for example, may be as shown below:

TABLE 4

| Component | Setting |
|---|---|
| IC Inlet valve configuration | Wash (e.g., valves 570, 670, 572, 672, 514, 614 open) |
| IC Inlet Rate for Pump 554, 654 | 50 mL/min |
| IC Circulation Rate for Pump 512, 612 | −25 mL/min |
| EC Inlet valve configuration | Wash |
| EC Inlet Rate for Pump 578, 678 | 0.1 mL/min |
| EC Circulation Rate for Pump 528, 628 | 30 mL/min |
| Outlet valve configuration | EC Outlet (e.g., valve 582, 692 open) |
| Rocker Control | Stationary (0°) |
| Stop Condition | 10 Min |

In an embodiment, such active promoting of the coating agent to a cell growth surface, as described above, may significantly decrease the amount of time to coat the cell growth surface as compared to other methods of coating a cell growth surface. In embodiments, such coating procedure using ultrafiltration may be referred to as an expedited coating procedure. Such expedited coating procedure using active moving of the coating agent to the cell growth surface(s) through ultrafiltration may use less time to coat the cell growth surface than procedures using passive coating procedures which may take overnight or about twelve (12) hours to about sixteen (16) hours to coat the bioreactor. For example, such expedited coating procedure may take less than or equal to about four (4) hours. In embodiments, such expedited coating procedure may take any time period in a range from above or equal to about five (5) minutes to less than or equal to about sixty (60) minutes, or any other range therein, depending on the procedure. For example, such coating procedure may take less than or equal to about ten (10) minutes, less than or equal to about twelve (12) minutes, less than or equal to about fifteen (15) minutes, less than or equal to about twenty (20) minutes, less than or equal to about thirty (30) minutes, less than or equal to about forty-five (45) minutes, less than or equal to about sixty (60) minutes, etc. As described above, passive coating procedures may take about sixteen (16) hours to coat the bioreactor, for example. A significant time savings may be realized by using ultrafiltration for coating the bioreactor.

Returning to FIG. 7, once the bioreactor is coated, the IC/EC Washout task may be performed in step 710, in which fluid on the IC circulation loop 502, 602 and on the EC circulation loop 504, 604 may be replaced. The replacement volume may be determined by the number of IC Volumes and EC Volumes exchanged. An example of the solutions being introduced to the system 500, 600 during the IC/EC Washout task may be as shown below:

TABLE 5

| Bag (Connection Point) | Solution in Bag | Volume (estimation based on factory default values) |
|---|---|---|
| Cell Inlet 562 (662) | None | N/A |
| Reagent 544 (644) | None | N/A |
| IC Media 546 (646) | Media with Protein | 1.4 L |
| Wash 566 (666) | None | N/A |
| EC Media 568 (668) | None | N/A |

An example of the settings for an IC/EC Washout task of the system 500, 600 may be as shown below:

TABLE 6

| Component | Setting |
|---|---|
| IC Inlet valve configuration | IC Media (e.g., valves 550, 650, 514, 614 open) |
| IC Inlet Rate for Pump 554, 654 | 100 mL/min |
| IC Circulation Rate for Pump 512, 612 | −17 mL/min |
| EC Inlet valve configuration | IC Media (e.g., valves 550, 650, 572, 672 open) |
| EC Inlet Rate for Pump 578, 678 | 148 mL/min |
| EC Circulation Rate for Pump 528, 628 | −1.7 mL/min |
| Outlet valve configuration | IC and EC Outlet (e.g., valves 590, 690 and 582, 692 open) |
| Rocker Control | In Motion (−90°, 180°, in 1 sec intervals) |
| Stop Condition | Exchange (2.5 IC Volumes; 2.5 EC Volumes) |

Next, to maintain the proper or desired gas concentration across the fibers in the bioreactor membrane, the condition media task 712 may be executed to allow the media to reach equilibrium with the provided gas supply before cells are loaded into the bioreactor. For example, rapid contact between the media and the gas supply provided by the gas transfer module or oxygenator 532, 632 may be provided by using a high EC circulation rate. The system 500, 600 may then be maintained in a proper or desired state until a user or operator, for example, is ready to load cells into the bioreactor 501, 601. In an embodiment, the system 500, 600 may be conditioned with complete media, for example. Complete media may be any media source used for cell growth. In an embodiment, complete media may comprise alpha-MEM (α-MEM) and fetal bovine serum (FBS), for example. Any type of media known to those of skill in the art may be used.

The condition media task 712 may be a two-step process where, in the first step, the system 500, 600 provides rapid contact between the media and the gas supply by using a high EC circulation rate.

In the second step, the system 500, 600 maintains the bioreactor 501, 601 in a proper state until an operator, for example, is ready to load the cells. An example of the solutions being introduced to the system 500, 600 during the condition media task 712 may be as shown below.

While an example media is shown in Table 7, any type of media known to those of skill in the art may be used.

TABLE 7

| Bag (Connection Point) | Solution in Bag | Volume (estimation based on factory default values) |
|---|---|---|
| Cell Inlet 562 (662) | None | N/A |
| Reagent 544 (644) | None | N/A |

TABLE 7-continued

| Bag (Connection Point) | Solution in Bag | Volume (estimation based on factory default values) |
|---|---|---|
| IC Media 546 (646) | None | N/A |
| Wash 566 (666) | None | N/A |
| EC Media 568 (668) | Media with Protein (e.g., αMEM with GlutaMAX plus 10% FBS) | 0.1 L plus 6 mL/hour |

An example of the settings for a first step of the condition media task 712 may be as shown below:

TABLE 8

| Component | Setting |
|---|---|
| IC Inlet valve configuration | None |
| IC Inlet Rate for Pump 554, 654 | 0 mL/min |
| IC Circulation Rate for Pump 512, 612 | 100 mL/min |
| EC Inlet valve configuration | EC Media (and/or IC Media) (e.g., valve 576, 676 open) |
| EC Inlet Rate for Pump 578, 678 | 0.1 mL/min |
| EC Circulation Rate for Pump 528, 628 | 250 mL/min |
| Outlet valve configuration | EC Outlet (e.g., valve 582, 692 open) |
| Rocker Control | Stationary |
| Stop Condition | Time (e.g., 10 min) |

An example of the settings for a second step of the condition media task 712 may be as shown below:

TABLE 9

| Component | Setting |
|---|---|
| IC Inlet valve configuration | None |
| IC Inlet Rate for Pump 554, 654 | 0 mL/min |
| IC Circulation Rate for Pump 512, 612 | 100 mL/min |
| EC Inlet valve configuration | EC Media (and/or IC Media) (e.g., valve 576, 676 open) |
| EC Inlet Rate for Pump 578, 678 | 0.1 mL/min |
| EC Circulation Rate for Pump 528, 628 | 30 mL/min |
| Outlet valve configuration | EC Outlet (e.g., valve 582, 692 open) |
| Rocker Control | Stationary |
| Stop Condition | Manual |

Process 700 next proceeds to loading cells 714 into the bioreactor 501, 601 from a cell inlet bag 562 (at connection point 662), for example. In an embodiment, the cells are loaded with uniform suspension 714. In an embodiment, the cells may be loaded into the bioreactor 501, 601 from the cell inlet bag 562 (at connection point 662) until the bag 562 is empty. Cells may then be chased or washed from the air removal chamber 556, 656 to the bioreactor 501, 601, according to an embodiment. In embodiments that utilize larger chase volumes, cells may be spread and move toward the IC outlet port 501B, 601B. The distribution of cells may be promoted across the membrane via IC circulation, such as through an IC circulation pump 512, 612, with no IC inlet, for example. Examples and further description of loading and distributing cells are provided in U.S. patent application Ser. No. 13/971,500 (U.S. Pat. No. 9,175,259), entitled, "Method of Loading and Distributing Cells in a Bioreactor of a Cell Expansion System," issued Nov. 3, 2015, which is hereby incorporated by reference herein in its entirety for all that it teaches and for all purposes.

In another embodiment, the cells may be loaded 714 using another type of cell loading, such as a high flux cell load. In yet another embodiment, the cells may be loaded 714 using another type of loading, such as a bulls-eye cell loading technique. Examples and further description of bulls-eye cell loading procedure(s) are provided in U.S. patent application Ser. No. 14/542,276 (U.S. Pat. No. 9,617,506), entitled, "Expanding Cells in a Bioreactor," issued on Apr. 11, 2017, which is hereby incorporated by reference herein in its entirety for all that it teaches and for all purposes.

An example of the solutions being introduced to the system 500, 600 to load cells 714 may be as shown below:

TABLE 10

| Bag (Connection Point) | Solution in Bag | Volume (estimation based on factory default values) |
|---|---|---|
| Cell Inlet 562 (662) | Cells | Cells (e.g., mesenchymal stem cells (MSC)) in 100 mL complete media |
| Reagent 544 (644) | None | N/A |
| IC Media 546 (646) | Media with Protein | 0.1 L |
| Wash 566 (666) | None | N/A |
| EC Media 568 (668) | None | N/A |

The loading of cells 714 may occur in stages. An example of the settings for the system 500, 600 for an example first stage may be as shown below:

TABLE 11

| Component | Setting |
|---|---|
| IC Inlet valve configuration | Cell Inlet (e.g., valves 564, 664, 514, 614 open) |
| IC Inlet Rate for Pump 554, 654 | 50 mL/min |
| IC Circulation Rate for Pump 512, 612 | 200 mL/min |
| EC Inlet valve configuration | None |
| EC Inlet Rate for Pump 578, 678 | 0 mL/min |
| EC Circulation Rate for Pump 528, 628 | 30 mL/min |
| Outlet valve configuration | EC Outlet (e.g., valve 582, 692 open) |
| Rocker Control | In Motion (−90°, 180°, in 1 sec intervals) |
| Stop Condition | ARC stop |

An example of the settings for the system 500, 600 for an example second stage may be as shown below:

TABLE 12

| Component | Setting |
|---|---|
| IC Inlet valve configuration | IC Media (e.g., valves 550, 650, 514, 614 open) |
| IC Inlet Rate for Pump 554, 654 | 50 mL/min |
| IC Circulation Rate for Pump 512, 612 | 200 mL/min |
| EC Inlet valve configuration | None |
| EC Inlet Rate for Pump 578, 678 | 0 mL/min |
| EC Circulation Rate for Pump 528, 628 | 30 mL/min |
| Outlet valve configuration | EC Outlet (e.g., valve 582, 692 open) |
| Rocker Control | In Motion (−90°, 180°, in 1 sec intervals) |
| Stop Condition | IC Volume (e.g., 22 mL) |

An example of the settings for the system 500, 600 for an example third stage may be as shown below:

TABLE 13

| Component | Setting |
| --- | --- |
| IC Inlet valve configuration | None |
| IC Inlet Rate for Pump 554, 654 | 0 mL/min |
| IC Circulation Rate for Pump 512, 612 | 200 mL/min |
| EC Inlet valve configuration | None |
| EC Inlet Rate for Pump 578, 678 | 0 mL/min |
| EC Circulation Rate for Pump 528, 628 | 30 mL/min |
| Outlet valve configuration | EC Outlet (e.g., valve 582, 692 open) |
| Rocker Control | In Motion (−90°, 180°, in 1 sec intervals) |
| Stop Condition | Time (2.0 Min) |

Further, the cells, e.g., adherent cells, may be allowed to attach 716 to the hollow fibers. In an embodiment, in allowing the cells to attach 716, adherent cells are enabled to attach to the bioreactor membrane while allowing flow on the EC circulation loop 504, 604, with the pump (e.g., 512, 612, 554, 654) flow rate to the IC loop 502, 602 set to zero. An example of the solutions being introduced to the system 500, 600 during the process of cells attaching to the membrane 716 may be as shown below:

TABLE 14

| Bag (Connection Point) | Solution in Bag | Volume (estimation based on factory default values) |
| --- | --- | --- |
| Cell Inlet 562 (662) | None | N/A |
| Reagent 544 (644) | None | N/A |
| IC Media 546 (646) | Media with Protein | 6 mL/hour |
| Wash 566 (666) | None | N/A |
| EC Media 568 (668) | None | N/A |

An example of the settings for attaching to the membrane 716 in the system 500, 600 may be as shown below:

TABLE 15

| Component | Setting |
| --- | --- |
| IC Inlet valve configuration | None |
| IC Inlet Rate for Pump 554, 654 | 0 mL/min |
| IC Circulation Rate for Pump 512, 612 | 0 mL/min |
| EC Inlet valve configuration | IC Media (e.g., valves 550, 650, 572, 672 open) |
| EC Inlet Rate for Pump 578, 678 | 0.1 mL/min |
| EC Circulation Rate for Pump 528, 628 | 30 mL/min |
| Outlet valve configuration | EC Outlet (e.g., valve 582, 692 open) |
| Rocker Control | Stationary (at 180°) |
| Stop Condition | Manual |

Next, the cells may be fed in step 718, in which a flow rate, e.g., low flow rate in an embodiment, is continuously added to the IC circulation loop 502, 602 and/or the EC circulation loop 504, 604. In an embodiment, the cells may be fed with media, such as media with protein, for example. Outlet settings allow for the removal of fluid added to the system, in accordance with embodiments. An example of the solutions being introduced to the system 500, 600 during the feed step 718 may be as shown below:

TABLE 16

| Bag (Connection Point) | Solution in Bag | Volume (estimation based on factory default values) |
| --- | --- | --- |
| Cell Inlet 562 (662) | None | N/A |
| Reagent 544 (644) | None | N/A |
| IC Media 546 (646) | Media with Protein | 6 mL/hour |
| Wash 566 (666) | None | N/A |
| EC Media 568 (668) | None | N/A |

An example of the settings for the feed step 718 in the system 500, 600 may be as shown below:

TABLE 17

| Component | Setting |
| --- | --- |
| IC Inlet valve configuration | IC Media (e.g., valves 550, 650, 514, 614 open) |
| IC Inlet Rate for Pump 554, 654 | 0.1 mL/min |
| IC Circulation Rate for Pump 512, 612 | 20 mL/min |
| EC Inlet valve configuration | None |
| EC Inlet Rate for Pump 578, 678 | 0 mL/min |
| EC Circulation Rate for Pump 528, 628 | 30 mL/min |
| Outlet valve configuration | IC Outlet (e.g., valve 590, 690 open) |
| Rocker Control | Stationary (at 0°) |
| Stop Condition | Manual |

When it is determined to harvest the expanded cells, such as after the cells have reached confluence, after a defined period of time, according to user preference, etc., process 700 proceeds to release cells 720, in which the cells may be released from the membrane of the bioreactor 501, 601 and may be suspended in the IC loop 502, 602. Following the release of any adherent cells, harvest operation 722 transfers the cells in suspension from the IC circulation loop 502, 602, including any cells remaining in the bioreactor 501, 601, to a harvest bag 599, 699 or other container. Process 700 then terminates at END operation 724.

The releasing of cells 720 and harvesting of those cells 722 may be a five-step process, according to embodiments. An example of the solutions being introduced to the system 500, 600 during the release/harvest steps 720, 722 may be as shown below:

TABLE 18

| Bag (Connection Point) | Solution in Bag | Volume (estimation based on factory default values) |
| --- | --- | --- |
| Cell Inlet 562 (662) | None | N/A |
| Reagent 544 (644) | Trypsin | 180 mL |
| IC Media 546 (646) | Media with Protein | 0.6 L |
| Wash 566 (666) | PBS | 1.4 L |
| EC Media 568 (668) | None | N/A |

A first step in the releasing of cells 720 may perform an IC/EC Washout task in preparation for adding a reagent. For example, IC/EC media may be replaced with a phosphate buffered saline (PBS) to remove protein, calcium (Ca2+), and magnesium (Mg2+) in preparation for adding trypsin, or another chemical-releasing agent, to release any adherent cells. An example of the settings for an example first step of the release step 720 with the system 500, 600 may be as shown below:

TABLE 19

| Component | Setting |
| --- | --- |
| IC Inlet valve configuration | Wash (e.g., valves 570, 670, 572, 672, 514, 614 open) |
| IC Inlet Rate for Pump 554, 654 | 100 mL/min |
| IC Circulation Rate for Pump 512, 612 | −17 mL/min |
| EC Inlet valve configuration | Wash |
| EC Inlet Rate for Pump 578, 678 | 148 mL/min |
| EC Circulation Rate for Pump 528, 628 | −1.7 mL/min |
| Outlet valve configuration | IC Outlet (e.g., valve 590, 690 open) and EC outlet (e.g., valve 582, 692 open) |
| Rocker Control | In Motion (−90°, 180°, 1 second interval) |
| Stop Condition | Exchange (2.5 IC volumes; 2.5 EC volumes) |

A second step of the releasing cell process 720 includes loading a reagent into the system 500, 600 until the reagent bag 544 is empty. An example of the settings for an example second step of the release step 720 with the system 500, 600 may be as shown below:

TABLE 20

| Component | Setting |
| --- | --- |
| IC Inlet valve configuration | Reagent (e.g., valves 548, 648, 514, 614 open) |
| IC Inlet Rate for Pump 554, 654 | 50 mL/min |
| IC Circulation Rate for Pump 512, 612 | 300 mL/min |
| EC Inlet valve configuration | None |
| EC Inlet Rate for Pump 578, 678 | 0 mL/min |
| EC Circulation Rate for Pump 528, 628 | 30 mL/min |
| Outlet valve configuration | EC outlet (e.g., valve 582, 692 open) |
| Rocker Control | In Motion (−90°, 180°, 1 second interval) |
| Stop Condition | Empty Bag (Reagent Bag 544 empty) |

A third step in the releasing cell process can chase the reagent into the IC loop 502, 602. An example of the settings for an example third step of the release step 720 with the system 500, 600 may be as shown below:

TABLE 21

| Component | Setting |
| --- | --- |
| IC Inlet valve configuration | Wash (e.g., valves 570, 670, 572, 672, 514, 614 open) |
| IC Inlet Rate for Pump 554, 654 | 50 mL/min |
| IC Circulation Rate for Pump 512, 612 | 300 mL/min |
| EC Inlet valve configuration | None |
| EC Inlet Rate for Pump 578, 678 | 0 mL/min |
| EC Circulation Rate for Pump 528, 628 | 30 mL/min |
| Outlet valve configuration | EC outlet (e.g., valve 582, 692 open) |
| Rocker Control | In Motion (−90°, 180°, 1 second interval) |
| Stop Condition | IC Volume (22 mL) |

A fourth step in the releasing cell process 720 can mix the reagent within the IC loop 502, 602. An example of the settings for an example fourth step of the release step 720 with the system 500, 600 may be as shown below:

TABLE 22

| Component | Setting |
| --- | --- |
| IC Inlet valve configuration | None |
| IC Inlet Rate for Pump 554, 654 | 0 mL/min |
| IC Circulation Rate for Pump 512, 612 | 300 mL/min |
| EC Inlet valve configuration | None |
| EC Inlet Rate for Pump 578, 678 | 0 mL/min |
| EC Circulation Rate for Pump 528, 628 | 30 mL/min |
| Outlet valve configuration | EC outlet (e.g., valve 582, 692 open) |
| Rocker Control | In Motion (−90°, 180°, 1 second interval) |
| Stop Condition | Time (4 Minutes) |

An example of the settings for an example fifth step, which may generally be a harvest step 722, with the system 500, 600 may be as shown below:

TABLE 23

| Component | Setting |
| --- | --- |
| IC Inlet valve configuration | IC Media (e.g., valves 550, 650, 514, 614 open) |
| IC Inlet Rate for Pump 554, 654 | 400 mL/min |
| IC Circulation Rate for Pump 512, 612 | −70 mL/min |
| EC Inlet valve configuration | IC Media (e.g., valves 550, 650, 572, 672 open) |
| EC Inlet Rate for Pump 578, 678 | 60 mL/min |
| EC Circulation Rate for Pump 528, 628 | 30 mL/min |
| Outlet valve configuration | Harvest (e.g., valve 598, 698 open) |
| Rocker Control | In Motion (−90°, 180°, 1 second interval) |
| Stop Condition | IC Volume (378 mL) |

As described above, following release step 720 and harvest step 722, process 700 terminates at END operation 724.

Figure 8A:
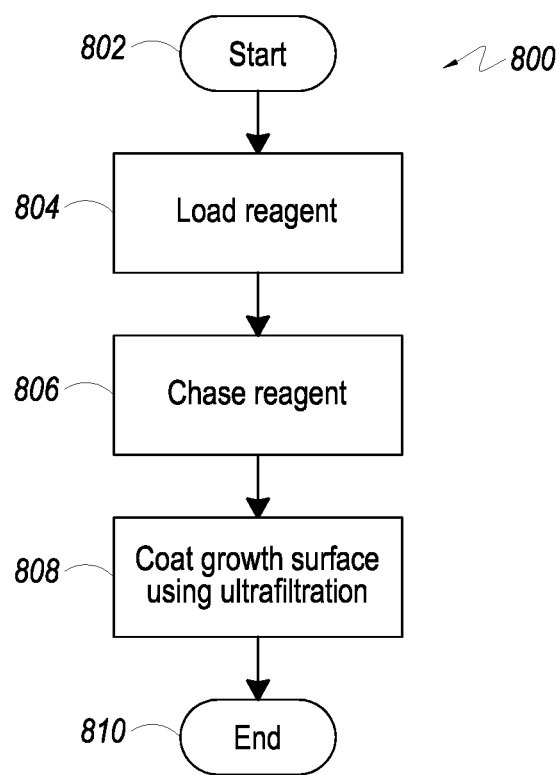
FIG. 8A illustrates a flow diagram depicting the operational characteristics of a process for applying a reagent to a cell growth surface in accordance with embodiments of the present disclosure.

Turning to FIG. 8A, example operational steps 800 of a process for applying an agent or reagent to a cell growth surface that may be used with a cell expansion system, such as CES 500 (FIG. 5) or CES 600 (FIG. 6), are provided in accordance with embodiments of the present disclosure. START operation is initiated 802, and process 800 proceeds to load a reagent, or coating agent, 804 into a circulation loop, e.g., IC loop 502, 602, of a cell expansion system 500, 600. In an embodiment, such loading proceeds until a bag (e.g., 544) or container including the reagent or coating agent is empty. In another embodiment, such loading proceeds for a defined period of time or other condition as understood by a person of skill in the art. Example parameters 822 and 828 for such loading step 804 may be found in FIG. 8C, in which Table 821 provides example parameters or settings 828 for various steps 822, 824, and 826 of applying an agent to a cell growth surface in accordance with an embodiment of the present disclosure. Such example parameters or settings 828 include an example IC inlet of about 100 mL SDE CPPT, as an example coating solution. In an embodiment, CPPT may be prepared so as to create about 25 mL "single donor equivalent (SDE)" aliquots: (1) unprocessed CPPT may be obtained from a blood center; (2) CPPT may be diluted in PBS to a final volume of about 100 mL for every donor represented by the product (e.g.: 5 donors for CPPT product=about 500 mL of total solution); (3) this stock solution may be divided into about 25 mL aliquots. In an embodiment, each aliquot may be sufficient to coat one cell expansion system, e.g., Quantum System®, bioreactor, for example. Other volumes and/or proportions may be used in accordance with embodiments of the present disclosure.

In an embodiment, prior to loading such reagent or coating agent, an outlet or waste valve 590, 690 to one of the circulation loops, e.g., IC loop 502, 602, may be closed, while the outlet or waste valve 582, 692 to the other circulation loop, e.g., EC loop 504, 604, remains open. For example, the IC waste or outlet valve 590, 690 may be closed while the EC waste or outlet valve 582, 692 may be open, according to an embodiment. In another embodiment, such closing of an outlet or waste valve, e.g., IC waste or outlet valve 590, 690, while keeping another outlet or waste valve, e.g., EC waste or outlet valve 582, 692, open may occur after loading the reagent into the circulation loop 502, 602. In other embodiments, other types of fluid flow control device(s) to control fluid movement may be used as understood by a person of skill in the art.

Next, the reagent may be chased or washed 806 from an air removal chamber 556, 656 into the circulation loop, e.g., IC loop 502, 602. Example parameters 824 and 828 for such chase step 806 may be found in FIG. 8C.

The cell growth surface of the bioreactor 501, 601, e.g., cell growth surface of hollow fibers where a hollow fiber bioreactor is used, may then be coated 808 by controlling the fluid movement, e.g., ultrafiltration, in the bioreactor 501, 601. Example parameters 826 and 828 for such coating step 808 may be found in FIG. 8C. As shown in FIG. 8C, coating step 808 and example parameters 826, 828 may include a stop condition of about ten (10) minutes, according to an embodiment. Steps 822, 824, and 826 for applying an agent to a growth surface may be followed by an IC/EC Washout step, for example, and/or other steps, where it is desired to continue with a process for expanding cells in a cell expansion system 500, 600, according to an embodiment.

As described above, control of the fluid movement may use ultrafiltration, such as positive ultrafiltration, to move fluid from one side (the IC side 502, 602) of the bioreactor 501, 601 to the other side (the EC side 504, 604), according to embodiments. For example, where the IC outlet or waste valve 590, 690 may be closed, with the EC outlet or waste valve 582, 692 open, a fluid in the bioreactor 501, 601 may have no pathway but through the pores of the fibers (IC outlet valve 590, 690 closed). In an embodiment, the IC inlet rate may be set to wash the IC side 502, 602 with media or a fluid, such as phosphate buffered saline (PBS), for example. Accordingly, the solution may flow through the pores of the fibers from the IC side 502, 602 to the EC side 504, 604. Such coating agent, e.g., CPPT, may be hydrostatically deposited onto the inner wall(s) of the bioreactor fiber for a defined time period. For example, such time period may be about ten (10) minutes, according to an embodiment. Such membrane ultrafiltration method allows adherence promoting proteins to be physisorbed on the bioreactor fibers as the coating solution flows through the pores of the fiber from the IC side to the EC side, for example.

As described above, the active promoting of the coating agent to a cell growth surface may significantly decrease the amount of time it may take to coat the growth surface as compared to other methods of coating a growth surface. In embodiments, such coating procedure using ultrafiltration may be referred to as an expedited coating procedure. Such expedited coating procedure using active moving of the coating agent to the cell growth surface(s) through ultrafiltration may use less time to coat the cell growth surface than procedures using passive coating procedures which may take overnight or about twelve (12) hours to about sixteen (16) hours to coat the bioreactor. For example, such expedited coating procedure may take less than or equal to about four (4) hours. In embodiments, such expedited coating procedure may take any time period in a range from above or equal to about five (5) minutes to less than or equal to about sixty (60) minutes, or any other range therein, depending on the procedure. For example, such coating procedure may take less than or equal to about ten (10) minutes, less than or equal to about twelve (12) minutes, less than or equal to about fifteen (15) minutes, less than or equal to about twenty (20) minutes, less than or equal to about thirty (30) minutes, less than or equal to about forty-five (45) minutes, less than or equal to about sixty (60) minutes, etc.

Following the application of the reagent or coating agent to the cell growth surface, process 800 then terminates at END operation 810.

While FIG. 8A illustrates a method for applying a coating agent or reagent to a cell growth surface, FIG. 8B depicts a schematic of applying an agent to a growth surface of a hollow fiber, in accordance with embodiments of the present disclosure. In embodiments, schematic 811 depicts the flow of a coating agent or reagent solution, such as cryoprecipitate solution 814, through a single fiber 812, e.g., hollow fiber, of a bioreactor during an active coating procedure. In schematic 811, a coating agent and/or coating solution, e.g., a cryoprecipitate solution, may be introduced to the fibers of a bioreactor, e.g., a hollow fiber bioreactor 501, 601, on the intracapillary (IC) side 816, for example. In such embodiment, an IC waste valve or IC outlet valve 590, 690 may be closed, while an EC waste valve or EC outlet valve 582, 692 may be open. In embodiments, the IC inlet rate for a chase step, e.g., step 824 (FIG. 8C), may be set. The IC inlet rate may then be set for a Wash step, e.g., step 826 (FIG. 8C), according to an embodiment. For example, the IC inlet rate may be set to about 50 mL/minute for a wash task with media or a fluid, such as phosphate buffered saline (PBS). In embodiments, the IC inlet rate may be set to any rate in a range including a value greater than or equal to about 5 mL/minute to less than or equal to about 100 mL/minute. For example, the IC inlet rate may be set to a value greater than or equal to about 40 mL/minute to less than or equal to about 60 mL/minute.

Returning to FIG. 8B, the coating agent in the coating solution, e.g., cryoprecipitate solution 814, may be hydrostatically deposited onto the inner wall of bioreactor fiber 812 for a specified time period, e.g., about ten (10) minutes. Various time periods may be used based on the CES 500, 600 configurations, for example. Such membrane ultrafiltration process allows adherence promoting protein(s) to be physisorbed on the bioreactor fibers as the reagent solution or coating solution flows through the pores 818 of the fiber 812 from the IC side of the fiber 816 to the EC side of the fiber 820.

Figure 9A:
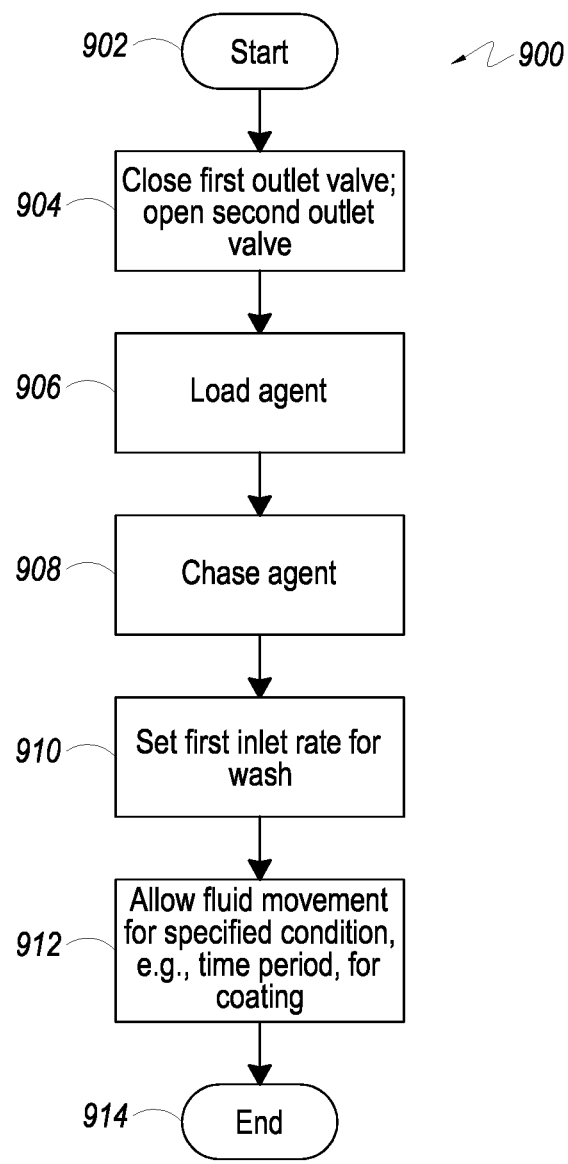
FIG. 9A depicts a flow diagram illustrating the operational characteristics of a process for applying an agent to a cell growth surface in accordance with embodiments of the present disclosure.

Turning to FIG. 9A, example operational steps 900 of a process for applying an agent or reagent to a cell growth surface that may be used with a cell expansion system, such as CES 500 (FIG. 5) or CES 600 (FIG. 6), are provided in accordance with embodiments of the present disclosure. In embodiments, such CES is automated, and various steps and/or parameters may be pre-programmed, set, and/or created to execute one or more tasks to expand cells. START operation is initiated 902, and process 900 proceeds to close 904 a first outlet or waste valve 590, 690, and open (or leave/remain open) a second outlet or waste valve 582, 692, where the first 590, 690 and second 582, 682 outlet valves are different. In an embodiment, such as where cells may be grown on the IC side, for example, an IC outlet valve or IC waste valve 590, 690 may be closed, while an EC outlet valve or EC waste valve 582, 692 may be open or remain open. In another embodiment, such as where cells may be grown on the EC side, for example, an EC outlet valve or EC waste valve 582, 692 may be closed, while an IC outlet valve or IC waste valve 590, 690 may be open or remain opened. In an embodiment, step 904 occurs before loading a coating agent or reagent into the cell expansion system 500, 600. In another embodiment, step 904 occurs after the loading of a coating agent. In an embodiment, step 904 may occur at any time during process 900. Process 900 is offered for illustrative purposes and may be rearranged, combined into other steps, etc. Further, additional or fewer steps may be used in other embodiments.

Returning to FIG. 9, process 900 proceeds to load an agent 906 or agent solution, e.g., coating agent or coating solution, into a cell expansion system, such as cell expansion system 500, 600, for example. In an embodiment, a coating agent or coating agent solution is loaded into a circulation loop, e.g., IC loop 502, 602, of a cell expansion system 500, 600. In an embodiment, such loading proceeds until a bag (e.g., 544) or container including the reagent or coating agent is empty. In another embodiment, such loading proceeds for a defined period of time or other condition as understood by a person of skill in the art.

Next, the agent or reagent may be chased or washed 908 from an air removal chamber 556, 656 into the circulation loop, e.g., IC loop 502, 602. Process 900 next proceeds to set a first inlet rate 910, e.g., IC inlet rate, to wash a first side, e.g., IC side 816 (FIG. 8B), with media or a fluid, such as phosphate buffered saline (PBS), for example. For example, the IC inlet rate may be set to about 50 mL/minute for a wash task with media or a fluid, such as phosphate buffered saline (PBS). In embodiments, the IC inlet rate may be set to any rate in a range including a value greater than or equal to about 5 mL/minute to less than or equal to about 100 mL/minute. For example, the IC inlet rate may be set to a value greater than or equal to about 40 mL/minute to less than or equal to about 60 mL/minute. In embodiments, the IC inlet rate may be set to about 51 mL/minute; about 52 mL/minute; about 53 mL/minute; about 54 mL/minute; about 55 mL/minute; about 56 mL/minute; about 57 mL/minute; about 58 mL/minute; about 59 mL/minute; about 60 mL/minute; about 49 mL/minute; about 48 mL/minute; about 47 mL/minute; about 46 mL/minute; about 45 mL/minute; about 44 mL/minute; about 43 mL/minute; about 42 mL/minute; about 41 mL/minute; about 40 mL/minute; etc.

Such washing, or increased inlet rate, promotes the movement of fluid 912 from a first side 816 (FIG. 8B) of a hollow fiber 812 to a second side 820 of the hollow fiber 812, e.g., from the IC side 816 to the EC side 820, in which ultrafiltration allows proteins or molecules that are too large to pass through the pores 818 of a hollow fiber 812 to adhere to the bioreactor fiber 812 and thus coat the walls while the fluid in which the coating agent is suspended flows through the pores 818. Where the fluid flows through the pores 818 of the fiber 812 from the IC 816 to the EC side 820, positive ultrafiltration may result in the deposit of the coating agent or reagent on the inner walls, or IC side 816, of the fiber(s). On the other hand, in an embodiment where cells are grown on an EC side 820 and where the solution flows through the pores 818 of the fiber 812 from the EC side 820 to the IC side 816, negative ultrafiltration may result in the deposit of the coating agent or reagent on the outer walls, or EC side 820, of the fiber(s) 812. In an embodiment, such fluid movement may occur for a specified time period, e.g., about ten (10) minutes, to allow for such coating. In an embodiment, such active promoting of the coating agent to a cell growth surface may significantly decrease the amount of time it may take to coat the cell growth surface as compared to other methods of coating a cell growth surface. In embodiments, such coating procedure using ultrafiltration may be referred to as an expedited coating procedure. Such expedited coating procedure using active moving of the coating agent to the cell growth surface(s) through ultrafiltration may use less time to coat the cell growth surface than procedures using passive coating procedures which may take overnight or about twelve (12) hours to about sixteen (16) hours to coat the bioreactor. For example, such expedited coating procedure may take less than or equal to about four (4) hours. In embodiments, such expedited coating procedure may take any time period in a range from above or equal to about five (5) minutes to less than or equal to about sixty (60) minutes, or any other range therein, depending on the procedure. For example, such coating procedure may take less than or equal to about ten (10) minutes, less than or equal to about twelve (12) minutes, less than or equal to about fifteen (15) minutes, less than or equal to about twenty (20) minutes, less than or equal to about thirty (30) minutes, less than or equal to about forty-five (45) minutes, less than or equal to about sixty (60) minutes, etc. In other embodiments, other conditions may be used to determine when to stop or decrease the active promotion of the fluid. For example, such active promotion may be stopped or decreased when a media bag (e.g., 566) containing a wash solution is empty. Other conditions may be used according to embodiments. Process 900 then terminates at END operation 914.

Figure 9B:
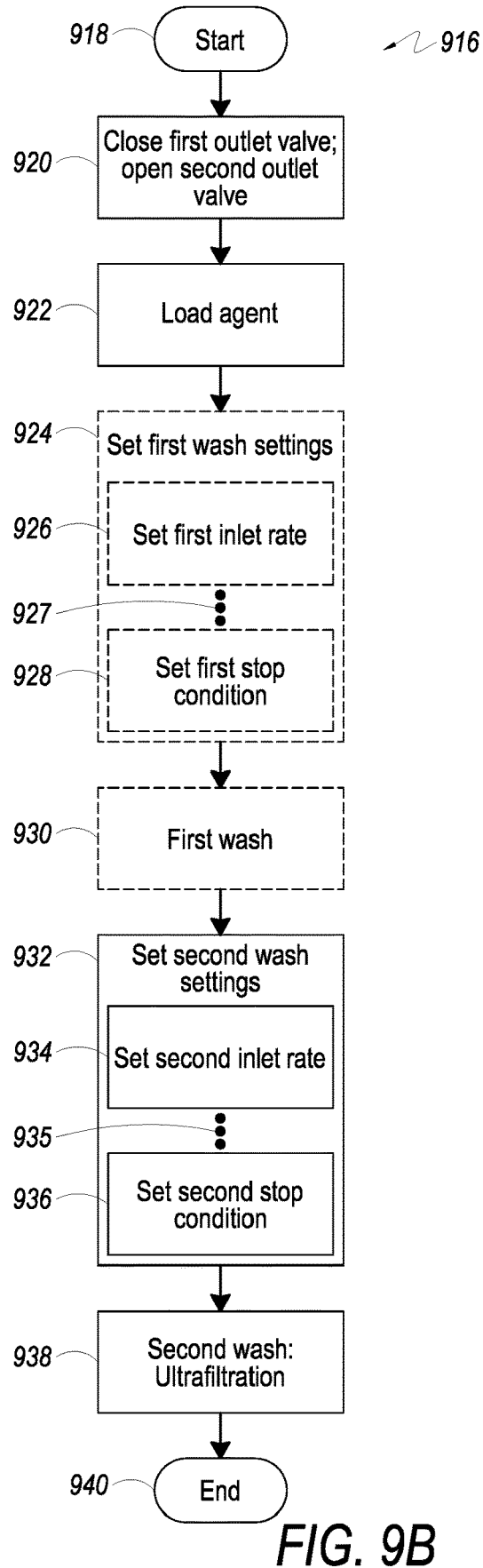
FIG. 9B depicts a flow diagram illustrating the operational characteristics of a process for applying an agent to a cell growth surface in accordance with embodiments of the present disclosure.

Turning to FIG. 9B, example operational steps 916 of a process for applying an agent to a cell growth surface that may be used with a cell expansion system, such as CES 500 (FIG. 5) or CES 600 (FIG. 6), are provided in accordance with embodiments of the present disclosure. In embodiments, such CES is automated, and various steps and/or parameters may be pre-programmed, set, and/or created as custom or user-defined tasks to expand cells. START operation is initiated 918, and process 916 proceeds to close 920 a first outlet or waste valve 590, 690, and open (or leave/remain open) a second outlet or waste valve 582, 692, where the first 590, 690 and second 582, 692 outlet valves are different. In an embodiment, such as where cells may be grown on the IC side, for example, an IC outlet valve or IC waste valve 590, 690 may be closed, while an EC outlet valve or EC waste valve 582, 692 may be open or remain open. In another embodiment, such as where cells may be grown on the EC side, for example, an EC outlet valve or EC waste valve 582, 692 may be closed, while an IC outlet valve or IC waste valve 590, 690 may be open or remain opened. In an embodiment, step 920 occurs before loading a coating agent or reagent into the cell expansion system 500, 600. In another embodiment, step 920 occurs after the loading of a coating agent. In an embodiment, step 920 may occur at any time during process 916. Process 916 is offered for illustrative purposes and may be rearranged, combined into other steps, etc. Further, additional or fewer steps may be used in other embodiments.

Returning to FIG. 9B, process 916 proceeds to load an agent 922 or agent solution, e.g., coating agent or coating solution, into a cell expansion system, such as cell expansion system 500, 600, for example. In an embodiment, a coating agent or coating agent solution is loaded into a circulation loop, e.g., IC loop 502, 602, of a cell expansion system 500,

600. In an embodiment, such loading proceeds until a bag (e.g., 544) or container including the reagent or coating agent is empty. In another embodiment, such loading proceeds for a defined period of time or other condition as understood by a person of skill in the art.

Next, process 916 proceeds to optional step 924, in which the settings for a first wash may be set. During such first wash, the agent may be chased or washed from an air removal chamber 556, 656 into the circulation loop, e.g., IC loop 502, 602. The settings may include, for example, optionally setting a first inlet rate 926 and/or optionally setting a first stop condition 928. An example of a first stop condition may include a particular volume, e.g., an IC volume. Optional settings 926 and 928 are offered merely for illustrative purposes. Other settings and/or subsets of settings to control a first wash may be included. There may be fewer or more settings as represented by ellipsis 927. When settings for a first wash are set, process 916 next proceeds to optional first wash 930.

Following optional first wash 930 (or where no first wash is desired, following load agent 922), process 916 proceeds to set second wash settings 932. For example, a second inlet rate, e.g., IC inlet rate, may be set 934 to wash a first side, e.g., IC side 816 (FIG. 8B), with media or a fluid, such as phosphate buffered saline (PBS), for example. For example, the IC inlet rate may be set to about 50 mL/minute for a wash task with media or a fluid, such as phosphate buffered saline (PBS). In embodiments, the IC inlet rate may be set to any rate in a range including a value greater than or equal to about 5 mL/minute to less than or equal to about 100 mL/minute. For example, the IC inlet rate may be set to a value greater than or equal to about 40 mL/minute to less than or equal to about 60 mL/minute.

Additional or other settings may also be set to control such second wash. For example, a second stop condition may be set 936. Such stop condition may include a time period, or time interval, in which the second wash may be stopped when such stop condition is reached. As an example, a ten (10) minute time period may be set as a second stop condition for a second wash. Any time period may be used in accordance with embodiments of the present disclosure. Settings 934 and 936 are offered merely for illustrative purposes. Other settings and/or subsets of settings to control a second wash may be included. There may be fewer or more settings as represented by ellipsis 935.

Following the entering of the second wash settings at step 932, process 916 next proceeds to conducting a second wash 938. Such washing, or increased inlet rate, promotes the movement of fluid from a first side 816 (FIG. 8B) of a hollow fiber 812 to a second side 820 of the hollow fiber 812, e.g., from the IC side 816 to the EC side 820, in which ultrafiltration allows proteins or molecules that are too large to pass through the pores 818 of a hollow fiber 812 to adhere to the bioreactor fiber 812 and thus coat the walls while the solution flows through the pores 818. Where the solution flows through the pores 818 of the fiber 812 from the IC 816 to the EC side 820, positive ultrafiltration may result in the deposit of the coating agent or reagent on the inner walls, or IC side 816, of the fiber(s). On the other hand, in an embodiment where cells are grown on an EC side 820 and where the solution flows through the pores 818 of the fiber 812 from the EC side 820 to the IC side 816, negative ultrafiltration may result in the deposit of the coating agent or reagent on the outer walls, or EC side 820, of the fiber(s) 812.

Active promoting of the coating agent to a cell growth surface may significantly decrease the amount of time it may take to coat the growth surface as compared to other methods of coating a growth surface. In embodiments, such coating procedure using ultrafiltration may be referred to as an expedited coating procedure. For example, such expedited coating procedure may take less than or equal to about four (4) hours. In an embodiment, such fluid movement may occur for a specified time period, e.g., about ten (10) minutes, to allow for such coating. For example, such coating procedure may take any time period in a range from above or equal to about five (5) minutes to less than or equal to about sixty (60) minutes, or any other range therein, depending on the procedure. For example, such coating procedure may take less than or equal to about ten (10) minutes, less than or equal to about twelve (12) minutes, less than or equal to about fifteen (15) minutes, less than or equal to about twenty (20) minutes, less than or equal to about thirty (30) minutes, less than or equal to about forty-five (45) minutes, less than or equal to about sixty (60) minutes, etc. Any time period may be used in accordance with embodiments of the present disclosure. In an embodiment, such time period may be based on a stop condition, such as a second stop condition set in step 936. For example, a stop condition may be set where an automated CES is used to expand cells. In other embodiments, other conditions may be used to determine when to stop or decrease the active promotion of the fluid. For example, such active promotion may be stopped or decreased when a media bag (e.g., 566) containing the wash solution is empty. Other conditions may be used according to embodiments. Process 916 then terminates at END operation 940.

Figure 10:
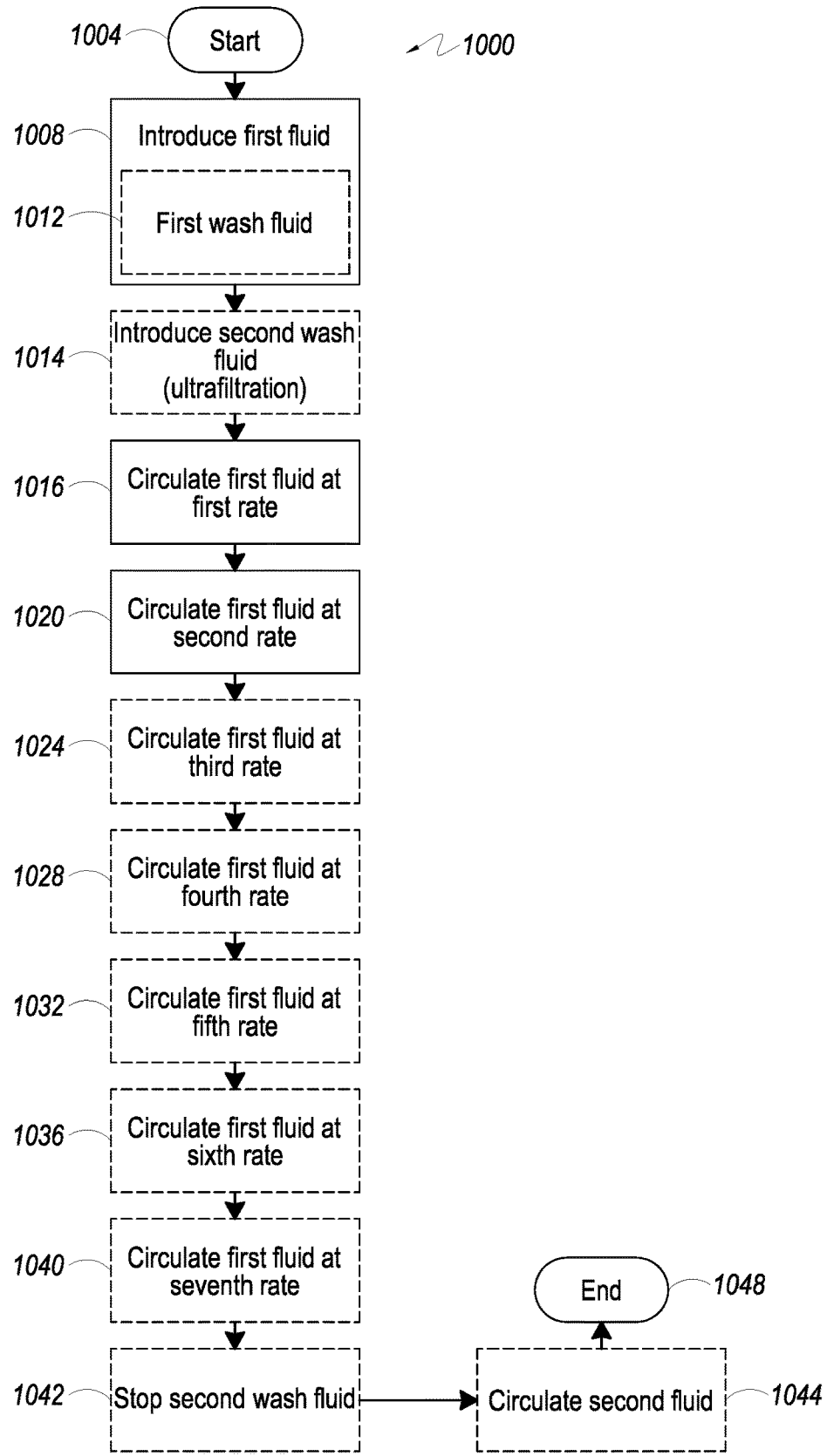
FIG. 10 illustrates a flow for a process of coating a bioreactor according to an embodiment.

Referring now to FIG. 10, flow 1000 illustrates yet another embodiment of a process for coating a cell growth surface, e.g., such as a surface of a hollow fiber. Flow 1000 starts at step 1004 and proceeds to step 1008 where fluid that includes a reagent may be introduced into a cell expansion system and a bioreactor such as bioreactors 100, 501, and/or 601. In embodiments, step 1008 may involve activating one or more pumps (554, 654) to introduce fluid with the reagent from a bag (562) or connection point (662) into a fluid flow path.

As part of introducing the fluid with the reagent into the cell expansion system, step 1008 may involve optional step 1012, where a wash fluid (e.g., PBS) may be used to chase the reagent from parts of the CES. For example, the wash fluid may move any reagent left behind in an ARC, such as ARC 556/656. The wash fluid may chase any lingering reagent into the bioreactor and/or a fluid flow path associated with the bioreactor e.g., 502/602.

Flow 1000 then passes to step 1014 where a second wash fluid may be introduced into the bioreactor. In embodiments, step 1014 may involve activating a pump, such as pumps 554,654 to introduce the second wash fluid from a bag (562) or connection point (662) into a fluid flow path and into the bioreactor (100, 501, and/or 601). In embodiments, the second wash fluid is introduced to create conditions for ultrafiltration, as described above. Ultrafiltration allows proteins or molecules (e.g., the coating reagent) that are too large to pass through the pores 818 (FIG. 8) of a hollow fiber 812 (FIG. 8) to adhere to the bioreactor fiber 812 and thus coat the walls while the solution flows through the pores 818. Where the solution flows through the pores 818 of the fiber 812 from the IC 816 to the EC side 820, positive ultrafiltration may result in the deposit of the coating agent or reagent on the inner walls, or IC side 816, of the fibers. In embodiments, the second wash fluid introduced at step 1014 may be continuously introduced as steps 1016 through 1040 are performed.

Flow 1000 then passes to step 1016 where fluid that includes the coating reagent may be circulated through the bioreactor such as bioreactors 100, 501, and/or 601. In embodiments, step 1016 may involve activating one or more pumps to circulate fluid with the reagent through the bioreactor. For example, an IC circulation pump (e.g., 512 or 612) may be activated to circulate fluid through the IC side of a bioreactor at a first circulation flow rate. In at least one embodiment, fluid may pass through hollow fibers (e.g., the lumen).

In embodiments, the first rate may be a relatively high flow rate. In embodiments, the first circulation flow rate may be less than about 500 ml/min, less than about 400 ml/min, or even less than about 300 ml/min. In other embodiments, the first circulation rate may be greater than about 50 ml/min, greater than about 100 ml/min, or even greater than about 150 ml/min. In one embodiment, the first circulation flow rate is between about 100 ml/min and about 500 ml/min, such as about 300 ml/min.

Step 1016 may be performed for a first predetermined period of time. In one specific example, the first period of time may be about 4 minutes, about 8 minutes, about 12 minutes, or even about 16 minutes. In other embodiments, the first predetermined period of time may be less than about 20 minutes, less than about 15 minutes, less than about 10 minutes, or even less than about 5 minutes. In some embodiments, the first predetermined period of time may be greater than about 2 minutes, greater than about 4 minutes, greater than about 6 minutes, greater than about 8 minutes, greater than about 10 minutes, greater than about 12 minutes, greater than about 14 minutes, greater than about 16 minutes, greater than about 18 minutes, or even greater than about 20 minutes. Step 1016 may be performed in embodiments to provide time to allow the reagent to coat portions of the bioreactor. For example, when the bioreactor comprises hollow fibers, step 1016 may be performed to allow the reagent time to coat interior surfaces of the hollow fibers.

Flow 1000 passes to step 1020, wherein fluid with the reagent is circulated at a second flow rate, which may be less than the first flow rate. In embodiments, the second flow rate may be less than about 400 ml/min, less than about 300 ml/min, or even less than about 200 ml/min. In other embodiments, the second circulation rate may be greater than about 25 ml/min, greater than about 50 ml/min, or even greater than about 75 ml/min. In one embodiment, the second circulation flow rate is between about 100 ml/min and about 300 ml/min, such as about 250 ml/min.

Step 1020 may be performed for a second predetermined period of time. In one specific example, the second period of time may be about 4 minutes, about 8 minutes, about 12 minutes, or even about 16 minutes. In other embodiments, the second predetermined period of time may be less than about 20 minutes, less than about 15 minutes, less than about 10 minutes, or even less than about 5 minutes. In some embodiments, the second predetermined period of time may be greater than about 2 minutes, greater than about 4 minutes, greater than about 6 minutes, greater than about 8 minutes, greater than about 10 minutes, greater than about 12 minutes, greater than about 14 minutes, greater than about 16 minutes, greater than about 18 minutes, or even greater than about 20 minutes. Step 1020 may be performed in embodiments to provide time to allow the reagent to coat portions of the bioreactor. For example, when the bioreactor comprises hollow fibers, step 1020 may be performed to allow the reagent time to coat interior surfaces of the hollow fibers.

Flow 1000 passes to optional step 1024, wherein fluid with the reagent is circulated at a third flow rate, which may be less than the first flow rate. In embodiments, the third flow rate may be less than the second flow rate. In embodiments, the third flow rate may be less than about 350 ml/min, less than about 300 ml/min, or even less than about 250 ml/min. In other embodiments, the second circulation rate may be greater than about 25 ml/min, greater than about 50 ml/min, or even greater than about 75 ml/min. In one embodiment, the third circulation flow rate is between about 50 ml/min and about 250 ml/min, such as about 200 ml/min.

Optional step 1024 may be performed for a third predetermined period of time. In one specific example, the second period of time may be about 4 minutes, about 8 minutes, about 12 minutes, or even about 16 minutes. In other embodiments, the third predetermined period of time may be less than about 20 minutes, less than about 15 minutes, less than about 10 minutes, or even less than about 5 minutes. In some embodiments, the third predetermined period of time may be greater than about 2 minutes, greater than about 4 minutes, greater than about 6 minutes, greater than about 8 minutes, greater than about 10 minutes, greater than about 12 minutes, greater than about 14 minutes, greater than about 16 minutes, greater than about 18 minutes, or even greater than about 20 minutes. Step 1024 may be performed in embodiments to provide time to allow the reagent to coat portions of the bioreactor. For example, when the bioreactor comprises hollow fibers, step 1024 may be performed to allow the reagent time to coat interior surfaces of the hollow fibers.

Flow 1000 then passes to optional step 1028, where fluid with the reagent is circulated at a fourth flow rate, which may be less than the third flow rate. In embodiments, the fourth flow rate may be less than about 250 ml/min, less than about 200 ml/min, or even less than about 150 ml/min. In other embodiments, the second circulation rate may be greater than about 25 ml/min, greater than about 50 ml/min, or even greater than about 75 ml/min. In one embodiment, the fourth circulation flow rate is between about 25 ml/min and about 200 ml/min, such as about 150 ml/min.

Optional step 1028 may be performed for a fourth predetermined period of time. In one specific example, the second period of time may be about 4 minutes, about 8 minutes, about 12 minutes, or even about 16 minutes. In other embodiments, the fourth predetermined period of time may be less than about 20 minutes, less than about 15 minutes, less than about 10 minutes, or even less than about 5 minutes. In some embodiments, the fourth predetermined period of time may be greater than about 2 minutes, greater than about 4 minutes, greater than about 6 minutes, greater than about 8 minutes, greater than about 10 minutes, greater than about 12 minutes, greater than about 14 minutes, greater than about 16 minutes, greater than about 18 minutes, or even greater than about 20 minutes. Step 1028 may be performed in embodiments to provide time to allow the reagent to coat portions of the bioreactor. For example, when the bioreactor comprises hollow fibers, step 1028 may be performed to allow the reagent time to coat interior surfaces of the hollow fibers.

Flow passes to optional step 1032, where fluid with the reagent is circulated at a fifth flow rate, which may be less than the fourth flow rate. In embodiments, the fifth flow rate may be less than about 200 ml/min, less than about 150 ml/min, or even less than about 100 ml/min. In other embodiments, the fifth circulation rate may be greater than about 25 ml/min, greater than about 50 ml/min, or even greater than about 75 ml/min. In one embodiment, the fifth circulation flow rate is between about 25 ml/min and about 150 ml/min, such as about 100 ml/min.

Optional step 1032 may be performed for a fifth predetermined period of time. In one specific example, the fifth period of time may be about 4 minutes, about 8 minutes, about 12 minutes, or even about 16 minutes. In other embodiments, the fifth predetermined period of time may be less than about 20 minutes, less than about 15 minutes, less than about 10 minutes, or even less than about 5 minutes. In some embodiments, the fifth predetermined period of time may be greater than about 2 minutes, greater than about 4 minutes, greater than about 6 minutes, greater than about 8 minutes, greater than about 10 minutes, greater than about 12 minutes, greater than about 14 minutes, greater than about 16 minutes, greater than about 18 minutes, or even greater than about 20 minutes. Step 1032 may be performed in embodiments to provide time to allow the reagent to coat portions of the bioreactor. For example, when the bioreactor comprises hollow fibers, step 1032 may be performed to allow the reagent time to coat interior surfaces of the hollow fibers.

Flow 1000 passes to optional step 1036, where fluid with the reagent is circulated at a sixth flow rate, which may be less than the fifth flow rate. In embodiments, the sixth flow rate may be less than about 100 ml/min, less than about 50 ml/min, or even less than about 25 ml/min. In other embodiments, the sixth circulation rate may be greater than about 5 ml/min, greater than about 10 ml/min, or even greater than about 15 ml/min. In one embodiment, the sixth circulation flow rate is between about 25 ml/min and about 100 ml/min, such as about 50 ml/min.

Optional step 1036 may be performed for a sixth predetermined period of time. In one specific example, the sixth period of time may be about 4 minutes, about 8 minutes, about 12 minutes, or even about 16 minutes. In other embodiments, the sixth predetermined period of time may be less than about 20 minutes, less than about 15 minutes, less than about 10 minutes, or even less than about 5 minutes. In some embodiments, the sixth predetermined period of time may be greater than about 2 minutes, greater than about 4 minutes, greater than about 6 minutes, greater than about 8 minutes, greater than about 10 minutes, greater than about 12 minutes, greater than about 14 minutes, greater than about 16 minutes, greater than about 18 minutes, or even greater than about 20 minutes. Step 1036 may be performed in embodiments to provide time to allow the reagent to coat portions of the bioreactor. For example, when the bioreactor comprises hollow fibers, step 1036 may be performed to allow the reagent time to coat interior surfaces of the hollow fibers.

Flow 1000 passes to optional step 1040, where fluid with the reagent is circulated at a seventh flow rate, which may be less than the sixth flow rate. In embodiments, the seventh flow rate may be less than about 100 ml/min, less than about 50 ml/min, or even less than about 25 ml/min. In other embodiments, the seventh circulation rate may be greater than about 10 ml/min, greater than about 15 ml/min, or even greater than about 20 ml/min. In one embodiment, the seventh circulation flow rate is between about 10 ml/min and about 50 ml/min, such as about 25 ml/min.

Optional step 1040 may be performed for a seventh predetermined period of time. In one specific example, the seventh period of time may be about 4 minutes, about 8 minutes, about 12 minutes, or even about 16 minutes. In other embodiments, the sixth predetermined period of time may be less than about 20 minutes, less than about 15 minutes, less than about 10 minutes, or even less than about 5 minutes. In some embodiments, the sixth predetermined period of time may be greater than about 2 minutes, greater than about 4 minutes, greater than about 6 minutes, greater than about 8 minutes, greater than about 10 minutes, greater than about 12 minutes, greater than about 14 minutes, greater than about 16 minutes, greater than about 18 minutes, or even greater than about 20 minutes. Step 1040 may be performed in embodiments to provide time to allow the reagent to coat portions of the bioreactor. For example, when the bioreactor comprises hollow fibers, step 1040 may be performed to allow the reagent time to coat interior surfaces of the hollow fibers (e.g., the lumen).

Flow 1000 then passes to step 1042 where introduction of the second wash fluid into the bioreactor is stopped. In embodiments, step 1042 may involve deactivating a pump, such as pump 554, 654 to stop the introduction of the second wash fluid in the fluid flow path and into the bioreactor (100, 501, and/or 601). In embodiments, stopping the introduction of the second wash fluid stops the process of ultrafiltration.

Flow 1000 then passes to step 1044, where a second fluid, that may not include the reagent, or have a lower concentration of the reagent, may be circulated through the bioreactor. In embodiments, step 1044 may be performed to wash any remaining reagent that has not coated a surface of the bioreactor out of the bioreactor and CES. As noted above, flow 1000 may be part of a larger process such as a process for growing and harvesting cells in a cell expansion system, such as flow 700. Therefore, in embodiments, step 1044 may be implemented as part of steps performed in the larger process, such as step 710 (FIG. 7). Flow 1000 then ends at 1048.

Figure 11:
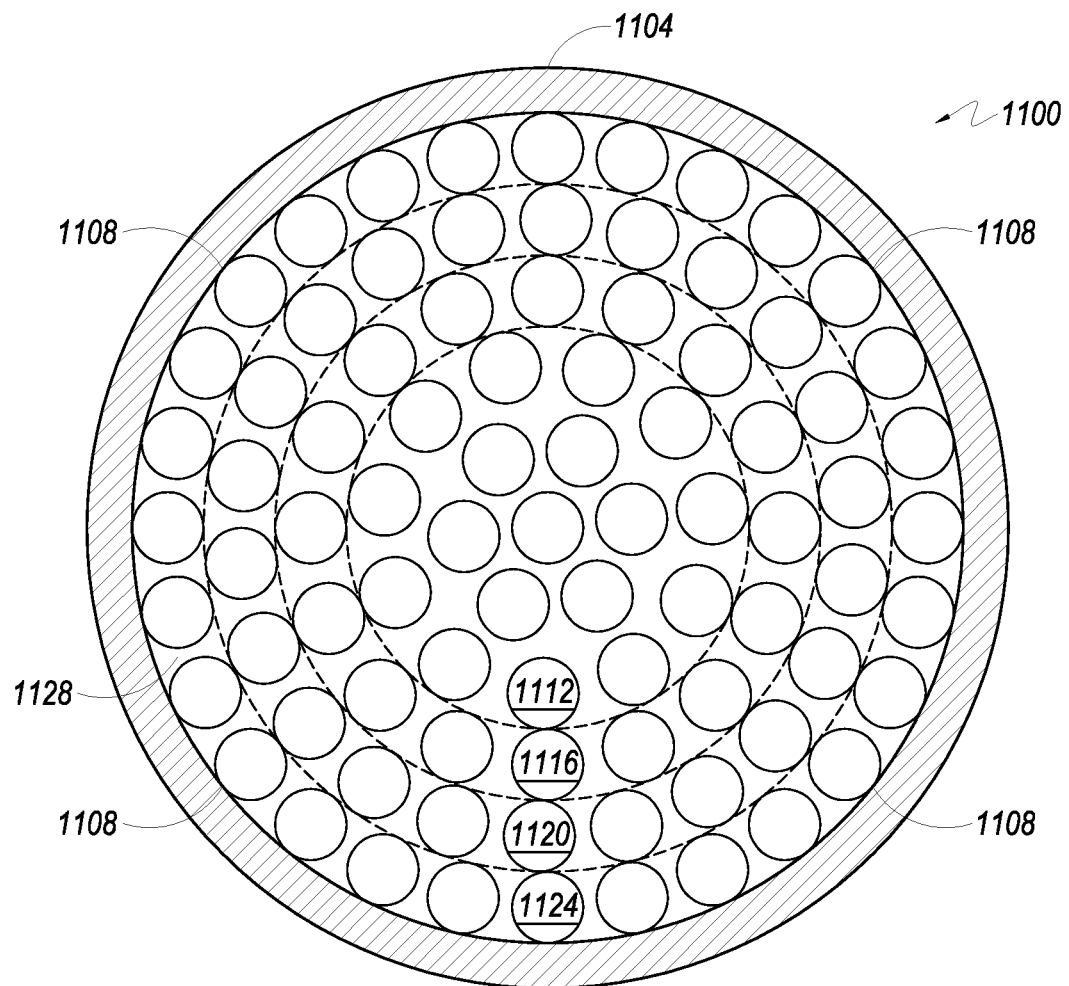
FIG. 11 illustrates a cross section of a bioreactor showing a plurality of hollow fibers and zones of hollow fibers through which liquid containing a reagent may circulate at different flow rates.
Figure 12:
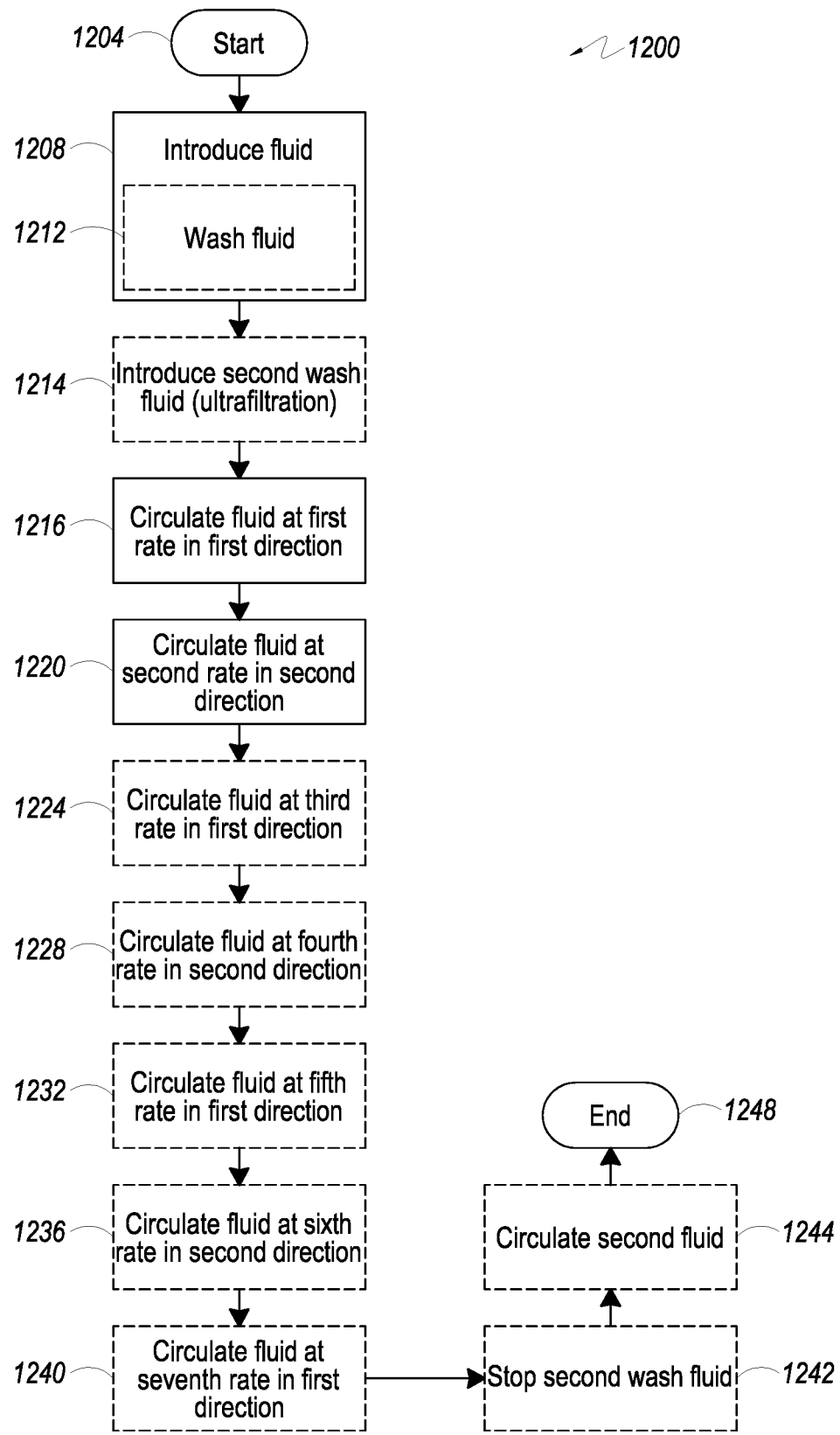
FIG. 12 illustrates a flow for a process of coating a bioreactor according to another embodiment.

Referring now to FIG. 11, a cross section 1100 (perpendicular to a central axis) of a bioreactor (e.g., bioreactor 100, 501, and/or 601) is shown. The cross section 1100 illustrates a plurality of hollow fibers 1108 which may be within a housing 1104. The cross section 1100 is taken from one end of a bioreactor and illustrates, in addition to the hollow fibers 1108 a matrix material 1128 (which may be referred to above as potting material) that holds the hollow fibers 1108 together.

Also shown in FIG. 11 are zones 1112, 1116, 1120 and 1124. These zones represent fibers that may have fluid circulating through them at different flow rates. Without being bound by theory, it is believed that circulation at relatively high flow rates, such as rates that may be used in circulation steps 1016 and/or 1020 (FIG. 10) may primarily flow through fibers in zone 1112. It is believed that the higher flow rates do not allow fluid to disperse enough to flow evenly into the hollow fibers in the outer zones. As the flow rate is reduced, such as in steps 1024, 1028, 1032, 1036, 1040, 1044, and 1048 it is believed that the fluid may disperse into hollow fibers in outer zones, such as 1116, 1120 and 1124.

It is believed that having steps 1016, 1020, 1024, 1028, 1032, 1036, 1040, 1044, and 1048 circulate at different flow rates, allows the fluid to flow through more of the hollow fibers 1108 than if just a single flow rate would be used. In one embodiment of a process that follows flow chart 1000, at steps 1016 and 1020 (at the flow rates described above), fluid may flow mainly through the hollow fibers in zone 1012. At steps 1024 and 1028 (at the flow rates described above), fluid may flow mainly through the hollow fibers in zones 1112 and 1116.

At steps 1032 and 1136 (at the flow rates described above), fluid may flow mainly through the hollow fibers in zone 1112, 1116, and 1120 because the rate is slower and the fluid may disperse more. At step 1040 (at the flow rates described above), fluid may flow through the hollow fibers in zones 1112, 1116, 1120, and 1124 because the flow rate is yet slower and fluid may disperse even more. Thus, it is believe that fluid with the reagent may flow into more of the hollow fibers using a sequence of different flow rates, than if a single high flow rate circulation is used.

Furthermore, it is also believed that the different flow rates may also affect the longitudinal distribution of the reagent along the bioreactor, e.g., along a hollow fiber. That is, a higher flow rate may allow the reagent to flow further along inside a hollow fiber. For example, at a higher flow rate, the reagent being carried by fluid may reach beyond half the length of the hollow fiber. At a lower flow rate, the reagent being carried by fluid may reach half the length of the hollow fiber. At even a lower flow rate, the reagent being carried by fluid may reach less than half the length of the hollow fiber. Accordingly, in some embodiments, it is believed that the use of different flow rates may provide some improvement in longitudinal distribution of the reagent along the length of the bioreactor, e.g., a hollow fiber.

Moreover, it is believed that the continuous addition of wash fluid (starting at step 1014 and ending at step 1042), to create ultrafiltration conditions, further promotes the coating of growth surfaces with the coating reagent. For example, as described above, the ultrafiltration moves the coating reagent toward an inside surface of hollow fiber walls, which may shorten the coating process, in addition to the more complete/uniform distribution of the coating agent provided by the other steps of flow 1000.

As noted above, steps in flow 1000 may be performed for predetermined periods of time. In embodiments, flow 1000 is designed to be performed within a period of time, e.g., 28 minutes, 56 minutes, 60 minutes, 90 minutes, and 120 minutes. For example, in embodiments, the predetermined period of times may be selected so that substantially all (or most) of the steps of flow 1000 may be performed in less than 90 minutes, such as less than 80 minutes, less than 70 minutes, less than 60 minutes, less than 50 minutes, less than 40 minutes, or even less than 30 minutes. In some embodiments, the steps of flow 1000 may be performed in greater than 10 minutes, greater than 20 minutes, greater than 30 minutes, greater than 40 minutes, or greater than 50 minutes. In selecting the periods of time, embodiments provide for each period to be the same in duration. In other embodiments, each period of time may have a different duration. In yet other embodiments, some periods of time may have the same duration while others have different durations. These are merely some examples and flow 1000 is not necessarily limited to being performed during any specific duration.

In one specific embodiment, flow 1000 may provide for performing each of steps 1016 through 1040 in less than 30 minutes. As one example, each of the steps may be performed for 4 minutes resulting in a 28 minute coating process. As yet another example, each of steps 1016 through 1040 may be performed for 8 minutes resulting in a 56 minute coating process. These are merely some non-limiting examples.

Referring now to flow 1200, it starts at step 1204 and proceeds to step 1208 where fluid that includes a reagent may be introduced into a cell expansion system and a bioreactor such as bioreactors 100, 501, and/or 601. In embodiments, step 1208 may be similar to step 808 and involve activating one or more pumps (564, 664) to introduce fluid with the reagent from a bag (562) or connection point (662) into a fluid flow path.

As part of introducing the fluid with the reagent into the cell expansion system, step 1208 may involve optional step 1212, where a wash fluid (e.g., PBS) may be used to chase the reagent from parts of the CES. For example, the wash fluid may move any reagent left behind in an ARC, such as ARC 556/656. The wash fluid may chase any lingering reagent into the bioreactor and/or a fluid flow path associated with the bioreactor e.g., 502/602.

Flow 1200 then passes to step 1214 where a second wash fluid may be introduced into the bioreactor. In embodiments, step 1214 may involve activating a pump, such as pumps 554,654 to introduce the second wash fluid from a bag (562) or connection point (662) into a fluid flow path and into the bioreactor (100, 501, and/or 601). In embodiments, the second wash fluid is introduced to create conditions for ultrafiltration, as described above. Ultrafiltration allows proteins or molecules (e.g., the coating reagent) that are too large to pass through the pores 818 (FIG. 8) of a hollow fiber 812 (FIG. 8) to adhere to the bioreactor fiber 812 and thus coat the walls while the solution flows through the pores 818. Where the solution flows through the pores 818 of the fiber 812 from the IC 816 to the EC side 820, positive ultrafiltration may result in the deposit of the coating agent or reagent on the inner walls, or IC side 816, of the fibers. In embodiments, the second wash fluid introduced at step 1214 may be continuously introduced as steps 1216 through 1240 are performed.

Flow 1200 passes to step 1216 where fluid that includes a reagent may be circulated through a bioreactor such as bioreactors 100, 501, and/or 601. In embodiments, step 1216 may involve activating one or more pumps to circulate fluid with the reagent through the bioreactor. For example, an IC circulation pump (e.g., 512 or 612) may be activated to circulate fluid through the IC side of a bioreactor at a first circulation flow rate. In at least one embodiment, fluid may pass through hollow fibers (e.g., the lumen). Step 1216 may involve circulating fluid at a first flow rate. The first flow rate may in embodiments be one of the first flow rates described above with respect to step 1016 (FIG. 10). Step 1216 may be performed for a first predetermined period of time. The first period of time may, in some embodiments, be one of the first periods of time described above with respect to step 1016 (FIG. 10).

In some embodiments, step 1216 may involve circulation in a specific direction. In other words, in some embodiments, step 1216 may involve activating a pump such as IC circulation pump (e.g., 512 or 612) in a specific direction, e.g., a counter clockwise or a clockwise direction. As one example, referring now to FIG. 6, step 1216 may involve activating pump 612 to circulate fluid through path 602 in a counter clock wise direction. That is, fluid may enter through port 601A and exit through port 601B.

Flow 1200 passes to step 1220, where fluid with the reagent is circulated at a second flow rate. In embodiments, the second flow rate may be one of the second flow rates described above with respect to step 1020 (FIG. 10). Step 1220 may be performed for a second predetermined period of time, which may be one of the second predetermined periods of time described above with respect to step 1020 (FIG. 10).

In some embodiments, step 1220 may involve circulation in a specific direction, such as a second direction opposite the first direction. Step 1220 may involve activating a pump such as IC circulation pump (e.g., 512 or 612) in a direction, e.g., a counter clockwise or a clockwise, opposite the first direction. Continuing with the example above, step 1216 may involve activating pump 612 to circulate fluid through path in a counter clock wise direction. Step 1220 may involve activating pump 612 to circulate fluid through path 602 in a clock wise direction. That is, fluid may enter through port 601B and exit through port 601A.

Flow 1200 then passes to optional step 1224, where fluid with the reagent is circulated at a third flow rate. In embodiments, the third flow rate may be one of the third flow rates described above with respect to step 1024 (FIG. 10). Step 1224 may be performed for a third predetermined period of time, which may be one of the third predetermined periods of time described above with respect to step 1024 (FIG. 10).

In some embodiments, step 1224 may involve circulation in a specific direction, such as the first direction. Step 1224 may involve activating a pump such as IC circulation pump (e.g., 512 or 612) in a direction, e.g., a counter clockwise or a clockwise. Continuing with the example above, step 1224 may involve activating pump 612 to circulate fluid through path in a counter clock wise direction. That is, fluid may enter through port 601A and exit through port 601B.

Flow 1200 then passes to optional step 1228, where fluid with the reagent is circulated at a fourth flow rate. In embodiments, the fourth flow rate may be one of the fourth flow rates described above with respect to step 1028 (FIG. 10). Step 1228 may be performed for a fourth predetermined period of time, which may be one of the fourth predetermined periods of time described above with respect to step 1028 (FIG. 10).

In some embodiments, step 1228 may involve circulation in a specific direction, such as opposite the first direction. Step 1228 may involve activating a pump such as IC circulation pump (e.g., 512 or 612) in a direction, e.g., a counter clockwise or a clockwise. Continuing with the example above, step 1228 may involve activating pump 612 to circulate fluid through path 602 in a clock wise direction. That is, fluid may enter through port 601B and exit through port 601A.

Flow 1200 then passes to optional step 1232, where fluid with the reagent is circulated at a fifth flow rate. In embodiments, the fifth flow rate may be one of the fifth flow rates described above with respect to step 1032 (FIG. 10). Step 1232 may be performed for a fifth predetermined period of time, which may be one of the fifth predetermined periods of time described above with respect to step 1032 (FIG. 10).

In some embodiments, step 1232 may involve circulation in a specific direction, such as the first direction. Step 1232 may involve activating a pump such as IC circulation pump (e.g., 512 or 612) in a direction, e.g., a counter clockwise or a clockwise. Continuing with the example above, step 1232 may involve activating pump 612 to circulate fluid through path 602 in a counter clock wise direction. That is, fluid may enter through port 601A and exit through port 601B.

Flow 1200 then passes to optional step 1236, where fluid with the reagent is circulated at a sixth flow rate. In embodiments, the sixth flow rate may be one of the sixth flow rates described above with respect to step 1036 (FIG. 10). Step 1236 may be performed for a sixth predetermined period of time, which may be one of the sixth predetermined periods of time described above with respect to step 1036 (FIG. 10).

In some embodiments, step 1236 may involve circulation in a specific direction, such as opposite the first direction. Step 1236 may involve activating a pump such as IC circulation pump (e.g., 512 or 612) in a direction, e.g., a counter clockwise or a clockwise. Continuing with the example above, step 1236 may involve activating pump 612 to circulate fluid through path 602 in a clock wise direction. That is, fluid may enter through port 601B and exit through port 601A.

Flow 1200 then passes to optional step 1240, where fluid with the reagent is circulated at a seventh flow rate. In embodiments, the seventh flow rate may be one of the seventh flow rates described above with respect to step 1040 (FIG. 10). Step 1240 may be performed for a seventh predetermined period of time, which may be one of the seventh predetermined periods of time described above with respect to step 1040 (FIG. 10).

In some embodiments, step 1240 may involve circulation in a specific direction, such as the first direction. Step 1240 may involve activating a pump such as IC circulation pump (e.g., 512 or 612) in a direction, e.g., a counter clockwise or a clockwise. Continuing with the example above, step 1240 may involve activating pump 612 to circulate fluid through path 602 in a counter clock wise direction. That is, fluid may enter through port 601A and exit through port 601B.

Flow 1200 then passes to step 1242 where introduction of the second wash fluid into the bioreactor is stopped. In embodiments, step 1242 may involve deactivating a pump, such as pump 554, 654 to stop the introduction of the second wash fluid into the fluid flow path and into the bioreactor (100, 501, and/or 601). In embodiments, stopping the introduction of the second wash fluid stops the process of ultrafiltration.

Flow 1200 then passes to step 1244, where a second fluid, that may not include the reagent, or have a lower concentration of the reagent, may be circulated through the bioreactor. In embodiments, step 1244 may be performed to wash any remaining reagent that has not coated a surface of the bioreactor out of the bioreactor and CES. As noted above, flow 1200 may be part of a larger process such as a process for growing and harvesting cells in a cell expansion system, such as flow 700. Therefore, in embodiments, step 1244 may be implemented as part of steps performed in the larger process, such as step 710 (FIG. 7). Flow 1200 then ends at 1248.

Without being bound by theory, it is believed that having steps 1216, 1220, 1224, 1228, 1232, 1236, 1240, 1244, and 1248 circulate at different flow rates, allows the fluid to flow through more of the hollow fibers e.g., 1108 (FIG. 11) than if just a single flow rate would be used. In one embodiment of a process that follows flow chart 1200, at steps 1216 and 1220 (at the flow rates described above), fluid may flow mainly through the hollow fibers in zone 1212. At steps 1224 and 1228 (at the flow rates described above), fluid may flow mainly through the hollow fibers in zones 1112 and 1116.

At steps 1232 and 1236 (at the flow rates described above), fluid may flow mainly through the hollow fibers in zone 1112, 1116, and 1120 because the rate is slower and the fluid may disperse more. At step 1240 (at the flow rates described above), fluid may flow through the hollow fibers in zones 1112, 1116, 1120, and 1124 because the flow rate is yet slower and fluid may disperse even more. Thus, it is believe that fluid with the reagent may flow into more of the hollow fibers using a sequence of different flow rates, than if a single high flow rate circulation is used.

As noted above, it is also believed that the different flow rates may also affect the longitudinal distribution of the reagent along the bioreactor, e.g., along a hollow fiber. That is, a higher flow rate may allow the reagent to flow further along inside a hollow fiber. For example, at a higher flow rate, the reagent being carried by fluid may reach beyond half the length of the hollow fiber. At a lower flow rate, the reagent being carried by fluid may reach half the length of the hollow fiber. At even a lower flow rate, the reagent being carried by fluid may reach less than half the length of the hollow fiber. Accordingly, in some embodiments, it is believed that the use of different flow rates may provide some improvement in longitudinal distribution of the reagent along the length of the bioreactor, e.g., a hollow fiber. Additionally, with the changing of directions provided for in flow 1200, the reagent may be distributed along the length of the hollow fibers from both sides of a hollow fiber. The combination of flow rate changes and changes in direction, may allow for more even distribution of the reagent along the length of a hollow fiber.

Moreover, it is believed that the continuous addition of wash fluid (starting at step 1214 and ending at step 1242), to create ultrafiltration conditions, further promotes the coating of growth surfaces with the coating reagent. For example, as described above, the ultrafiltration moves the coating reagent toward an inside surface of hollow fiber walls, which may shorten the coating process, in addition to the more complete/uniform distribution of the coating agent provided by the other steps of flow 1200.

As noted above, steps in flow 1200 may be performed for predetermined periods of time. In embodiments, flow 1200 is designed to be performed within a period of time, e.g., relatively quickly. For example, in embodiments, the predetermined period of times may be selected so that substantially all (or most) of the steps of flow 1200 may be performed in less than 90 minutes, such as less than 80 minutes, less than 70 minutes, less than 60 minutes, less than 50 minutes, less than 40 minutes, or even less than 30 minutes. In some embodiments, the steps of flow 800 may be performed in greater than 10 minutes, greater than 20 minutes, greater than 30 minutes, greater than 40 minutes, or greater than 50 minutes. In selecting the periods of time, embodiments provide for each period to be the same in duration. In other embodiments, each period of time may have a different duration. In yet other embodiments, some periods of time may have the same duration while others have different durations. These are merely some examples and flow 1200 is not necessarily limited to being performed during any specific duration.

In one specific embodiment, flow 1200 may provide for performing each of steps 1216 through 1240 in less than 30 minutes. As one example, each of the steps may be performed for 4 minutes resulting in a 28 minute coating process. As yet another example, each of steps 1216 through 1240 may be performed for 8 minutes resulting in a 56 minute coating process. These are merely some non-limiting examples.

Figure 13:
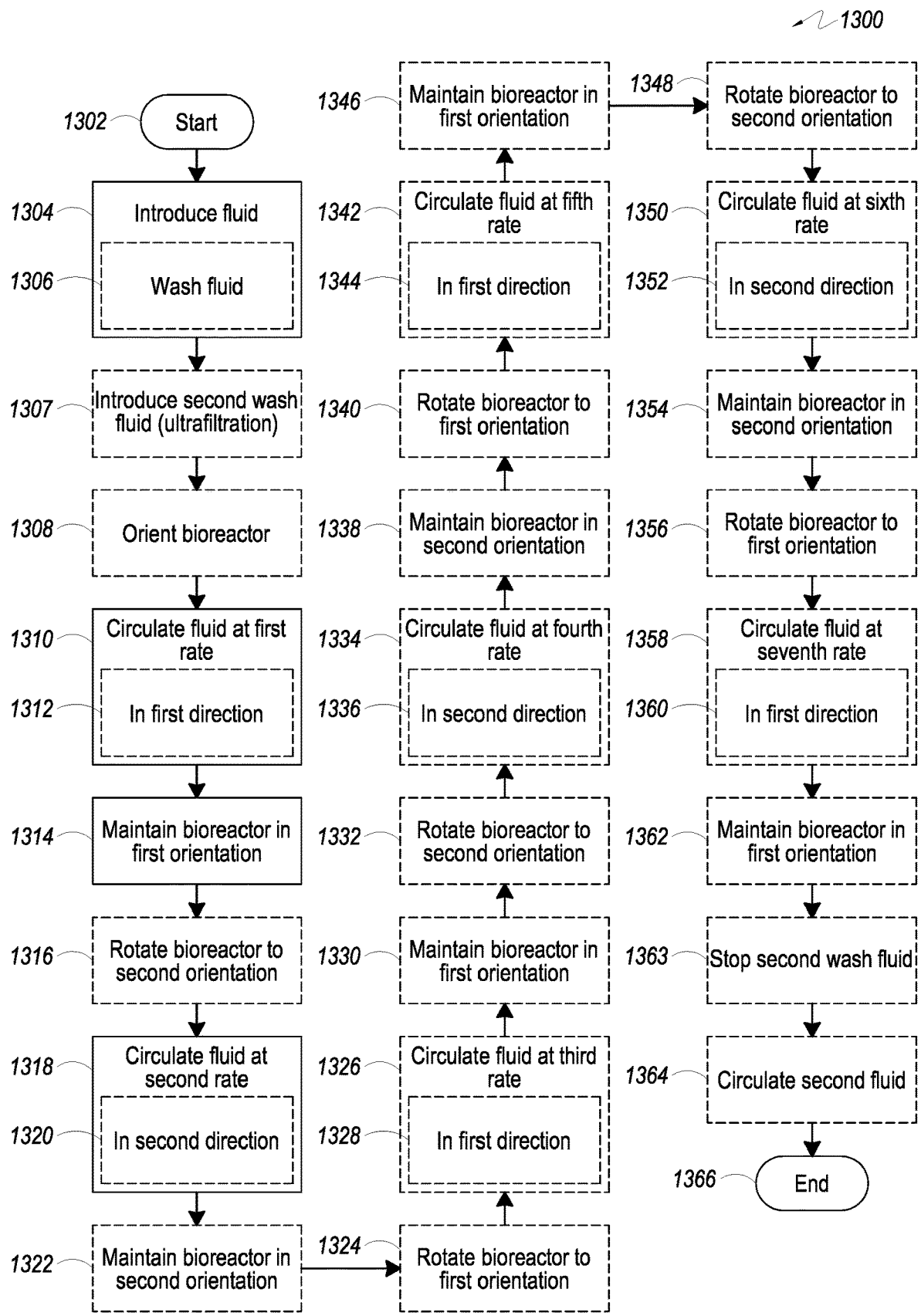
FIG. 13 illustrates a flow for a process of coating a bioreactor according to yet another embodiment.

Referring now to FIG. 13, flow 1300 starts at 1302 and passes to step 1304 where fluid that includes a reagent may be introduced into a cell expansion system and a bioreactor such as bioreactors 100, 300, 501, and/or 601. In embodiments, step 1304 may involve activating one or more pumps (564, 664) to introduce fluid with the reagent from a bag (562) or connection point (662) into a fluid flow path.

As part of introducing the fluid with the reagent into the cell expansion system, step 1304 may involve optional step 1306, where a wash fluid (e.g., PBS) may be used to chase the reagent from parts of the CES. For example, the wash fluid may move any reagent left behind in an ARC, such as ARC 556/656. The wash fluid may chase any lingering reagent into the bioreactor and/or a fluid flow path associated with the bioreactor e.g., 502/602.

Flow 1300 then passes to step 1307 where a second wash fluid may be introduced into the bioreactor. In embodiments, step 1307 may involve activating a pump, such as pumps 554, 654 to introduce the second wash fluid from a bag (562) or connection point (662) into a fluid flow path and into the bioreactor (100, 501, and/or 601). In embodiments, the second wash fluid is introduced to create conditions for ultrafiltration, as described above. Ultrafiltration allows proteins or molecules (e.g., the coating reagent) that are too large to pass through the pores 818 (FIG. 8) of a hollow fiber 812 (FIG. 8) to adhere to the bioreactor fiber 812 and thus coat the walls while the solution flows through the pores 818. Where the solution flows through the pores 818 of the fiber 812 from the IC 816 to the EC side 820, positive ultrafiltration may result in the deposit of the coating agent or reagent on the inner walls, or IC side 816, of the fibers. In embodiments, the second wash fluid introduced at step 1307 may be continuously introduced as steps 1308 through 1362 are performed.

Flow 1300 passes to step 1308 which may be performed to orient a bioreactor, e.g. bioreactor 100, 501, and/or 601, to an initial orientation. In embodiments, a bioreactor may already be oriented in an initial orientation, in which case step 1308 would not be performed. When performed, step 1308 may in some embodiments be performed by one or rotation mechanisms that may include one or more motors, gears, connectors, shafts, etc. that rotate the bioreactor to a first orientation. In embodiments, the orientation may be an initial horizontal orientation.

Figure 15:
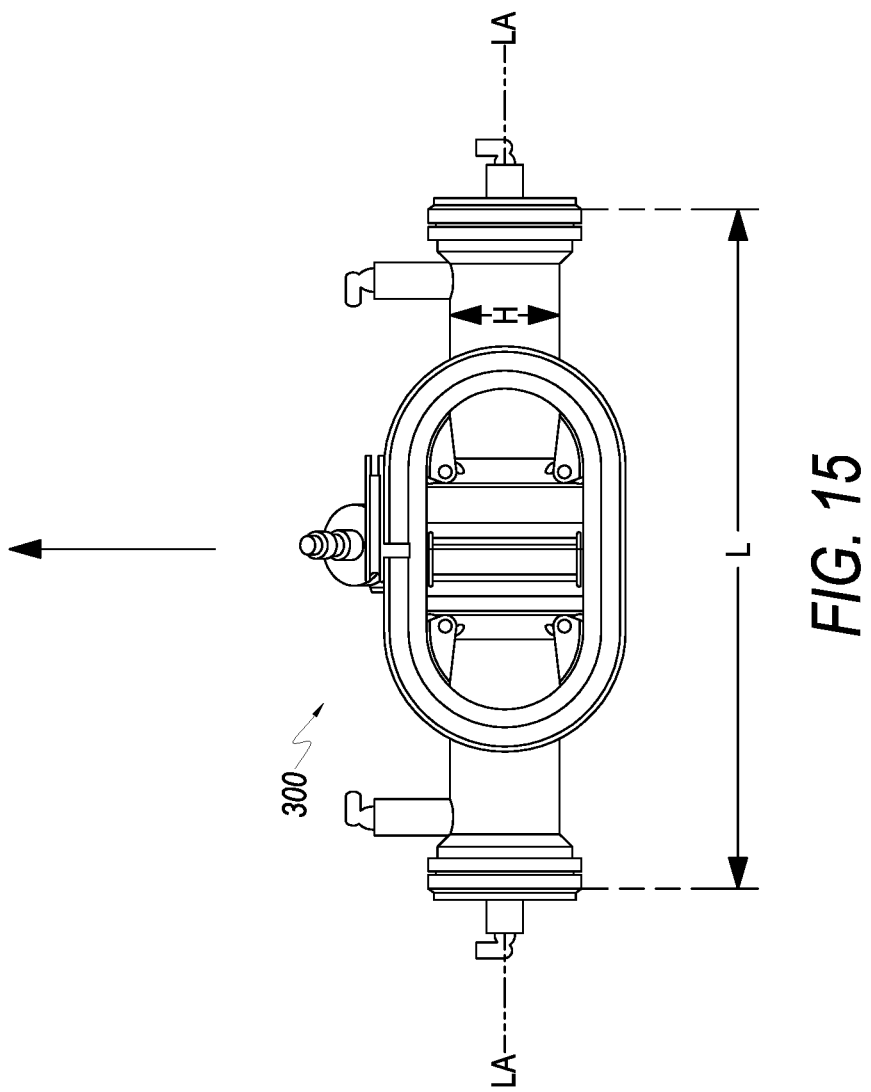
FIG. 15 illustrates a front elevation view of an embodiment of a bioreactor in a first orientation.
Figure 16:
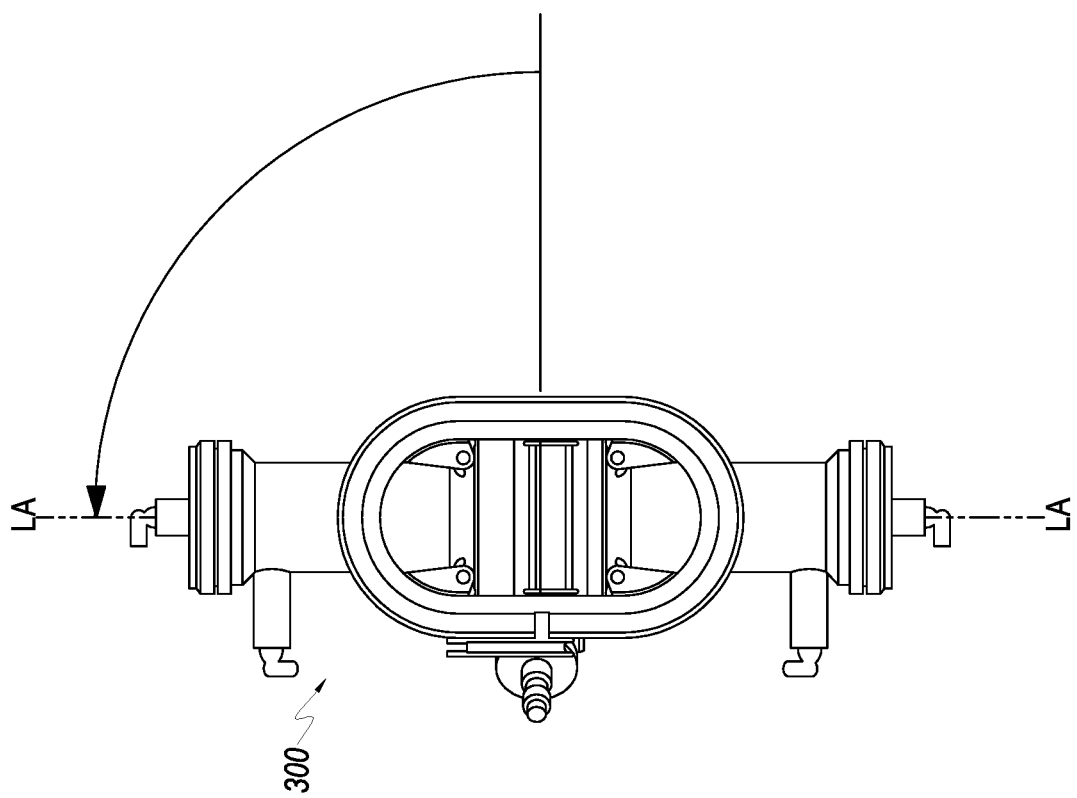
FIG. 16 illustrates a front elevation view of the bioreactor of FIG. 15, wherein the bioreactor is shown rotated about 90 degrees from the view of FIG. 15.
Figure 17:
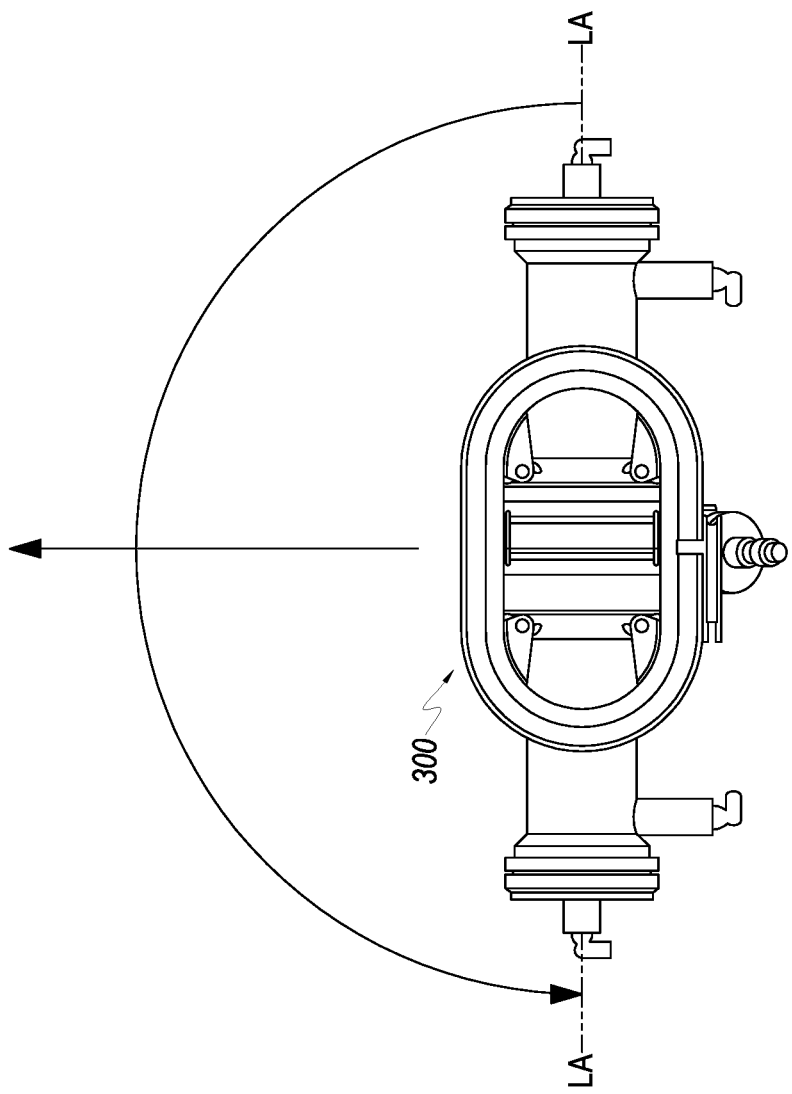
FIG. 17 is a front elevation view of the bioreactor of FIG. 15, wherein the bioreactor is shown rotated about 180 degrees from the view of FIG. 15.

Referring now to FIGS. 15-17, a bioreactor 300 (which in embodiments may be bioreactor 100, 501, and/or 601) is shown in different orientations. FIG. 15 illustrates the bioreactor 300 positioned in an initial orientation. As part of optional step 1308, bioreactor 300 may be oriented with its longitudinal axis LA-LA in a starting orientation, such as, for example, a first horizontal orientation as shown in FIG. 15.

Flow 1300 passes from optional step 1308 to step 1310 where fluid that includes a reagent may be circulated through a bioreactor such as bioreactors 100, 501, and/or 601. In embodiments, step 1310 may involve activating one or more pumps to circulate fluid with the reagent through the bioreactor. For example, an IC circulation pump (e.g., 512 or 612) may be activated to circulate fluid through the IC side of a bioreactor at a first circulation flow rate.

In at least one embodiment, fluid may pass through hollow fibers (e.g., the lumen). Step 1310 may involve circulating fluid at a first flow rate. The first flow rate may in embodiments be one of the first flow rates described above with respect to step 1016 (FIG. 10).

In other embodiments, fluid with the reagent may be circulated through the EC side of the bioreactor. Step 1310 may therefore, in embodiments, involve activating an EC circulation pump (e.g., 528 or 628) to circulate fluid through the EC side of bioreactor at a first circulation flow rate.

In embodiments, the reagent may be any protein, nutrient, or other material that is useful in creating conditions for expansion of cells. As described above, the reagent may be a protein that coats a surface in the bioreactor to which cell (e.g., adherent cells) may attach and grow. As one example, a glycoprotein (such as fibronectin, collagen, cryoprecipitate, etc.) may be the reagent that is circulated through a bioreactor, e.g., through the IC circuit of the bioreactor, to coat an inside surface of hollow fibers. The coating may promote the attachment of adherent cells that may later be added to the bioreactor and expanded in the bioreactor. This is merely one example and flow 1300 is not limited to this application.

In some embodiments, step 1310 may involve circulation in a specific direction. In other words, in some embodiments, step 1310 may involve activating a pump such as IC circulation pump (e.g., 512 or 612) in a first direction 1312, e.g., a counter clockwise or a clockwise direction. As one example, referring now to FIG. 6, step 1310 may involve activating pump 612 to circulate fluid through path 602 in a counter clock wise direction. That is, fluid may enter through port 601A and exit through port 601B.

Flow 1300 passes from step 1310 to step 1314 where the bioreactor is maintained in the first orientation, e.g., a horizontal orientation (FIG. 15). Step 1314 may be performed in combination with step 1310. In embodiments, the first period of time may be one of the first periods of time described above with respect to step 1016 (FIG. 10). Step 1314 may be performed in embodiments to provide time to allow the reagent to coat portions of the bioreactor. For example, when the bioreactor comprises hollow fibers, step 1314 may be performed to allow the reagent time to coat interior surfaces of the hollow fibers.

After step 1314, flow 1300 may pass to optional step 1316, where the bioreactor is rotated to a second orientation. In embodiments, the second orientation may be a horizontal orientation that is about 180 degrees from the original (e.g., first) orientation (e.g., FIG. 15). FIG. 13 illustrates bioreactor 300 rotated 90 degrees from the orientation shown in FIG. 15, with FIG. 17 illustrating bioreactor 300 rotated about 180 degrees from the orientation shown in FIG. 15. In embodiments, step 1316 may be performed to rotate the bioreactor to an orientation shown in FIG. 17 (e.g., a second horizontal orientation). If step 1316 is not performed, flow would pass from step 1314 to step 1318. In these embodiments, the bioreactor may remain in the first orientation (e.g., first horizontal orientation as shown in FIG. 15).

Flow passes to step 1318, wherein fluid with the reagent is circulated at a second flow rate, which may be less than the first flow rate. In embodiments, the second flow rate may be one of the second flow rates described above with respect to step 1020 (FIG. 10).

In some embodiments, step 1318 may involve circulation in a specific direction. In other words, in some embodiments, step 1318 may involve activating a pump such as IC circulation pump (e.g., 512 or 612) in a second direction 1320, e.g., a counter clockwise or a clockwise direction. Continuing with the example above, referring FIG. 6, step 1320 may involve activating pump 612 to circulate fluid through path 602 in a clock wise direction. That is, fluid may enter through port 601B and exit through port 601A.

Flow 1300 passes from step 1318 to optional step 1322 where the bioreactor is maintained in the second orientation, e.g., a second horizontal orientation (FIG. 17). Optional step 1322 may be performed in combination with optional step 1318. In embodiments, optional steps 1318 and 1322 may be performed for a second predetermined period of time. In embodiments, the second period of time may be one of the second periods of time described above with respect to step 1020 (FIG. 10). Step 1322 may be performed in embodiments to provide time to allow the reagent to coat portions of the bioreactor. For example, when the bioreactor comprises hollow fibers, step 1322 may be performed to allow the reagent time to coat interior surfaces of the hollow fibers.

After optional step 1322, flow 1300 may pass to optional step 1324, where the bioreactor is rotated back to the first orientation. In embodiments, the first orientation may be a horizontal orientation that is about the same as the original (e.g., first) orientation (e.g., FIG. 15).

Flow passes to step 1326, wherein fluid with the reagent is circulated at a third flow rate, which may be less than the second flow rate. In embodiments, the third flow rate may be one of the third flow rates described above with respect to step 1024 (FIG. 10).

In some embodiments, step 1326 may involve circulation in a specific direction. In other words, in some embodiments, step 1326 may involve activating a pump such as IC circulation pump (e.g., 512 or 612) in the first direction 1328 e.g., a counter clockwise or a clockwise direction. Continuing with the example above, referring to FIG. 6, step 1326 may involve activating pump 612 to circulate fluid through path 602 in a counter clock wise direction. That is, fluid may enter through port 601A and exit through port 601B.

Flow 1300 passes from step 1326 to optional step 1330 where the bioreactor is maintained in the first orientation, e.g., a first horizontal orientation (FIG. 15). Optional step 1330 may be performed in combination with optional step 1326. In embodiments, optional steps 1326 and 1330 may be performed for a third predetermined period of time. In embodiments, the third period of time may be one of the third periods of time described above with respect to step 1024 (FIG. 10). Step 1322 may be performed in embodiments to provide time to allow the reagent to coat portions of the bioreactor. For example, when the bioreactor comprises hollow fibers, step 1322 may be performed to allow the reagent time to coat interior surfaces of the hollow fibers.

After optional step 1326, flow 1300 may pass to optional step 1332, where the bioreactor is rotated back to the second orientation. In embodiments, the second orientation may be a horizontal orientation that is about 180 degrees from the first orientation (e.g., FIG. 17).

Flow 1300 then passes to optional step 1334, where fluid with the reagent is circulated at a fourth flow rate, which may be less than the third flow rate. In embodiments, the fourth flow rate may be one of the fourth flow rates described above with respect to step 1028 (FIG. 10).

In some embodiments, step 1334 may involve circulation in a specific direction. In other words, in some embodiments, step 1334 may involve activating a pump such as IC circulation pump (e.g., 512 or 612) in the second direction 1336 e.g., a counter clockwise or a clockwise direction. Continuing with the example above, referring to FIG. 6, step 1334 may involve activating pump 612 to circulate fluid through path 602 in a clock wise direction. That is, fluid may enter through port 601B and exit through port 601A.

Flow 1300 passes from step 1334 to optional step 1338 where the bioreactor is maintained in the second orientation, e.g., a second horizontal orientation (FIG. 17). Optional step 1338 may be performed in combination with optional step 1334. In embodiments, optional steps 1334 and 1338 may be performed for a fourth predetermined period of time. In embodiments, the fourth period of time may be one of the second periods of time described above with respect to step 1028 (FIG. 10). Step 1338 may be performed in embodiments to provide time to allow the reagent to coat portions of the bioreactor. For example, when the bioreactor comprises hollow fibers, step 1338 may be performed to allow the reagent time to coat interior surfaces of the hollow fibers.

After optional step 1338, flow 1300 may pass to optional step 1340, where the bioreactor is rotated back to the first orientation. In embodiments, the first orientation may be a horizontal orientation that is about the same as the original (e.g., first) orientation (e.g., FIG. 15).

Flow passes to step 1342, wherein fluid with the reagent is circulated at a fifth flow rate, which may be less than the fourth flow rate. In embodiments, the fifth flow rate may be one of the fifth flow rates described above with respect to step 1032 (FIG. 10).

In some embodiments, step 1342 may involve circulation in a specific direction. In other words, in some embodiments, step 1342 may involve activating a pump such as IC circulation pump (e.g., 512 or 612) in the first direction 1344 e.g., a counter clockwise or a clockwise direction. Continuing with the example above, referring to FIG. 6, step 1342 may involve activating pump 612 to circulate fluid through path 602 in a counter clock wise direction. That is, fluid may enter through port 601A and exit through port 601B.

Flow 1300 passes from step 1342 to optional step 1346 where the bioreactor is maintained in the first orientation, e.g., a first horizontal orientation (FIG. 15). Optional step 1346 may be performed in combination with optional step 1342. In embodiments, optional steps 1342 and 1346 may be performed for a fifth predetermined period of time. In embodiments, the fifth period of time may be one of the second periods of time described above with respect to step 1032 (FIG. 10). Step 1346 may be performed in embodiments to provide time to allow the reagent to coat portions of the bioreactor. For example, when the bioreactor comprises hollow fibers, step 1346 may be performed to allow the reagent time to coat interior surfaces of the hollow fibers.

After optional step 1346, flow 1300 may pass to optional step 1348, where the bioreactor is rotated back to the second orientation. In embodiments, the second orientation may be a horizontal orientation that is about 180 degrees from the original (e.g., first) orientation (e.g., FIG. 17).

Flow 1300 then passes to optional step 1350, where fluid with the reagent is circulated at a sixth flow rate, which may be less than the fifth flow rate. In embodiments, the fifth flow rate may be one of the fifth flow rates described above with respect to step 1032 (FIG. 10).

In some embodiments, step 1350 may involve circulation in a specific direction. In other words, in some embodiments, step 1350 may involve activating a pump such as IC circulation pump (e.g., 512 or 612) in the second direction 1352 e.g., a counter clockwise or a clockwise direction. Continuing with the example above, referring to FIG. 6, step 1350 may involve activating pump 612 to circulate fluid through path 602 in a clock wise direction. That is, fluid may enter through port 601B and exit through port 601A.

Flow 1300 passes from step 1350 to optional step 1354 where the bioreactor is maintained in the second orientation, e.g., a second horizontal orientation (FIG. 17). Optional step 1354 may be performed in combination with optional step 1350. In embodiments, optional steps 1350 and 1354 may be performed for a sixth predetermined period of time. In embodiments, the sixth period of time may be one of the sixth periods of time described above with respect to step 1036 (FIG. 10). Step 1354 may be performed in embodiments to provide time to allow the reagent to coat portions of the bioreactor. For example, when the bioreactor comprises hollow fibers, step 1354 may be performed to allow the reagent time to coat interior surfaces of the hollow fibers.

After optional step 1346, flow 1300 may pass to optional step 1348, where the bioreactor is rotated back to the first orientation. In embodiments, the first orientation may be a horizontal orientation that is substantially the same as the original (e.g., first) orientation (e.g., FIG. 15).

Flow passes to step 1358, wherein fluid with the reagent is circulated at a seventh flow rate, which may be less than the sixth flow rate. In embodiments, the seventh flow rate may be one of the fifth flow rates described above with respect to step 1040 (FIG. 10).

In some embodiments, step 1358 may involve circulation in a specific direction. In other words, in some embodiments, step 1358 may involve activating a pump such as IC circulation pump (e.g., 512 or 612) in the first direction 1360 e.g., a counter clockwise or a clockwise direction. Continuing with the example above, referring to FIG. 6, step 1358 may involve activating pump 612 to circulate fluid through path 602 in a counter clock wise direction. That is, fluid may enter through port 601A and exit through port 601B.

Flow 1300 passes from step 1358 to optional step 1362 where the bioreactor is maintained in the first orientation, e.g., a first horizontal orientation (FIG. 15). Optional step 1362 may be performed in combination with optional step 1358. In embodiments, optional steps 1358 and 1362 may be performed for a seventh predetermined period of time. In embodiments, the seventh period of time may be one of the seventh periods of time described above with respect to step 1040 (FIG. 10). Step 1362 may be performed in embodiments to provide time to allow the reagent to coat portions of the bioreactor. For example, when the bioreactor comprises hollow fibers, step 1362 may be performed to allow the reagent time to coat interior surfaces of the hollow fibers.

Flow 1300 then passes to step 1363 where introduction of the second wash fluid into the bioreactor is stopped. In embodiments, step 1363 may involve deactivating a pump, such as pump 554, 654 to stop the introduction of the second wash fluid into the fluid flow path and into the bioreactor (100, 501, and/or 601). In embodiments, stopping the introduction of the second wash fluid stops the process of ultrafiltration.

Flow 1300 then passes to step 1364, where a second fluid, that may not include the reagent, or have a lower concentration of the reagent, may be circulated through the bioreactor. In embodiments, step 1364 may be performed to wash any remaining reagent that has not coated a surface of the bioreactor out of the bioreactor and CES. As noted above, flow 1300 may be part of a larger process such as a process for growing and harvesting cells in a cell expansion system, such as flow 700. Therefore, in embodiments, step 1364 may be implemented as part of steps performed in the larger process, such as step 710 (FIG. 7). Flow 1300 then ends at 1366.

Without being bound by theory, it is believed that having steps 1310, 1318, 1326, 1334, 1342, 1350, and 1358 circulate at different flow rates, allows the fluid to flow through more of the hollow fibers e.g., 1108 (FIG. 11) than if just a single flow rate would be used. In one embodiment of a process that follows flow chart 1300, at steps 1310 and 1318 (at the flow rates described above), fluid may flow mainly through the hollow fibers in zone 1112. At steps 1326 and 1334 (at the flow rates described above), fluid may flow mainly through the hollow fibers in zones 1112 and 1116.

At steps 1342 and 1350 (at the flow rates described above), fluid may flow mainly through the hollow fibers in zone 1112, 1116, and 1120 because the rate is slower and the fluid may disperse more. At step 1358 (at the flow rates described above), fluid may flow through the hollow fibers in zones 1112, 1116, 1120, and 1124 because the flow rate is yet slower and fluid may disperse even more. Thus, it is believe that fluid with the reagent may flow into more of the hollow fibers using a sequence of different flow rates, than if a single high flow rate circulation is used.

As noted above, it is also believed that the different flow rates may also affect the longitudinal distribution of the reagent along the bioreactor, e.g., along a hollow fiber. That is, a higher flow rate may allow the reagent to flow further along inside a hollow fiber. For example, at a higher flow rate, the reagent being carried by fluid may reach beyond half the length of the hollow fiber. At a lower flow rate, the reagent being carried by fluid may reach half the length of the hollow fiber. At even a lower flow rate, the reagent being carried by fluid may reach less than half the length of the hollow fiber. Accordingly, in some embodiments, it is believed that the use of different flow rates may provide some improvement in longitudinal distribution of the reagent along the length of the bioreactor, e.g., a hollow fiber. Additionally, with the changing of directions provided for in flow 1300, the reagent may be distributed along the length of the hollow fibers from both sides of a hollow fiber. The combination of flow rate changes and changes in direction, may allow for more even distribution of the reagent along the length of a hollow fiber.

Furthermore, flow 1300 provides for rotation of the bioreactor, as described above. It is also believed that rotation of the bioreactor, in addition to changes in direction and flow rates, provides a process where the reagent may be distributed/coated on hollow fibers more completely and/or uniformly.

Moreover, it is believed that the continuous addition of wash fluid (starting at step 1307 and ending at step 1363), to create ultrafiltration conditions, further promotes the coating of growth surfaces with the coating reagent. For example, as described above, the ultrafiltration moves the coating reagent toward an inside surface of hollow fiber walls, which may shorten the coating process, in addition to the more complete/uniform distribution of the coating agent provided by the other steps of flow 1300.

As noted above, steps in flow 1300 may be performed for predetermined periods of time. In embodiments, flow 1300 is designed to be performed within a period of time, e.g., relatively quickly. For example, in embodiments, the predetermined period of times may be selected so that substantially all (or most) of the steps of flow 1300 may be performed in less than 90 minutes, such as less than 80 minutes, less than 70 minutes, less than 60 minutes, less than 50 minutes, less than 40 minutes, or even less than 30 minutes. In some embodiments, the steps of flow 800 may be performed in greater than 10 minutes, greater than 20 minutes, greater than 30 minutes, greater than 40 minutes, or greater than 50 minutes. In selecting the periods of time, embodiments provide for each period to be the same in duration. In other embodiments, each period of time may have a different duration. In yet other embodiments, some periods of time may have the same duration while others have different durations. These are merely some examples and flow 1300 is not necessarily limited to being performed during any specific duration.

In one specific embodiment, flow 1300 may provide for performing all of steps 1310, 1318, 1326, 1334, 1342, 1350, and 1358 in less than 30 minutes. As one example, each of the steps may be performed for 4 minutes resulting in a 28 minute coating process. As yet another example, each of steps 1310, 1318, 1326, 1334, 1342, 1350, and 1358 may be performed for 8 minutes resulting in a 56 minute coating process. These are merely some non-limiting examples.

Figure 14:
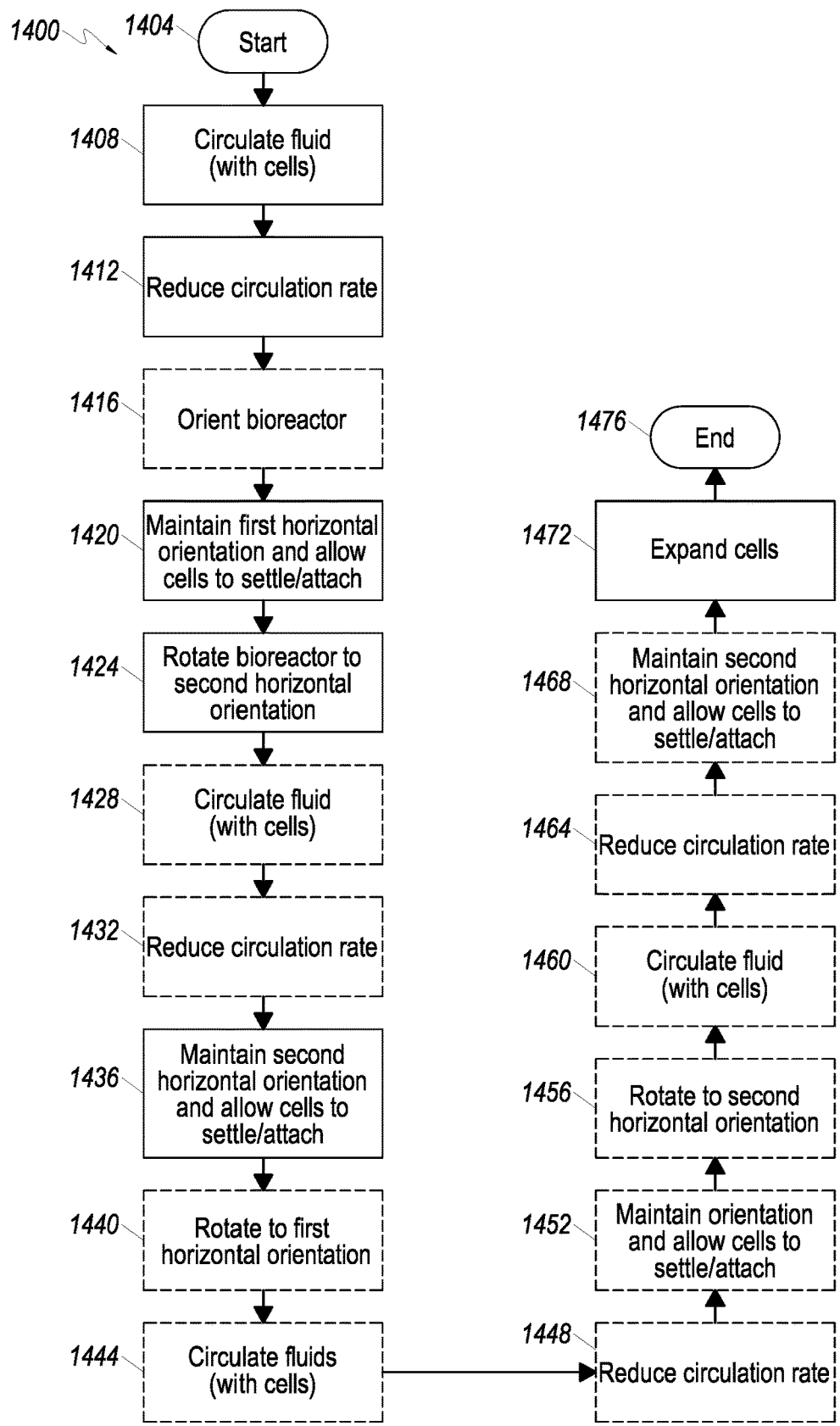
FIG. 14 is a flow chart of a process for loading, distributing, attaching, and expanding cells according to some embodiments.

Turning now to FIG. 14, flow 1400 begins at 1404 and passes to step 1408 where fluid that includes cells may be circulated through a bioreactor such as bioreactors 100, 300, 501, 601. In embodiments, step 1408 may involve activating one or more pumps to circulate fluid through the bioreactor 100, 300, 501, 601. For example, an IC circulation pump (e.g., 512 or 612) may be activated to circulate fluid through the IC side of the bioreactor at a first circulation flow rate. In at least one embodiment, fluid carrying the cells may pass through hollow fibers of the bioreactor from the IC side to the EC side. In other embodiments, cells may be loaded into the EC side of the bioreactor and have the fluid carrying the cells pass from the EC side to the IC side. In these embodiments, an EC circulation pump (e.g., 528, 628) may be activated to circulate fluid through the EC side of bioreactor at a first circulation flow rate.

In embodiments, the first circulation flow rate may be a relatively high flow rate. In embodiments, the first circulation flow rate may be less than about 500 ml/min, less than about 400 ml/min, or even less than about 300 ml/min. In other embodiments, the first circulation rate may be greater than about 50 ml/min, greater than about 100 ml/min, or even greater than about 150 ml/min. In one embodiment, the first circulation flow rate is between about 100 ml/min and about 300 ml/min, such as about 200 ml/min.

Step 1408 may in some embodiments involve also rotating the bioreactor in a particular sequence to facilitate distribution of the cells through the bioreactor and circulation paths of the CES to which the bioreactor may be fluidly associated. In other embodiments, the circulating step 1408 may involve rotating the bioreactor for some periods of time, but maintaining the bioreactor stationary for other periods of time.

After step 1408, the fluid circulation rate is reduced at step 1412. The circulation rate may be reduced to about zero (0) ml/min, or in other embodiments may be reduced to a rate that is above zero (0) ml/min but still allows cells to settle and attach to the bioreactor e.g., an inside surface of hollow fibers of bioreactor. In embodiments, step 1412 may involve stopping or turning off one or more pumps used in step 1408 to circulate the fluid.

Flow passes from step 1412 to optional step 1416, which may be performed to orient a bioreactor, e.g. bioreactor to an initial orientation. In embodiments, a bioreactor may already be oriented in an initial orientation, whereby step 1416 would not be performed. When performed, step 1416 may in some embodiments be performed by one or more motors.

Referring now to FIGS. 15-19, a bioreactor 300 is shown in FIG. 15 positioned in an initial orientation. As part of optional step 1416, bioreactor 300 may be oriented with its longitudinal axis LA-LA in a starting orientation, such as, for example, a first horizontal orientation as shown in FIG. 15.

Flow passes from 1416, to step 1420 where the bioreactor is maintained at a first orientation to allow cells to settle and in some embodiments attach to a first portion of bioreactor 300. Step 1420 may be performed for a first predetermined period of time.

Figure 20A:
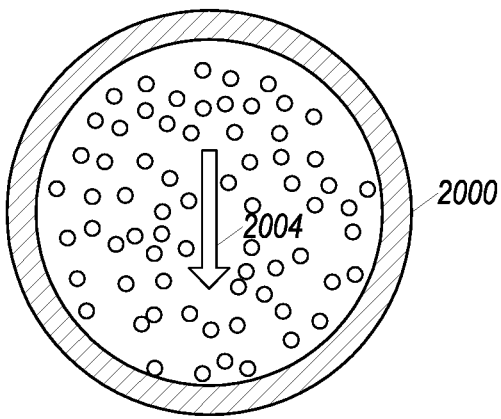
FIGS. 20A-20D illustrate a cross section (perpendicular to a central axis) of a hollow fiber that may be part of a bioreactor as it progresses through steps of a process for distributing, attaching, and expanding cells in the bioreactor according to another embodiment.
Figure 20B:
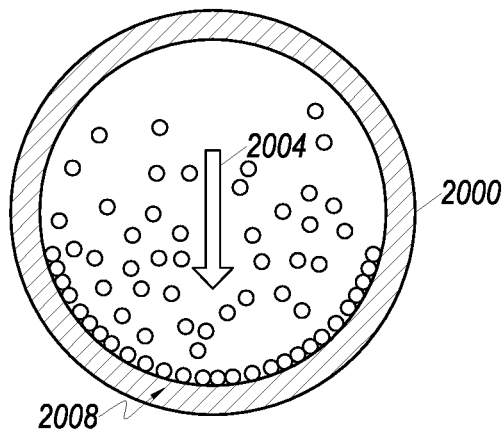
Figure 20C:
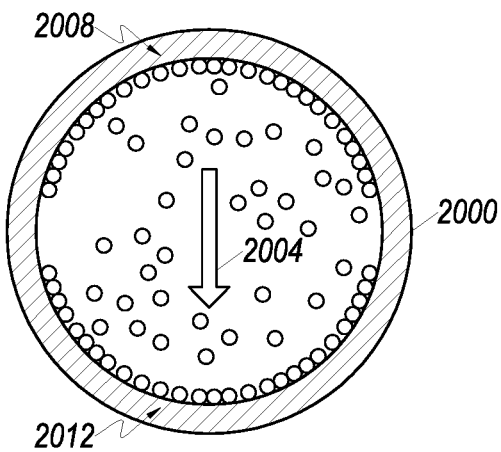
Figure 20D:
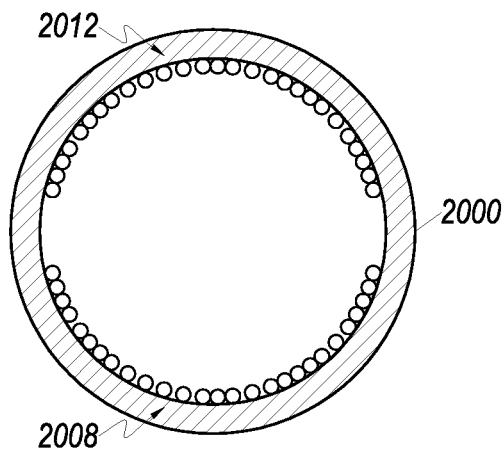
Figure 21A:
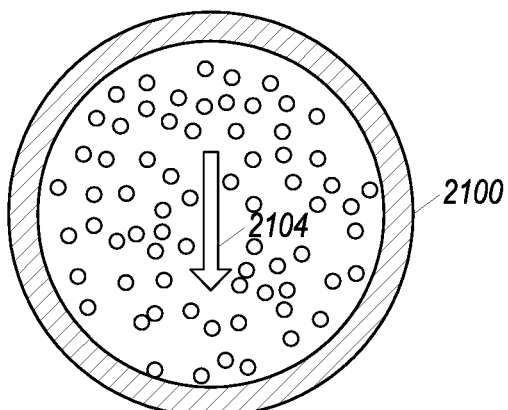
FIG. 21A-21F illustrate a cross section (perpendicular to a central axis) of a hollow fiber that may be part of a bioreactor as it progresses through steps of a process for distributing attaching and expanding cells in the bioreactor according to yet another embodiment.

Referring now to FIGS. 20A-20D and FIGS. 21A-21F these figures illustrate a cross-section of a hollow fiber 2000 (taken perpendicular to a central axis of the hollow fiber 2000 and a central axis of bioreactor 300) that may be one of the hollow fibers of bioreactor 300. These figures illustrate the possible locations of cells within the hollow fibers during some steps of flow chart 1400. As illustrated in FIG. 20A, before the circulation rate is reduced at step 1412, cells within individual hollow fiber 2000 may be distributed, in embodiments evenly, throughout the volume of hollow fiber 2000. When the circulation rate is reduced, the cells may begin to be influenced by gravity 2004 and begin to settle. FIG. 21A also illustrates a similar situation with respect to a hollow fiber 2100 and gravity 2104.

Figure 21B:
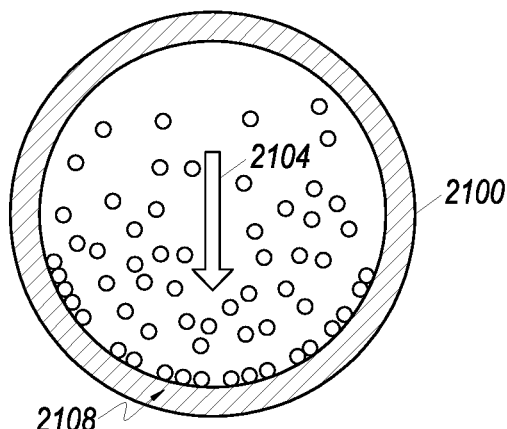

In embodiments, with the bioreactor 300 in the first horizontal orientation (FIG. 15), the cells within bioreactor 300 are allowed to settle onto a first portion of the bioreactor. As illustrated in FIGS. 20B and 21B, the first portion of bioreactor 300 may include at least a portion 2008 of hollow fiber 2000 and/or portion 2108 in hollow fiber 2100. In embodiments, the cells will be allowed to settle for a first predetermined period of time that may be selected to not only allow the cells to settle, but also to attach to portion 2008 of the hollow fiber 2000 (and 2108 of hollow fiber 2100).

In some embodiments, the first predetermined period of time may be long enough in duration to allow the cells to settle and attach to portion 2008 and 2108. In these embodiments, the cells may only need to travel the distance of the inner diameter of hollow fiber 2000 or 2100. For example, in embodiments where the hollow fiber has an inner diameter of between about 150 microns and about 300 microns, the first predetermined period of time may be less than about 20 minutes, less than about 15 minutes, or even less than about 10 minutes. In other embodiments, the first predetermined period of time may be greater than about 1 minute, greater than about 2 minutes, greater than about 3 minutes, or even greater than about 4 minutes. In one embodiment, the first period of time may be between about 3 minutes and about 8 minutes, such as about 5 minutes.

After step 1420, flow passes to step 1424, where the bioreactor 300 is rotated to a second horizontal orientation that is about 180 degrees from the first horizontal orientation. As shown in FIGS. 15-17, the bioreactor may be rotated by first being rotated from its first horizontal orientation (FIG. 15) to a first vertical orientation, which is about 90 degrees from the first horizontal orientation, e.g. axis LA LA in a vertical orientation (FIG. 16). Bioreactor 300 may then be rotated another 90 degrees (FIG. 17) to complete the rotation to the second horizontal orientation. Step 1424 may in some embodiments be performed by one or more motors connected to bioreactor 300. These motors may be part of a rocking device.

Figure 21C:
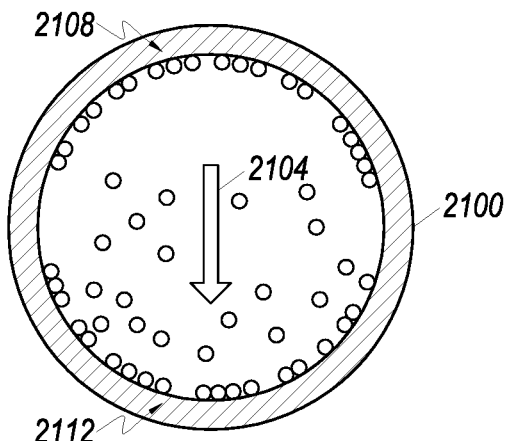
Figure 21D:
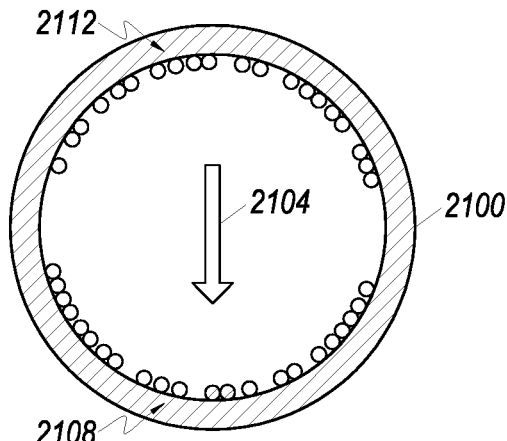
Figure 21E:
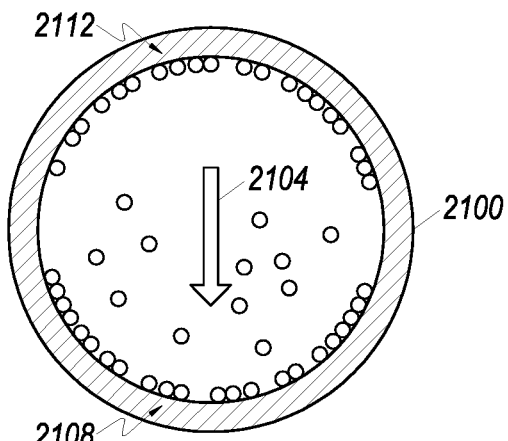

In some embodiments, flow 1400 will pass from step 1424 to step 1436 where the bioreactor 300 is maintained in the second horizontal orientation (FIG. 17) for a second predetermined period of time so that the cells are allowed to settle to a second portion of the bioreactor, such as portion 2012 of hollow fiber 2000 (FIG. 20C) or portion 2112 of hollow fiber 2100 (FIG. 21C).

In some embodiments, flow 1400 may include optional steps 1428 and 1432 prior to proceeding to step 1436. Similar to step 1408, step 1428 provides for circulating fluid through the bioreactor 300. In embodiments, step 1428 may involve activating one or more pumps to circulate fluid through the bioreactor 300. As noted above, an IC circulation pump (e.g., 512,612) may be activated to circulate fluid through the IC side of bioreactor 300 at a second circulation flow rate. In at least one embodiment, fluid carrying the cells may pass through hollow fibers of the bioreactor 300. In other embodiments, cells may be loaded into the EC side of the bioreactor 300 and have the fluid carrying the cells. In these embodiments, an EC circulation pump (e.g., 528, 628) may be activated to circulate fluid through the EC side of bioreactor 300 at a second circulation flow rate.

In embodiments, the second circulation flow rate may be less than the first circulation rate. In embodiments, the second circulation flow rate may be less than about 400 ml/min, less than about 300 ml/min, or even less than about 200 ml/min. In other embodiments, the second circulation rate may be greater than about 25 ml/min, greater than about 500 ml/min, or even greater than about 75 ml/min. In one embodiment, the second circulation flow rate is between about 50 ml/min and about 150 ml/min, such as about 100 ml/min.

In some embodiments, step 1428 may also involve circulation in a different direction than the circulation performed in step 1408. In other words, in some embodiments, step 708 may involve circulating fluid in a counter clockwise direction (see IC loop in FIGS. 5 and 6). In some embodiments, the circulation at step 1428 may be clockwise. In other words, the circulation may flow opposite to the circulation at step 1408. In other embodiments, the circulation in step 1408 may flow in the same direction as step 1408, clockwise or counter clockwise.

Optional step 1428 may in some embodiments involve also rotating the bioreactor 300 in a particular sequence to facilitate distribution of the cells through the bioreactor 300 and circulation paths of the CES to which the bioreactor 300 may be fluidly associated. In other embodiments, the circulating step 1428 may involve rotating the bioreactor 300 for some periods of time, but maintaining the bioreactor 300 stationary for other periods of time.

After optional step 1428, the fluid circulation rate is once again reduced at step 1432. The circulation rate may be reduced to about zero (0) ml/min, or in other embodiments may be reduced to a rate that is above zero (0) ml/min but still allows cells to settle and attach to the bioreactor 300, e.g., an inside surface of hollow fibers of bioreactor 300. In embodiments, step 1432 may involve stopping or turning off one or more pumps used in step 1428 to circulate the fluid.

Referring once again to step 1436, maintaining the bioreactor in the second horizontal orientation allows cells to settle on portion 2012 (or 2112 in FIG. 21C), which may be opposite portion 2008, e.g., portion 2008 (or 2108) may be referred to as a "bottom portion" and portion 2012 (or 2112 in FIG. 21C) may be referred to as a "top portion." FIGS. 20C and 20C illustrate cells settling onto portions 2012 and 2112, or in some embodiments vice versa. In embodiments, the cells will be allowed to settle for a second predetermined period of time that may be selected to not only allow the cells to settle, but also to attach to portion 2012 of the hollow fiber 2000 (or 2112 of fiber 2100).

In some embodiments, the second predetermined period of time may be long enough in duration allow the cells to settle and attach to portion 2012 (or 2112 in FIG. 21C). In these embodiments, the cells may only need to travel the distance of the inner diameter of hollow fiber 2000 or 2100. For example, in embodiments where the hollow fiber has an inner diameter of between about 150 microns and about 300 microns, the second predetermined period of time may be less than about 20 minutes, less than about 15 minutes, or even less than about 10 minutes. In other embodiments, the second predetermined period of time may be greater than about 1 minute, greater than about 2 minutes, greater than about 3 minutes, or even greater than about 4 minutes. In one embodiment, the second period of time may be between about 3 minutes and about 8 minutes, such as about 5 minutes.

In some embodiments, after step 1436, flow 1400 may pass to step 1472 where cells are expanded. Step 1472 may involve a number of substeps, such as circulating fluid into the bioreactor to feed and provide nutrients to the cells attached in the bioreactor. As can be appreciated, step 1472 may also involve providing oxygen to the cells so that they may multiply. Several other parameters in the bioreactor may be controlled in order to optimize the expansion, i.e. growth of the cells. In some embodiments, step 1472 may include circulating fluid to feed the cells for about 24 hours, about 36 hours, about 48 hours, about 60 hours, or even about 72 hours. In some embodiments, the feeding of the cells as part of step 1472 may be performed for less than about 120 hours, less than about 108 hours, less than about 96 hours, less than about 84 hours, or even less than about 72 hours. FIG. 20D illustrates hollow fiber 2000 for this embodiment. Flow then ends at 1476.

Figure 18:
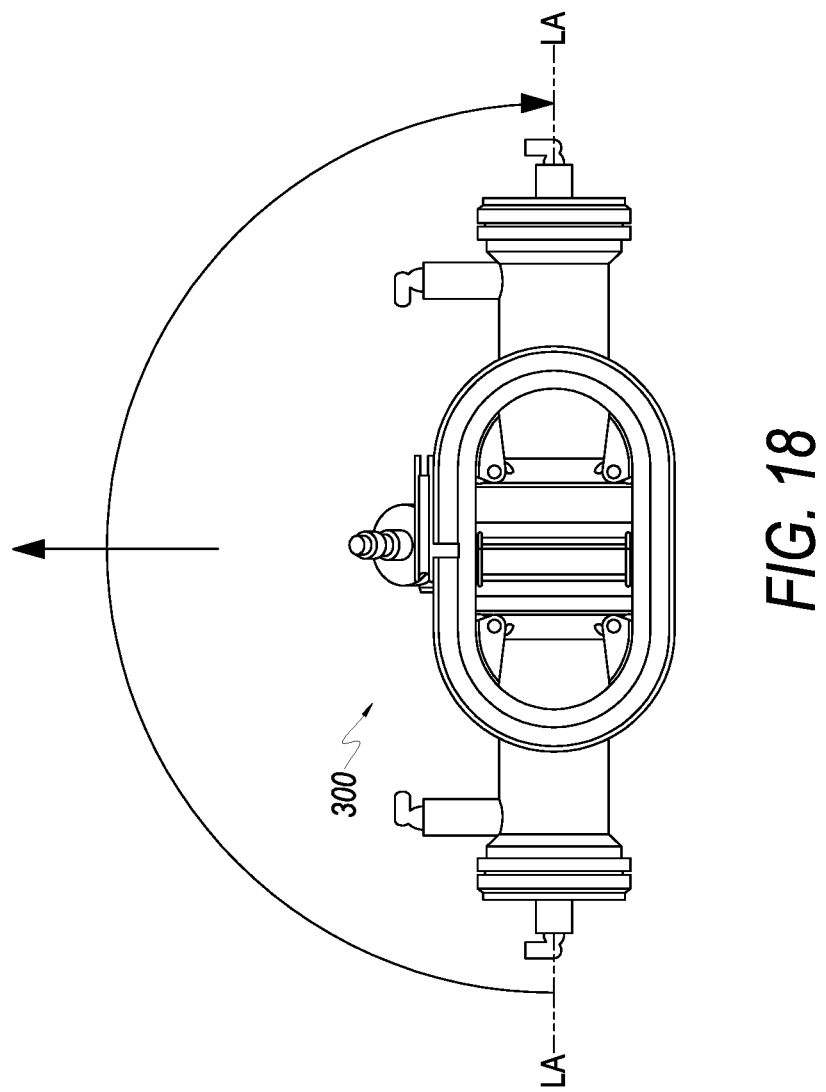
FIG. 18 is a front elevation view of the bioreactor of FIG. 15, wherein the bioreactor is shown rotated back to the original orientation shown in FIG. 15.
Figure 19:
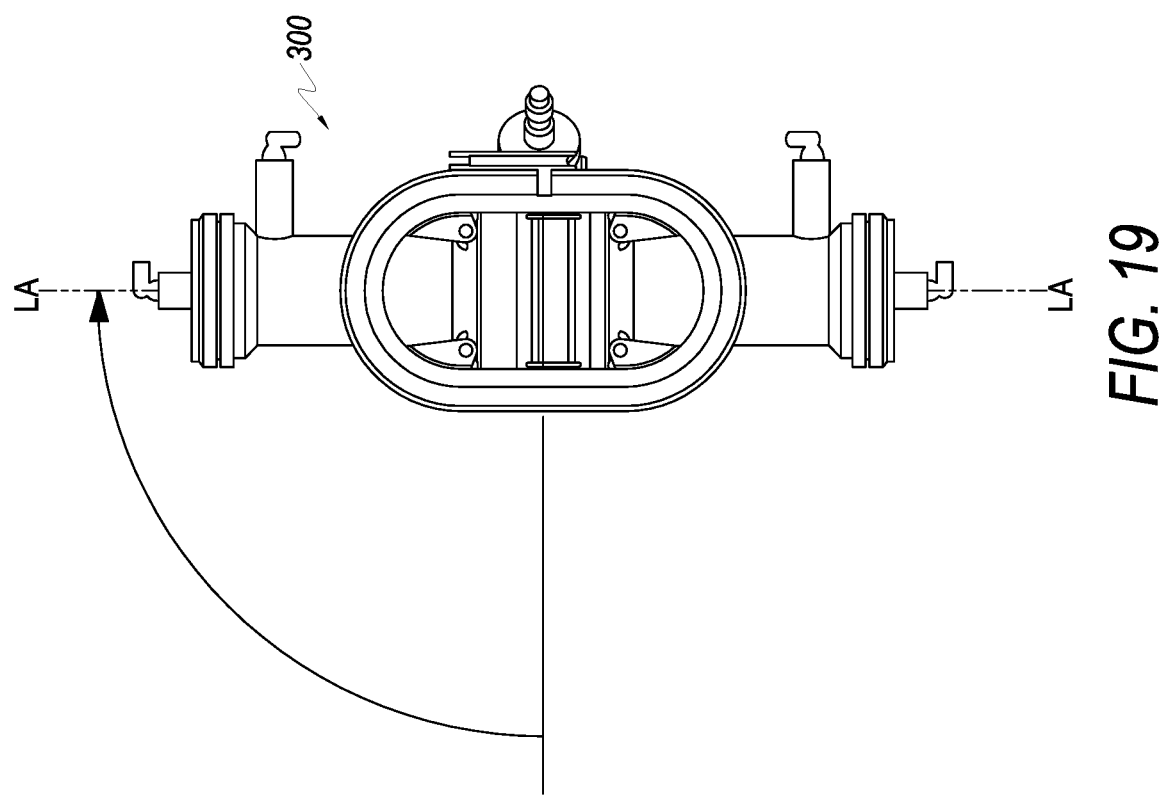
FIG. 19 illustrates a front elevation view of the bioreactor of FIG. 15, wherein the bioreactor is shown rotated about 90 degrees from the view of FIG. 15 and about 180 degrees from the view of FIG. 16.

In other embodiments, flow 1400 may pass to step 1440, where the bioreactor 300 is rotated back to its original first horizontal orientation. FIG. 18 illustrates bioreactor 300 once it has been rotated back to its first horizontal orientation. Step 1440 may be performed by one or more motors connected to bioreactor 300. These motors may be part of a rocking device. In embodiments, flow may pass from step 1440 to step 1472 where the cells are expanded. Flow then ends at 1476.

In other embodiments, flow 1400 passes from step 1440 to step 1444, or in other embodiments, flow may pass directly from step 1436, to step 1444 (when no additional rotation is performed), where fluid is again circulated but at a third circulation flow rate. Similar to steps 1408 and 1428, fluid is circulated through the bioreactor 300. In embodiments, step 1444 may involve activating one or more pumps to circulate fluid through the bioreactor 300. As noted above, an IC circulation pump (e.g., 512 or 612) may be activated to circulate fluid through the IC side of bioreactor 300 at a third circulation flow rate. In at least one embodiment, fluid carrying the cells may pass through (the lumen of) hollow fibers of the bioreactor 300. In other embodiments, cells may be loaded into the EC side of the bioreactor 300 and have the fluid carrying the cells. In these embodiments, an EC circulation pump (e.g., 528, 628) may be activated to circulate fluid through the EC side of bioreactor 300 at the third circulation flow rate.

In embodiments, the third circulation flow rate may be less than the second circulation rate. In embodiments, the third circulation flow rate may be less than about 200 ml/min, less than about 150 ml/min, or even less than about 100 ml/min. In other embodiments, the third circulation rate may be greater than about 10 ml/min, greater than about 20 ml/min, or even greater than about 30 ml/min. In one embodiment, the third circulation flow rate is between about 20 ml/min and about 100 ml/min, such as about 50 ml/min.

In some embodiments, step 1444 may also involve circulation in a different direction than the circulation performed in step 1428. In other words, in some embodiments, step 1428 may involve circulating fluid in a clockwise direction. In some embodiments, the circulation at step 1444 may be similar to step 1408 and be in a counter clockwise direction (see IC loop in FIGS. 5 and 6). In other words, the circulation at step 1444 may flow opposite to the circulation at step 1428, and the same as the direction of circulation of step 1408. In other embodiments, the circulation in steps 1408, 1428, 1444 may flow in the same direction, clockwise or counter clockwise.

Optional step 1444 may in some embodiments involve also rotating the bioreactor 300 in a particular sequence to facilitate distribution of the cells through the bioreactor 300 and circulation paths of the CES to which the bioreactor 300 may be fluidly associated. In other embodiments, the circulating step 1444 may involve rotating the bioreactor 300 for some periods of time, but maintaining the bioreactor 300 stationary for other periods of time.

Flow passes from 1444 to step 1448, where, the fluid circulation rate is once again reduced. The circulation rate may be reduced to about zero (0) ml/min, or in other embodiments may be reduced to a rate that is above zero (0) ml/min but still allows cells to settle and attach to the bioreactor 300, e.g., an inside surface of hollow fibers of bioreactor 300. In embodiments, step 1448 may involve stopping or turning off one or more pumps used in step 1444 to circulate the fluid.

From step 1448, flow passes to step 1452 where the bioreactor is maintained in a horizontal orientation. In those embodiments that include step 1444 (rotate to first orientation), step 1452 will involve maintaining the first horizontal orientation. In those embodiments that do not include the rotation of step 1440, step 1452 will involve maintaining the second horizontal orientation. In any case, step 1452 is performed to allow cells to settle again, such as on portion 2108 (See FIGS. 21D and 21E; if the rotation step 1440 is performed). In embodiments, the cells will be allowed to settle for a third predetermined period of time that may be selected to not only allow the cells to settle, but also to attach.

In some embodiments, the third predetermined period of time may be long enough in duration to allow the cells to settle and attach to portion 2108. In these embodiments, the cells may only need to travel the distance of the inner diameter of hollow fiber 2100. For example, in embodiments where the hollow fiber 2100 has an inner diameter of between about 150 microns and about 300 microns, the third predetermined period of time may be less than about 20 minutes, less than about 15 minutes, or even less than about 10 minutes. In other embodiments, the third predetermined period of time may be greater than about 1 minute, greater than about 2 minutes, greater than about 3 minutes, or even greater than about 4 minutes. In one embodiment, the third period of time may be between about 3 minutes and about 8 minutes, such as about 5 minutes.

Figure 21F:
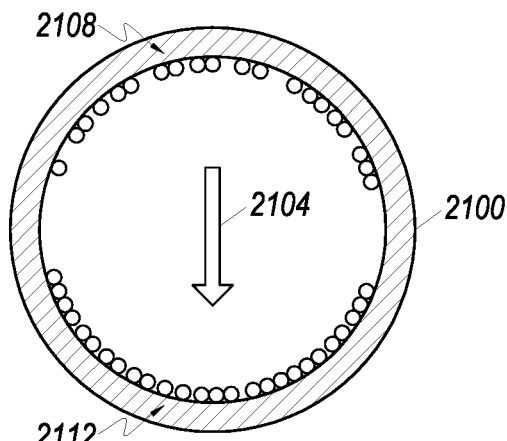

In some embodiments, flow 1400 may pass from step 1452 to step 1472 where the cells are expanded. FIG. 21F illustrates fiber 2100 in these embodiments. Flow would then end at 1476.

In other embodiments, as described below, flow 1400 may include additional rotation (1456), circulation (1460), reduce circulation (1464), and maintain orientation (1468) steps before moving to step 1472 where cells are expanded. In these embodiments, flow 1400 may pass from step 1452 to step 1456, where the bioreactor 300 is rotated back to the second horizontal orientation, if it was rotated at step 1440 to the first horizontal orientation. FIG. 17 illustrates bioreactor 300 in the second horizontal orientation. Step 1456 may be performed by one or more motors connected to bioreactor 300. These motors may be part of a rocking device. In some embodiments, this step may be unnecessary, if step 1440 was not performed to rotate the bioreactor to the first horizontal orientation.

Flow 1400 passes to step 1460 where fluid is again circulated but at a fourth circulation flow rate. Similar to steps 1408, 1428, and 1444, fluid is circulated through the bioreactor 300. In embodiments, step 1444 may involve activating one or more pumps to circulate fluid through the bioreactor 300, as noted above, an IC circulation pump (e.g., 512, 612) may be activated to circulate fluid through the IC side of bioreactor 300 at a fourth circulation flow rate. In at least one embodiment, fluid carrying the cells may pass through hollow fibers of the bioreactor 300. In other embodiments, cells may be loaded into the EC side of the bioreactor 300 and have the fluid carrying the cells. In these embodiments, an EC circulation pump (e.g., 528, 628) may be activated to circulate fluid through the EC side of bioreactor 300 at the fourth circulation flow rate.

In embodiments, the fourth circulation flow rate may be less than the third circulation rate. In embodiments, the fourth circulation flow rate may be less than about 100 ml/min, less than about 75 ml/min, or even less than about 50 ml/min. In other embodiments, the fourth circulation rate may be greater than about 5 ml/min, greater than about 10 ml/min, or even greater than about 15 ml/min. In one embodiment, the fourth circulation flow rate is between about 15 ml/min and about 35 ml/min, such as about 25 ml/min.

In some embodiments, step 1460 may also involve circulation in a different direction than the circulation performed in step 1444. In other words, in some embodiments, step 1444 may involve circulating fluid in a counter clockwise direction. In some embodiments, the circulation at step 1460 may be similar to step 1428 and be in a clockwise direction. In other words, the circulation at step 1460 may flow opposite to the circulation at step 1444, and the same as the direction of circulation of step 1428. In other embodiments, the circulation in steps 1408, 1428, 1444 and 1460 may flow in the same direction, clockwise or counter clockwise.

Step 1460 may in some embodiments involve also rotating the bioreactor 300 in a particular sequence to facilitate distribution of the cells through the bioreactor 300 and circulation paths of the CES to which the bioreactor 300 may be fluidly associated. In other embodiments, the circulating step 1460 may involve rotating the bioreactor 300 for some periods of time, but maintaining the bioreactor 300 stationary for other periods of time.

Flow passes from 1460 to step 1464, where, the fluid circulation rate is once again reduced. The circulation rate may be reduced to about zero (0) ml/min, or in other embodiments may be reduced to a rate that is above zero (0) ml/min but still allows cells to settle and attach to the bioreactor 300, e.g., an inside surface of hollow fibers of bioreactor 300. In embodiments, step 1464 may involve stopping or turning off one or more pumps used in step 1460 to circulate the fluid.

From step 1464, flow passes to step 1468 where the bioreactor is maintained in the second horizontal orientation to allow cells to settle on for example portion 2112 again (see FIG. 21F). In embodiments, the cells will be allowed to settle for a fourth predetermined period of time that may be selected to not only allow the cells to settle, but also to attach once again.

In some embodiments, the fourth predetermined period of time may be long enough in duration to allow the cells to settle and attach. In these embodiments, the cells may only need to travel the distance of the inner diameter of the hollow fiber, e.g., fiber 2100. For example, in embodiments where the hollow fiber 2100 has an inner diameter of between about 150 microns and about 300 microns, the fourth predetermined period of time may be less than about 20 minutes, less than about 15 minutes, or even less than about 10 minutes. In other embodiments, the fourth predetermined period of time may be greater than about 1 minute, greater than about 2 minutes, greater than about 3 minutes, or even greater than about 4 minutes. In one embodiment, the fourth period of time may be between about 3 minutes and about 8 minutes, such as about 5 minutes.

After step 1468, flow 1400 passes to step 1472 where the cells settled and attached to the bioreactor 300, e.g., to hollow fibers of the bioreactor, are expanded, i.e., multiplied. Flow 1400 then ends at 1476.

Without being bound by theory, it is believe that in embodiments, the cell expansion is improved if the steps of flow 1400 are performed. It is believed that these embodiments help to ensure that more portions of the bioreactor, e.g., surface of hollow fibers in the bioreactor, are seeded with cells prior to cell expansion. This may provide for more cells to initially be seeded, and ultimately may improve cell yield and reduce cell doubling time, as compared to conventional processes.

Although flow 1400 includes specific number of steps that provide for rotating, circulating, reducing circulation, and maintaining the orientation of the bioreactor, other embodiments are not limited to these specific number of steps. In other embodiments, even after step 1468, the bioreactor may be rotated again, circulation can be restarted again, followed by another period of reducing circulation to allow cells to settle and maintain the orientation for a period of time to allow cells to attach to portion of a bioreactor. These steps may be performed any number of times. In embodiments, each time the circulation is restarted, it is at a lower rate than the previous circulation. In other embodiments, the circulation rates may be the same each time circulation is started. In yet other embodiments, the direction of circulation may be changed, with circulation in a first direction, followed by stopping the circulation to allow the cells to settle and attach, circulation in a direction opposite the first direction (clockwise vs. counter clockwise) and again stopping the circulation to allow the cells to settle.

Referring back to FIG. 11, zones 1112, 1116, 1120 and 1124 represent fibers that may have fluid circulating through them at different flow rates. In other words, without being bound by theory, it is believed that circulation at relatively high flow rates, such as rates that may be used in circulation steps 1408 or 1428 (FIG. 14) may primarily flow through fibers in zone 1112. It is believed that the higher flow rates do not allow fluid to disperse enough to flow evenly into the hollow fibers in the outer zones. As the flow rate is reduced, such as in steps 1444 and 1460, it is believed that the fluid may disperse into hollow fibers in outer zones, such as 1116, 1120 and 1124.

It is believed that having steps 1408, 1428, 1444 and 1452 circulate at different flow rates, allows the fluid to flow through more of the hollow fibers 1108 than if just a single flow rate would be used. In one embodiment of a process that follows flow chart 1400, at step 1408 (at the flow rates described above), fluid may flow through the hollow fibers in zone 1112. At step 1428 (at the flow rates described above), fluid may flow through the hollow fibers in both zones 1112 and 1116 because the rate is slower and the fluid may disperse more. At step 1444 (at the flow rates described above), fluid may flow through the hollow fibers in zones 1112, 1116, and 1120 because the flow rate is yet slower and fluid may disperse even more. At step 1452 (at the flow rates described above), fluid may flow through the hollow fibers in all the zones 1112, 1116, 1120 and 1124 because the flow rates are even slower and the fluid may disperse through all of the fibers in the various zones. Thus, it is believe that fluid with the cells may flow into more of the hollow fibers using a sequence of different flow rates, than if a single high flow rate circulation is used.

Furthermore, it is also believed that the different flow rates may also affect the longitudinal distribution of cells along the bioreactor, e.g., along a hollow fiber. That is, a higher flow rate may allow cells to flow further along inside a hollow fiber. For example, at a higher flow rate, a cell being carried by fluid may reach beyond half the length of the hollow fiber. At a lower flow rate, a cell being carried by fluid may reach half the length of the hollow fiber. At even a lower flow rate, a cell being carried by fluid may reach less than half the length of the hollow fiber. Accordingly, in some embodiments, it is believed that the use of different flow rates may provide some improvement in longitudinal distribution of cells along the length of the bioreactor, e.g., a hollow fiber.

Figure 22:
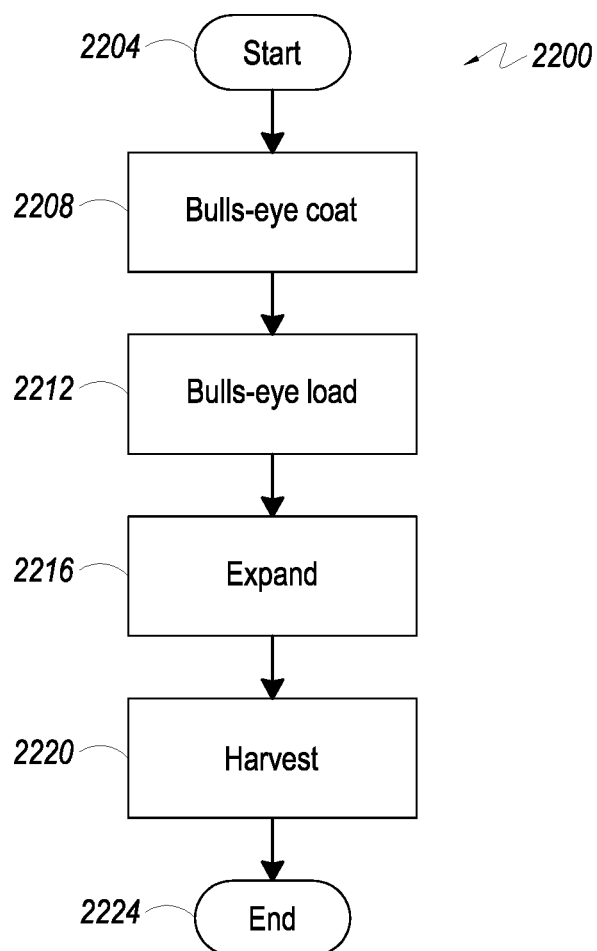
FIG. 22 is a flow chart of a process for coating, loading, distributing, attaching, and expanding cells according to some embodiments.

Referring now to FIG. 22, flow 2200 illustrates a process of expanding cells according to some embodiments of the present disclosure. Flow 2200 starts at 2204 and passes to step 2208 where a bulls-eye coat process is performed on a CES (e.g., CES 500 and/or CES 600) to coat portions of a bioreactor (bioreactors 501, 601). In embodiments, step 2208 may involve performing steps of one or more of the processes described above with respect to flows 1000, 1200, and/or 1300, which may be referred to as bulls-eye coating processes. As described in detail above, flows 1000, 1200, and/or 1300 provide for changing flow rates, changing direction of flows, and/or rotating of a bioreactor to improve the distribution of a coating reagent in a bioreactor. As described above, changing flow rates, changing direction of flows, and/or rotating of a bioreactor may allow interior surfaces of hollow fibers (in a hollow fiber bioreactor) to be more completely coated during a coating process.

From step 2208, flow 2200 passes to steps 2212 where a bulls-eye cell load process is performed on the CES (e.g., CES 500 and/or CES 600) to load cells into the bioreactor (bioreactors 501, 601). In embodiments, step 2212 may involve performing steps of one or more of the processes described above with respect to flow 1400, which may be referred to as a bulls-eye cell loading process. As described in detail above, flow 1400 provides for changing flow rates, changing direction of flows, and/or rotating of a bioreactor to improve the distribution of cells loaded/attached in a bioreactor. As described above, changing flow rates, changing direction of flows, and/or rotating of a bioreactor may allow cells to be more uniformly distributed on interior surfaces of hollow fibers (in a hollow fiber bioreactor).

After step 2212, flow passes to step 2216 where cell are expanded. In embodiments, the expanding of cells may involve a number of steps. For example, step 2216 may involve performing one or more of the steps described above with respect to step 718 in flow 700 (FIG. 7), e.g., feeding of cells.

At step 2220 cells expanded at step 2216 are harvested. In embodiments, the harvesting of cells may involve a number of steps. For example, step 2220 may involve performing one or more of the steps described above with respect to step 722 in flow 700 (FIG. 7). Flow 2220 ends at 2224.

With respect to the processes illustrated in FIGS. 7-10, 12-14, and 22, the operational steps depicted are offered for purposes of illustration and may be rearranged, combined into other steps, used in parallel with other steps, etc., according to embodiments of the present disclosure. Fewer or additional steps may be used in embodiments without departing from the spirit and scope of the present disclosure. Also, steps (and any sub-steps), such as priming, coating a bioreactor, loading cells, for example, may be performed automatically in some embodiments, such as by a processor executing custom and/or pre-programmed tasks stored in memory.

Examples and further description of tasks and protocols, including custom tasks and pre-programmed tasks, for use with a cell expansion system are provided in U.S. patent application Ser. No. 13/269,323 ("Configurable Methods and Systems of Growing and Harvesting Cells in a Hollow Fiber Bioreactor System," filed Oct. 7, 2011) and U.S. patent application Ser. No. 13/269,351 ("Customizable Methods and Systems of Growing and Harvesting Cells in a Hollow Fiber Bioreactor System," filed Oct. 7, 2011), which applications are hereby incorporated by reference herein in their entireties for all that they teach and for all purposes.

Figure 23:
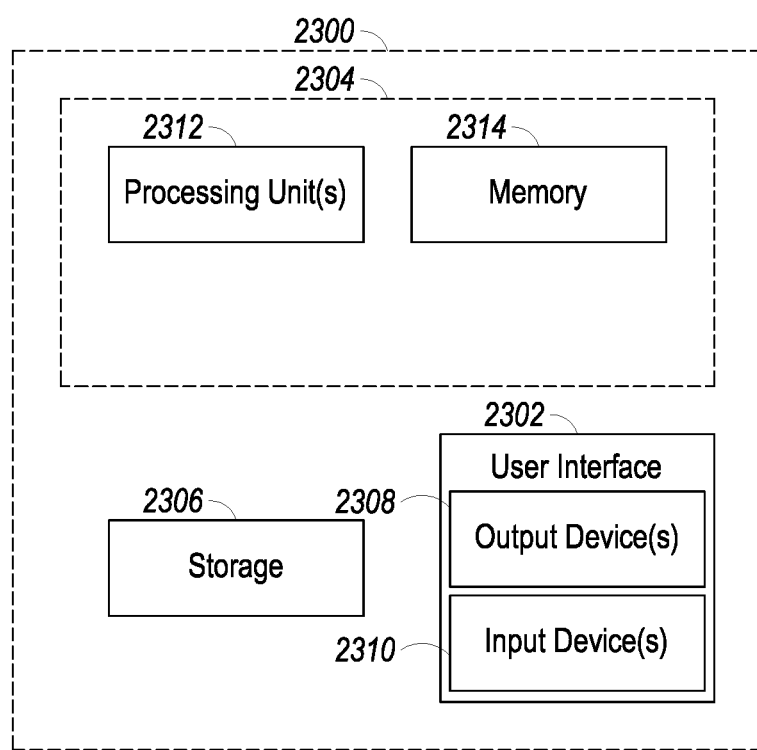
FIG. 23 illustrates an example processing system of a cell expansion system upon which embodiments of the present disclosure may be implemented.
Figure 24:
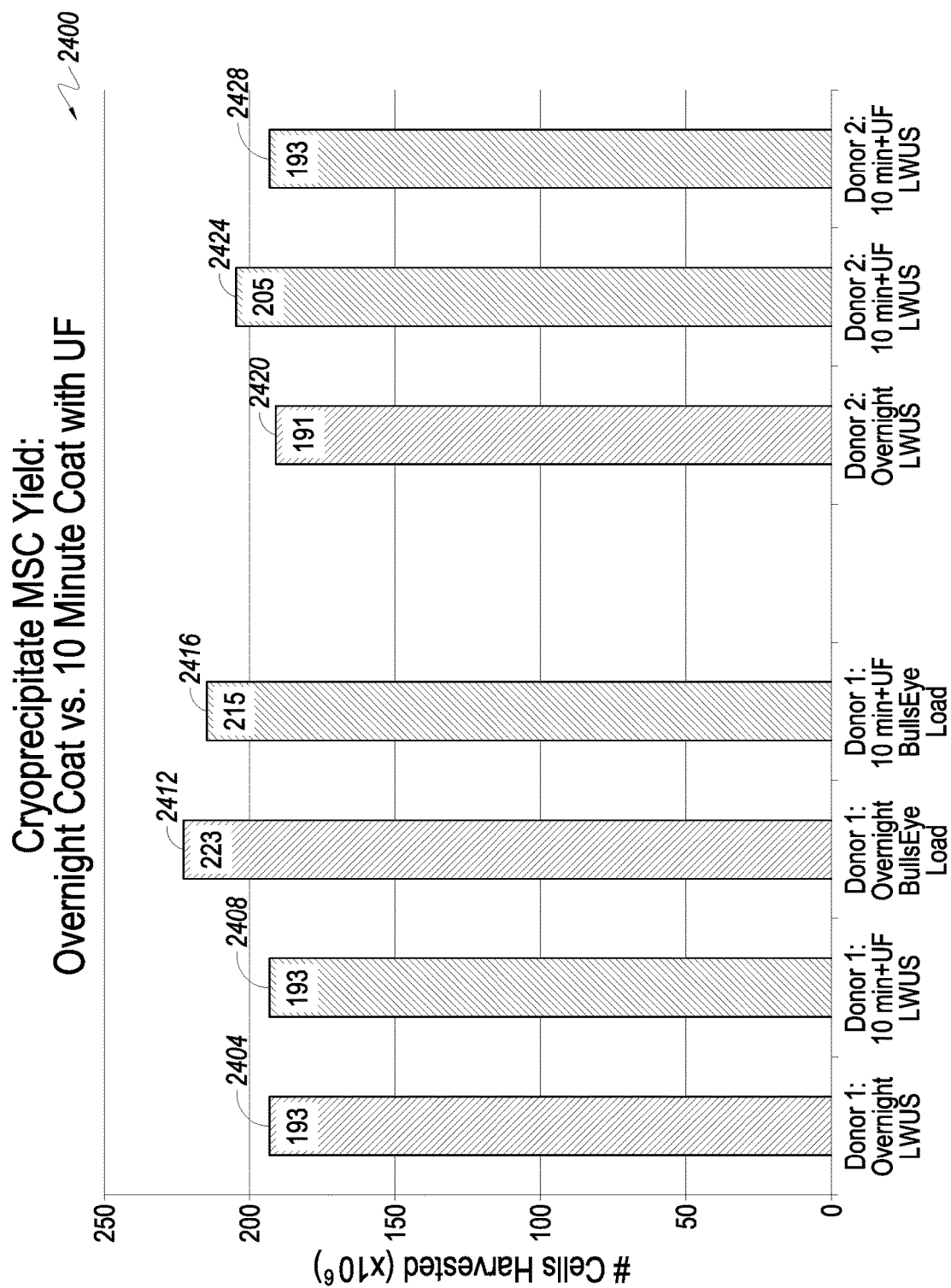
FIG. 24 depicts example cell yields using a coating application(s) in accordance with embodiments of the present disclosure.
Figure 25A:
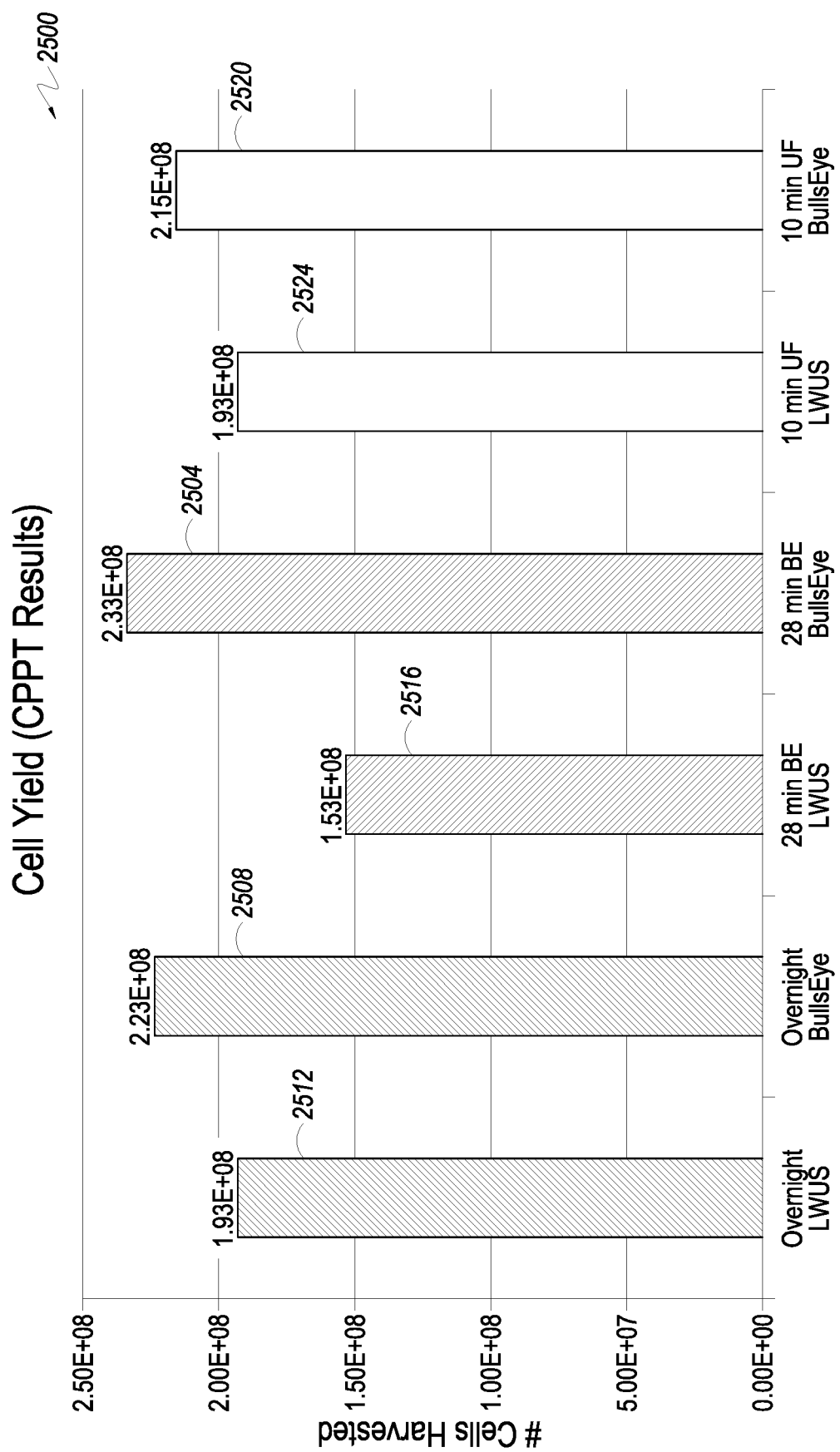
FIG. 25A illustrates example results of expanding cells using various coating and cell loading procedures in accordance with embodiments of the present disclosure.
Figure 25B:
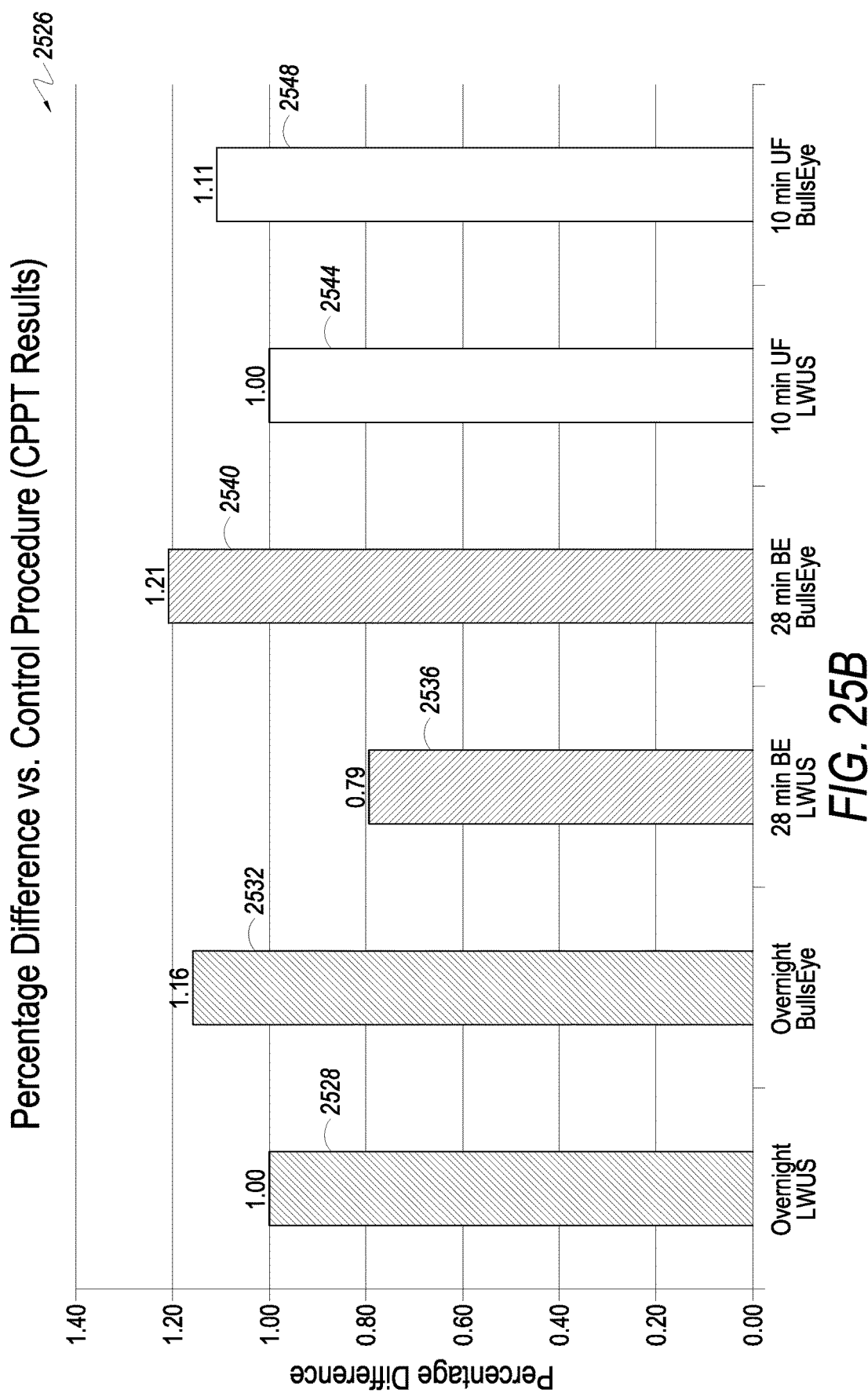
FIG. 25B depicts example results of expanding cells using various coating and cell loading procedures in accordance with embodiments of the present disclosure.
Figure 26A:
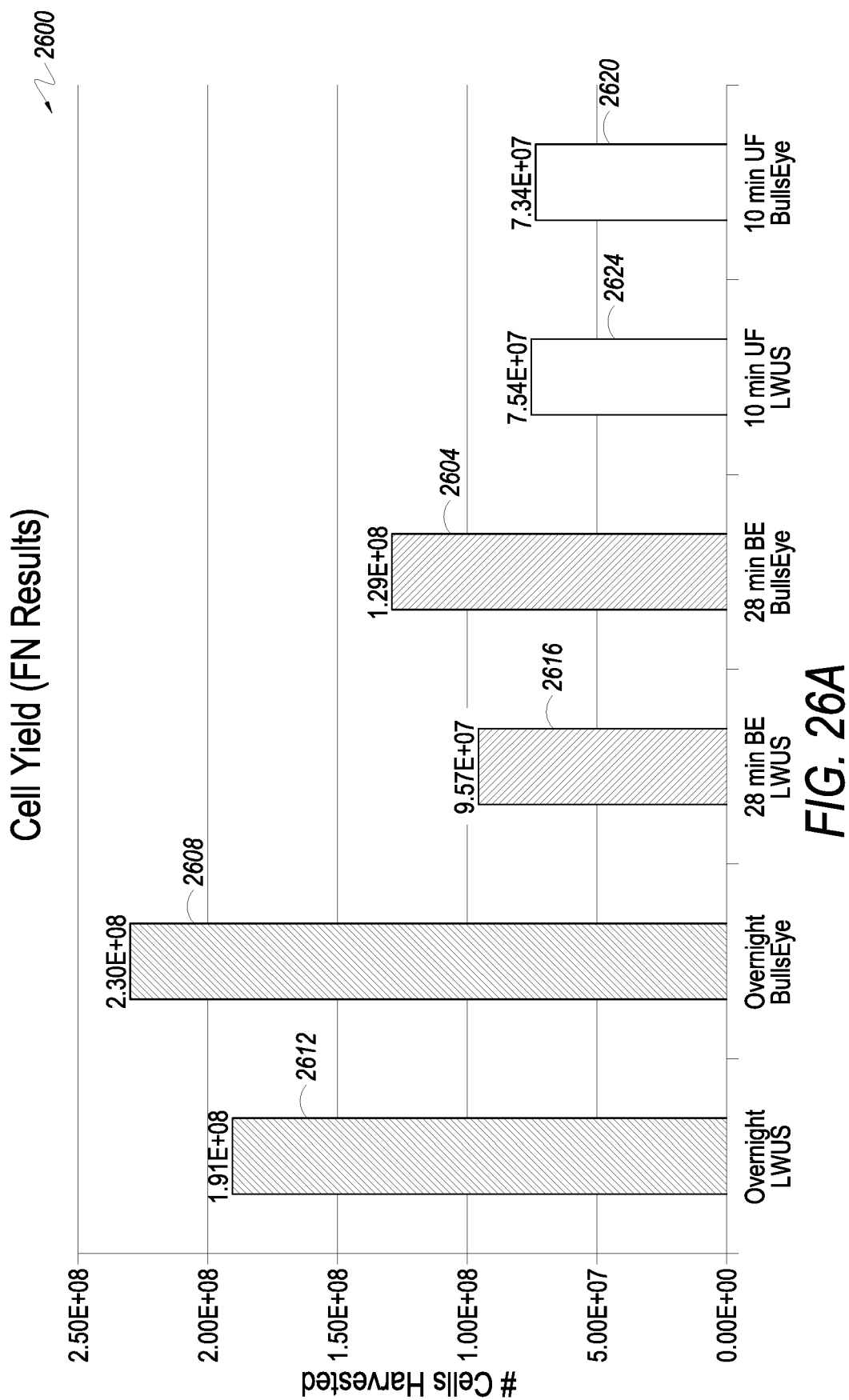
FIG. 26A illustrates example results of expanding cells using various coating and cell loading procedures in accordance with embodiments of the present disclosure.
Figure 26B:
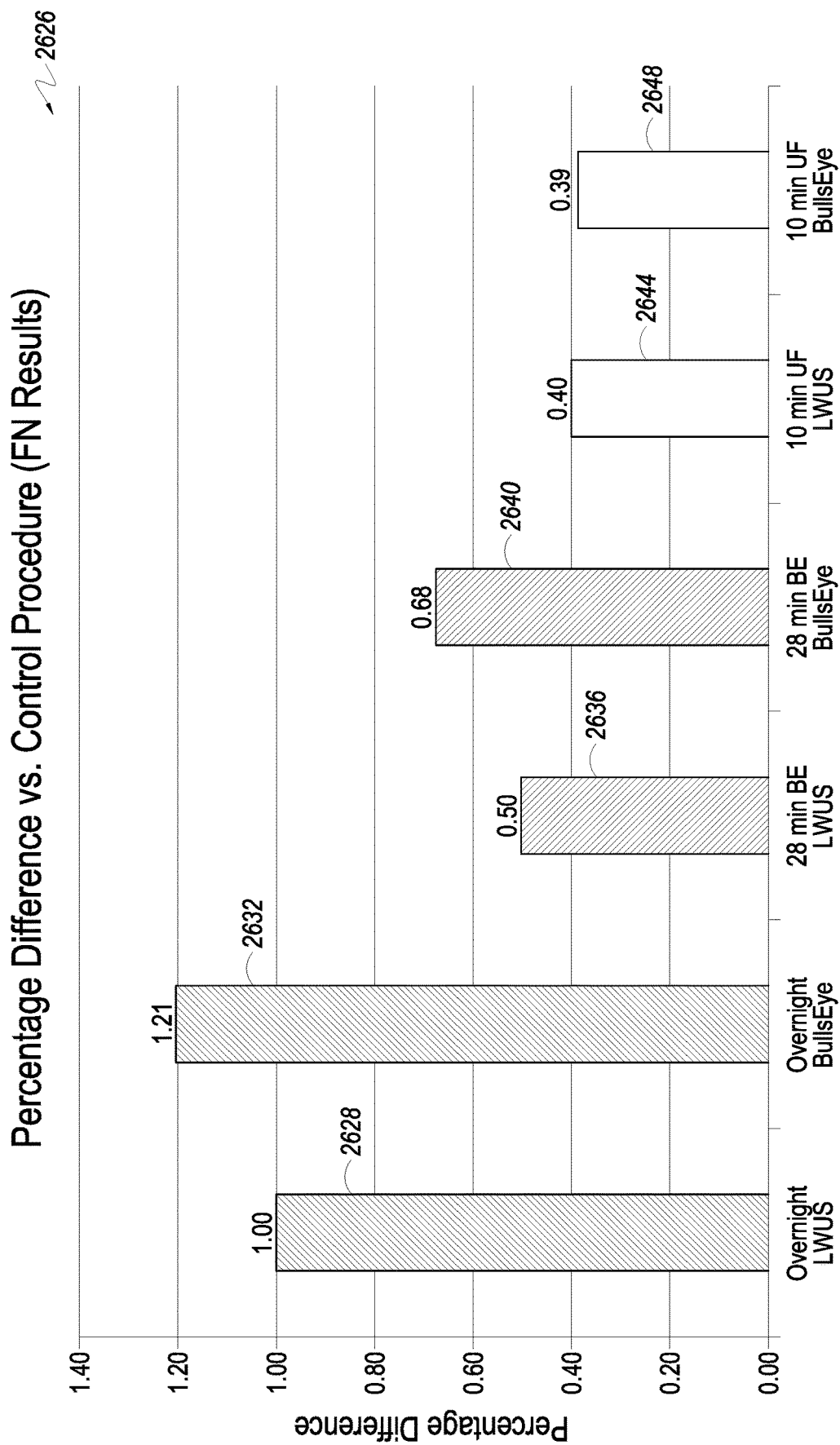
FIG. 26B depicts example results of expanding cells using various coating and cell loading procedures in accordance with embodiments of the present disclosure.
Figure 27A:
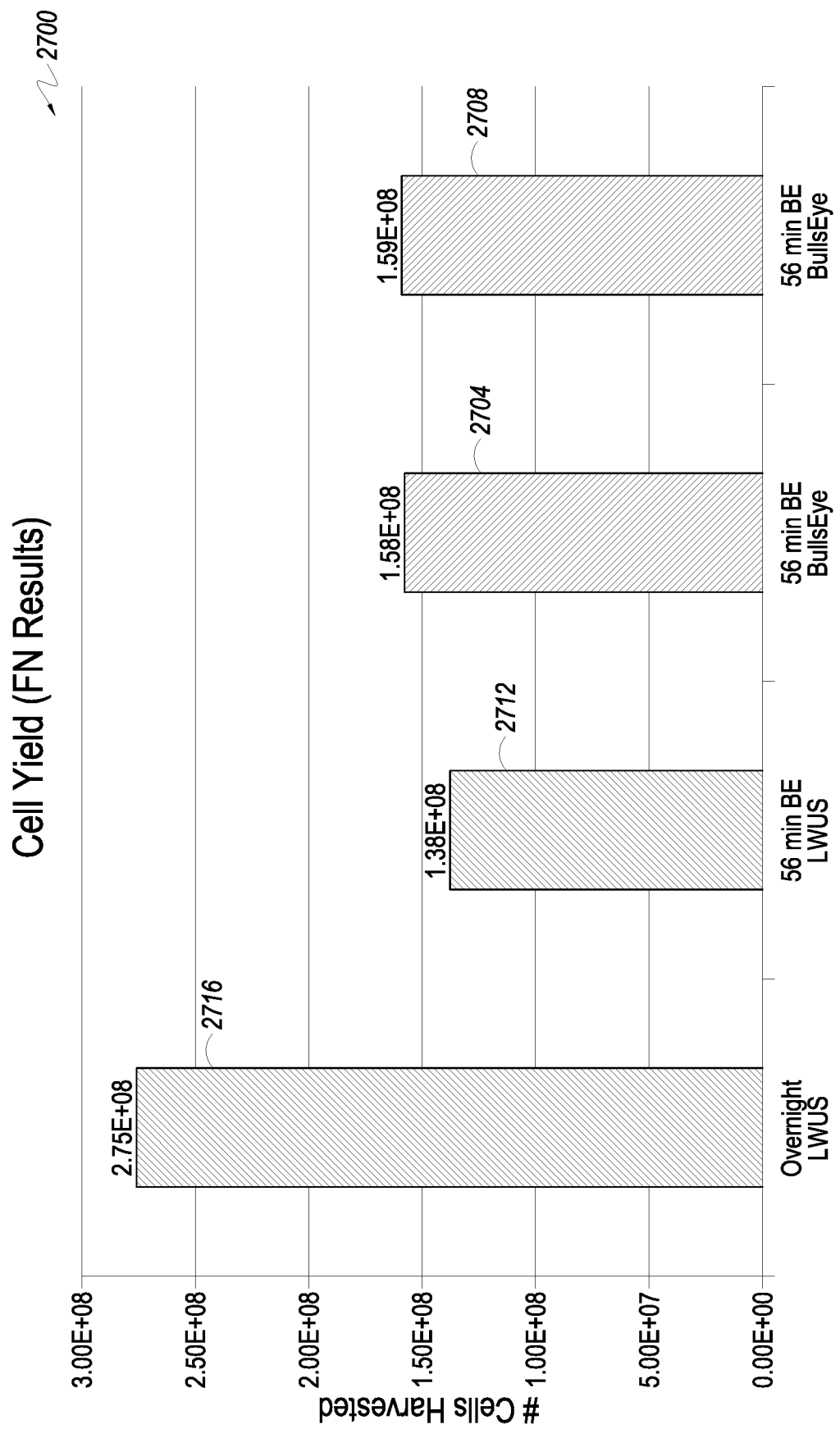
FIG. 27A illustrates example results of expanding cells using various coating and cell loading procedures in accordance with embodiments.

Next, FIG. 23 illustrates example components of a computing system 2300 upon which embodiments of the present disclosure may be implemented. Computing system 2300 may be used in embodiments, for example, where a cell expansion system uses a processor to execute tasks, such as custom tasks or pre-programmed tasks performed as part of a process, such as process 700, 800, 900, 916, 1000, 1200, 1300, 1400 and/or 2200 described above. In embodiments, pre-programmed tasks may include, "IC/EC Washout" task and/or "Feed Cells" task, for example.

The computing system 2300 may include a user interface 2302, a processing system 2304, and/or storage 2306. The user interface 2302 may include output device(s) 2308, and/or input device(s) 2310 as understood by a person of skill in the art. Output device(s) 2308 may include one or more touch screens, in which the touch screen may comprise a display area for providing one or more application windows. The touch screen may also be an input device 2310 that may receive and/or capture physical touch events from a user or operator, for example. The touch screen may comprise a liquid crystal display (LCD) having a capacitance structure that allows the processing system 2304 to deduce the location(s) of touch event(s), as understood by those of skill in the art. The processing system 2304 may then map the location of touch events to UI elements rendered in predetermined locations of an application window. The touch screen may also receive touch events through one or more other electronic structures, according to embodiments. Other output devices 2308 may include a printer, speaker, etc. Other input devices 2310 may include a keyboard, other touch input devices, mouse, voice input device, etc., as understood by a person of skill in the art.

Processing system 2304 may include a processing unit 2312 and/or a memory 2314, according to embodiments of the present disclosure. The processing unit 2312 may be a general purpose processor operable to execute instructions stored in memory 2314. Processing unit 2312 may include a single processor or multiple processors, according to embodiments. Further, in embodiments, each processor may be a multi-core processor having one or more cores to read and execute separate instructions. The processors may include general purpose processors, application specific integrated circuits (ASICs), field programmable gate arrays (FPGAs), other integrated circuits, etc., as understood by a person of skill in the art.

The memory 2314 may include any short-term or long-term storage for data and/or processor executable instructions, according to embodiments. The memory 2314 may include, for example, Random Access Memory (RAM), Read-Only Memory (ROM), or Electrically Erasable Programmable Read-Only Memory (EEPROM), as understood by a person of skill in the art. Other storage media may include, for example, CD-ROM, tape, digital versatile disks (DVD) or other optical storage, tape, magnetic disk storage, magnetic tape, other magnetic storage devices, etc., as understood by a person of skill in the art.

Storage 2306 may be any long-term data storage device or component. Storage 2306 may include one or more of the systems described in conjunction with the memory 2314, according to embodiments. The storage 2306 may be permanent or removable. In embodiments, storage 2306 stores data generated or provided by the processing system 2304.

EXAMPLES

Results for some examples of protocols/methods/processes that may be used with a cell expansion system, such as CES 500 (FIG. 5) and/or CES 600 (FIG. 6) that implement aspects of the embodiments such as those shown in FIGS. 700, 800, 900, and/or 916, 1000, 1200, 1300, 1400 and/or 2200 are described below. Although specific features may be described in the examples, such examples are provided merely for illustrative and descriptive purposes. For example, while examples may provide for the expansion of MSCs, other cell types may be used in other embodiments. The present embodiments are not limited to the examples provided herein.

It is noted that the example protocols/methods/processes are provided for illustrative purposes and are not intended to limit other embodiments, which may include different or additional steps, parameters, or other features. The example protocols/methods/processes, including the steps (and any sub-steps), may be performed automatically in some embodiments, such as by a processor executing custom tasks or pre-programmed tasks stored in memory. In other embodiments, the steps (and any sub-steps) may be performed through the combination of automated and manual execution of operations. In further embodiments, the steps (and any sub-steps) may be performed by an operator(s) or user(s) or through other manual means.

Some examples provide example data from embodiments providing for the expansion of cells using various coating procedures, various cell loading procedures, various coating materials (e.g., cryoprecipitate (CPPT), fibronectin (FN)), and/or combination(s) of such procedures and/or materials. Such procedures include, for example: positive ultrafiltration coating procedure; positive ultrafiltration coating procedure with a bulls-eye (BE) cell load procedure; positive ultrafiltration coating procedure with a load cells with uniform suspension (LWUS) cell loading procedure; overnight coating with cryoprecipitate; overnight coating with fibronectin; bulls-eye coating procedure; 28-minute bulls-eye coating procedure; etc. Examples and further description of a bulls-eye coating procedure(s) are provided in an application U.S. patent application Ser. No. 15/616,745, entitled, "Coating a Bioreactor," filed on Jun. 7, 2017, which similar to the present application, also claims priority to U.S. Provisional Application Ser. No. 62/347,012, entitled "Coating a Bioreactor," and filed on Jun. 7, 2016. Examples of other coating processes/steps that, in embodiments, may be utilized in combination with the embodiments described herein are described in U.S. patent application Ser. No. 15/616,635, entitled "METHODS AND SYSTEMS FOR COATING A CELL GROWTH SURFACE," filed Jun. 7, 2017, which similar to the present application also claims priority to U.S. Provisional Patent Application No. 62/347,025, entitled "GROWTH SURFACE COATING," filed Jun. 7, 2016. These applications are hereby incorporated by reference in their entireties for all that they teach and for all purposes. As described above, examples and further description of a bulls-eye cell loading procedure(s) are provided in U.S. patent application Ser. No. 14/542,276 (U.S. Pat. No. 9,617,506), entitled, "Expanding Cells in a Bioreactor," issued on Apr. 11, 2017, which is hereby incorporated by reference herein in its entirety for all that it teaches and for all purposes.

Example 1

Below is an example of a protocol that may be used for implementing embodiments of flows 1000, 1200, and/or 1300 on CES systems such as CES 500, 600. Although specific settings are shown and described below, other embodiments may provide for different values.

Day: 0 Bulls-Eye Coat Bioreactor

Purpose: coats the bioreactor membrane with a reagent.

Step 1: loads a reagent into the IC loop until the bag is empty.

Step 2: chases the reagent from the ARC into the IC loop.

Step 3: coats the bioreactor using +UFR.

Before starting this task, the following preconditions may be satisfied:

Coating is preceded by system prime with RT PBS; and

Include 40 mL or more of air in the cell inlet bag.

Table 24 describes the bags of solution attached to each line when performing Coat Bioreactor. These solutions and corresponding volumes are based on some settings for this task.

TABLE 24

Solutions for Coat Bioreactor

| Bag | Solution in Bag | Volume (estimation) |
|---|---|---|
| Cell Inlet | None | N/A |
| Reagent | CPPT or Fibronectin | 6-25 mL CPPT in 100 mL total volume w/PBS or 5 mg Fibronectin in 100 mL total volume w/PBS |
| IC Media | None | N/A |
| Wash | PBS | 1 L |
| EC Media | None | N/A |

Coat Bioreactor pathway: Task>System Management>Coat Bioreactor

1 Enter the values for each setting for step 1 shown in Table 25.

TABLE 25

Step 1 for Coat Bioreactor

| Setting | Factory | Laboratory Modifications |
|---|---|---|
| IC Inlet | Reagent | |
| IC Inlet Rate | 10 mL/min | |
| IC Circulation Rate | 100 mL/min | |
| EC Inlet | None | |
| EC Inlet Rate | 0 mL/min | |
| EC Circulation Rate | 30 mL/min | |
| Outlet | EC Outlet | |
| Rocker Control | Stationary (0°) | |
| Stop Condition | Empty Bag | |

2 Enter the values for each setting for step 2 shown in Table 26.

TABLE 26

Step 2 Settings for Coat Bioreactor

| Setting | Factory | Laboratory Modifications |
|---|---|---|
| IC Inlet | Wash | |
| IC Inlet Rate | 10 mL/min | |
| IC Circulation Rate | 100 mL/min | |
| EC Inlet | None | |
| EC Inlet Rate | 0 mL/min | |
| EC Circulation Rate | 30 mL/min | |
| Outlet | EC Outlet | |
| Rocker Control | Stationary (0°) | |
| Stop Condition | IC Volume (22 mL) | |

3 Enter the values for each setting for step 3 shown in Table 27.

TABLE 27

Step 3 Settings for Coat Bioreactor

| Setting | Factory | Laboratory | Modifications |
|---|---|---|---|
| IC Inlet | None | | |
| IC Inlet Rate | 0 mL/min | | |
| IC Circulation Rate | | ~~20 mL/min~~ | −300 mL/min |
| EC Inlet | Wash | | |
| EC Inlet Rate | 0.1 mL/min | | |
| EC Circulation Rate | 30 mL/min | | |
| Outlet | EC Outlet | | |
| Rocker Control | Stationary (180°) | | |
| Stop Condition | | ~~Manual~~ | 4 min |

4 Enter the values for each setting for step 4 shown in Table 28.

TABLE 28

Step 4 Settings for Coat Bioreactor

| Setting | Factory | Laboratory | Modifications |
|---|---|---|---|
| IC Inlet | None | | |
| IC Inlet Rate | 0 mL/min | | |
| IC Circulation Rate | 0 mL/min | | 250 mL/min |
| EC Inlet | Wash | | |
| EC Inlet Rate | 0.1 mL/min | | |
| EC Circulation Rate | 30 mL/min | | |
| Outlet | EC Outlet | | |
| Rocker Control | Stationary (0°) | | |
| Stop Condition | | ~~Manual~~ | 4 min |

5 Enter the values for each setting for step 5 shown in Table 29.

TABLE 29

Step 5 Settings for Coat Bioreactor

| Setting | Factory | Laboratory | Modifications |
|---|---|---|---|
| IC Inlet | None | | |
| IC Inlet Rate | 0 mL/min | | |
| IC Circulation Rate | | ~~20 mL/min~~ | −200 mL/min |
| EC Inlet | Wash | | |
| EC Inlet Rate | 0.1 mL/min | | |
| EC Circulation Rate | 30 mL/min | | |
| Outlet | EC Outlet | | |
| Rocker Control | Stationary (180°) | | |
| Stop Condition | | ~~Manual~~ | 4 min |

6 Enter the values for each setting for step 6 shown in Table 30.

TABLE 30

Step 6 Settings for Coat Bioreactor

| Setting | Factory | Laboratory | Modifications |
|---|---|---|---|
| IC Inlet | None | | |
| IC Inlet Rate | 0 mL/min | | |
| IC Circulation Rate | | ~~20 mL/min~~ | 150 mL/min |
| EC Inlet | Wash | | |
| EC Inlet Rate | 0.1 mL/min | | |
| EC Circulation Rate | 30 mL/min | | |
| Outlet | EC Outlet | | |
| Rocker Control | Stationary (0°) | | |
| Stop Condition | | ~~Manual~~ | 4 min |

7 Enter the values for each setting for step 7 shown in Table 31.

TABLE 31

Step 7 Settings for Coat Bioreactor

| Setting | Factory | Laboratory | Modifications |
|---|---|---|---|
| IC Inlet | None | | |
| IC Inlet Rate | 0 mL/min | | |
| IC Circulation Rate | | ~~20 mL/min~~ | −100 mL/min |
| EC Inlet | Wash | | |
| EC Inlet Rate | 0.1 mL/min | | |
| EC Circulation Rate | 30 mL/min | | |
| Outlet | EC Outlet | | |
| Rocker Control | Stationary (180°) | | |
| Stop Condition | | ~~Manual~~ | 4 min |

8 Enter the values for each setting for step 8 shown in Table 32.

TABLE 32

Step 8 Settings for Coat Bioreactor

| Setting | Factory | Laboratory | Modifications |
|---|---|---|---|
| IC Inlet | None | | |
| IC Inlet Rate | 0 mL/min | | |
| IC Circulation Rate | | ~~20 mL/min~~ | 50 mL/min |
| EC Inlet | Wash | | |
| EC Inlet Rate | 0.1 mL/min | | |
| EC Circulation Rate | 30 mL/min | | |
| Outlet | EC Outlet | | |
| Rocker Control | Stationary (0°) | | |
| Stop Condition | | ~~Manual~~ | 4 min |

9 Enter the values for each setting for step 9 shown in Table 33.

TABLE 33

Step 9 Settings for Coat Bioreactor

| Setting | Factory | Laboratory | Modifications |
|---|---|---|---|
| IC Inlet | None | | |
| IC Inlet Rate | 0 mL/min | | |
| IC Circulation Rate | | ~~20 mL/min~~ | −25 mL/min |
| EC Inlet | Wash | | |
| EC Inlet Rate | 0.1 mL/min | | |
| EC Circulation Rate | 30 mL/min | | |
| Outlet | EC Outlet | | |
| Rocker Control | Stationary (180°) | | |
| Stop Condition | | ~~Manual~~ | 4 min |

Example 2

Example results of expanding cells using a coating procedure(s) with, for example, the above methods 800, 1000, and/or 1100 and/or with systems 500, 600, are shown in graph 1600 of FIG. 16, in accordance with embodiments of the present disclosure. For example, such cell growth surface coating and resulting cell expansion may use the Quantum® Cell Expansion System manufactured by Terumo BCT, Inc. in Lakewood, Colo. FIG. 16 illustrates example results for coating a cell growth surface through a coating procedure with ultrafiltration, e.g., about 10-minute positive ultrafiltration coating procedure (10 min+UF), versus an overnight circulating coating procedure. As shown in graph 1600 of FIG. 16, example results may be provided for using cryoprecipitate (CPPT) as a coating agent. Example comparison results may also be provided (not shown in FIG. 16) for using fibronectin (FN) as a coating agent. In this example, two donors, e.g., Donor 1 and Donor 2, may be used to determine an MSC harvest yield. Donor 1 data includes both a Load Cells with Uniform Suspension cell loading procedure (LWUS) and a bulls-eye cell loading procedure (BullsEye Load). Donor 2 data includes results for using a load with uniform suspension cell loading procedure (LWUS).

For Donor 1 and Donor 2, 5×10$^6$ MSC may be loaded into a bioreactor, e.g., bioreactor 501, 601, preconditioned with cell culture media comprised of αMEM+GlutaMAX (Gibco CAT #32561102) and 10% FBS (Hyclone CAT #5H30070.03). Donor 1 MSC may be cultured for 6.8 days and Donor 2 MSC may be cultured for 6.9 days. For Donor 1, n=1 (where n=number of machines or CESs, e.g., Quantum® Systems) for both overnight-coated and 10-minute coated bioreactors. For Donor 2, n=1 for the overnight-coated CES, e.g., Quantum® System, and n=2 for the two 10-minute coated CESs, e.g., Quantum® Systems.

Harvest yields for Donor 1 Quantum® System runs may both be observed to be 1.93×10$^8$ MSC. For example, overnight coating with load with uniform suspension cell loading procedure (LWUS) may yield 193×10$^6$ MSC 1604; and 10-minute ultrafiltration coating with load with uniform suspension cell loading procedure (LWUS) may yield 193×10$^6$ MSC 1608. To confirm efficacy of the 10-minute coating technique with other cell load protocols, an additional comparison may be made between Quantum® Systems loaded using the bulls-eye cell loading procedure (BullsEye Load). The Donor 1 MSC yield for the Overnight coated with bulls-eye cell loading may be observed to be 223×10$^6$ MSC 1612, and MSC yield for the 10-minute ultrafiltration coat with bulls-eye cell loading procedure (BullsEye Load) may be observed to be 215×10$^6$ MSC 1616. The Donor 2 MSC expansion may be observed to yield 191×10$^6$ MSC 1620 from the Overnight coated Quantum® System (n=1) with load with uniform suspension cell loading procedure (LWUS), and 205×10$^6$ MSC 1624 and 193×10$^6$ MSC 1628, respectively, for the two runs of 10-minute ultrafiltration coated Quantum® Systems (n=2) with load with uniform suspension cell loading procedure (LWUS).

Example results (not shown in FIG. 16) may also be provided for using fibronectin (FN) as a coating agent with similar methods and systems as described above. Cell yields for 10-minute ultrafiltration FN coated Quantum® Systems may be observed to be in the range of 40% to 50% of Overnight-coated harvests.

Example 3

Example results of expanding cells by coating a cell growth surface of a cell expansion system, such as CES 500 (FIG. 5) and/or CES 600 (FIG. 6), for example, with various coating procedures are illustrated in FIGS. 17A and 17B. For example, such cell growth surface coating and resulting cell expansion may use the Quantum® Cell Expansion System manufactured by Terumo BCT, Inc. in Lakewood, Colo. FIGS. 17A and 17B illustrate example results for coating a cell growth surface through a coating procedure with ultrafiltration, e.g., about 10-minute ultrafiltration coating procedure (10 min UF), versus coating using an overnight circulating coating procedure or a bulls-eye coating procedure, e.g., a 28-minute modified bulls-eye coating procedure (28 min BE). For example, a 10-minute positive ultrafiltration coating procedure may be used. In such procedures, 5 million MSCs may be loaded into the system, and 25 mL of a cryoprecipitate solution may be used for coating the cell growth surface of a hollow fiber bioreactor. The 28-minute bulls-eye coating time period used to coat the hollow fibers, e.g., fibers 812 (FIG. 8B), may be divided into seven (7) different time periods, each division being four (4) minutes long. During each 4-minute divisional time period, the circulation rate for the IC loop 502, 602 may be changed by adjusting the rate and/or direction of the circulation pump 512, 612. For example, the direction and/or circulation rate for the pump 512, 612 for each subsequent time division may be −300 mL/min, 250 mL/min, −200 mL/min, 150 mL/min, −100 mL/min, 50 mL/min, and −25 mL/min. The results from using these coating procedures with cryoprecipitate (CPPT) may be as shown in FIGS. 17A and 17B.

FIGS. 17A and 17B illustrate example results of using CPPT to coat the cell growth surface of a plurality of hollow fibers using various coating and cell loading procedures, and combinations thereof. As shown in graph 1700 of FIG. 17A, the 28-minute bulls-eye coating procedure (28 min BE) with bulls-eye cell loading procedure (BullsEye) may outperform the following procedures: the 28-minute bulls-eye coating procedure (28 min BE) with load with uniform suspension cell loading procedure (LWUS); the Overnight (o/n) coating procedure with load with uniform suspension cell loading procedure (LWUS); the Overnight coating procedure with bulls-eye cell loading procedure (BullsEye); the 10-minute ultrafiltration coating procedure (10 min UF) with load with uniform suspension cell loading procedure (LWUS); and the 10-minute ultrafiltration coating procedure (10 min UF) with bulls-eye cell loading procedure (BullsEye).

As shown in graph 1700 of FIG. 17A, the 28-minute bulls-eye coating procedure (28 min BE) procedure with bulls-eye cell loading procedure (BullsEye) may yield 2.33×10$^8$ cells 1704 while the Overnight coating procedure with bulls-eye cell loading procedure (BullsEye) may yield 2.23×10$^8$ cells 1708. The Overnight coating procedure with load with uniform suspension cell loading procedure (LWUS) may yield 1.93×10$^8$ cells 1712, while the 28-minute bulls-eye coating (28 min BE) procedure with load with uniform suspension cell loading procedure (LWUS) may yield 1.53×10$^8$ cells 1716. A 10-minute ultrafiltration procedure (10 min UF) with bulls-eye cell loading procedure (BullsEye) may result in 2.15×10$^8$ cells 1720, while a 10-minute ultrafiltration coating procedure (10 min UF) LWUS procedure may yield 1.93×10$^8$ cells 1724.

These example yields are compared in FIG. 17B. Graph 1726 of FIG. 17B illustrates a percentage difference versus control procedure using cryoprecipitate (CPPT) as a coating agent in various coating procedures and cell loading procedures, and combinations thereof. As shown in graph 1726 of FIG. 17B, compared to the Overnight coating procedure with load with uniform suspension cell loading procedure (LWUS) 1728, the Overnight coating procedure with bulls-eye cell loading procedure (BullsEye) may yield 16% 1732 more cells; the 28-minute bulls-eye coating (28 min BE) procedure with load with uniform suspension cell loading procedure (LWUS) may yield 21% 1736 fewer cells; the 28-minute bulls-eye coating procedure (28 min BE) with bulls-eye cell loading procedure (BullsEye) may yield 21% 1740 more cells; the 10-minute ultrafiltration coating procedure (10 min) with load with uniform suspension cell loading procedure (LWUS) may yield substantially the same number 1744 of cells; and the 10-minute ultrafiltration coating procedure (10 min) with bulls-eye cell loading procedure (BullsEye) may yield 11% 1748 more cells.

Example 4

Example results of expanding cells by coating a cell growth surface of a cell expansion system, such as CES 500

(FIG. 5) and/or CES 600 (FIG. 6), for example, with various coating procedures are illustrated in FIGS. 18A and 18B. For example, such cell growth surface coating and resulting cell expansion may use the Quantum® Cell Expansion System manufactured by Terumo BCT, Inc. in Lakewood, Colo. FIGS. 18A and 18B illustrate example results for coating a cell growth surface through a coating procedure with ultra-filtration, e.g., about 10-minute ultrafiltration coating procedure (10 min UF), versus coating using an overnight circulating coating procedure, or a bulls-eye coating (BE) procedure, e.g., a 28-minute modified bulls-eye coating procedure (28 min BE). For example, a 10-minute positive ultrafiltration coating procedure may be used. In such procedures, 5 million MSCs may be loaded into the system, and a 5 mg fibronectin (FN) solution may be used for coating the cell growth surface of a hollow fiber bioreactor. In an embodiment, such 5 mg FN solution may be circulated at 20 mL/minute. In the Quantum® System, such 5 mg FN solution may be circulated at 20 mL/minute in the 189 mL IC loop, according to an embodiment. The 28-minute bulls-eye coating time period used to coat the hollow fibers, e.g., fibers 908 (FIG. 9), may be divided into seven (7) different time periods, each division being four (4) minutes long. During each 4-minute divisional time period, the circulation rate for the IC loop 502, 602 may be changed by adjusting the rate and/or direction of the circulation pump 512, 612. For example, the direction and/or circulation rate for the pump 512, 612 for each subsequent time division may be −300 mL/min, 250 mL/min, −200 mL/min, 150 mL/min, −100 mL/min, 50 mL/min, and −25 mL/min. The results from using these coating procedures with fibronectin (FN) may be as shown in FIGS. 18A and 18B.

FIGS. 18A and 18B illustrate example results of using FN to coat the cell growth surface of a plurality of hollow fibers using various coating and cell loading procedures, and combinations thereof.

The Overnight coating procedure with bulls-eye cell loading procedure (BullsEye) may outperform the following: the Overnight coating procedure with load with uniform suspension cell loading procedure (LWUS); the 28-minute bulls-eye coating (28 min BE) procedure with load with uniform suspension cell loading procedure (LWUS); the 28-minute bulls-eye coating (28 min BE) procedure with bulls-eye cell loading procedure (BullsEye); the 10-minute ultrafiltration coating procedure (10 min UF) with load with uniform suspension cell loading procedure (LWUS); and the 10-minute ultrafiltration coating procedure (10 min UF) with bulls-eye cell loading procedure (BullsEye). As shown in graph 1800 of FIG. 18A, the 28-minute bulls-eye coating procedure (28 min BE) with bulls-eye cell loading procedure (BullsEye) may yield 1.29×108 cells 1804, while the Overnight coating procedure with bulls-eye cell loading procedure (BullsEye) may yield 2.30×108 cells 1808. The Overnight coating procedure with load with uniform suspension cell loading procedure (LWUS) may yield 1×108 cells 1812, while the 28-minute bulls-eye coating procedure (28 min BE) with load with uniform suspension cell loading procedure (LWUS) may yield 9.57×107 cells 1816. A 10-minute ultrafiltration coating procedure (10 min UF) with a bulls-eye cell loading procedure (BullsEye) may result in 7.34×107 cells 1820, while a 10-minute ultrafiltration procedure (10 min UF) with load with uniform suspension cell loading procedure (LWUS) may yield 7.54×107 cells 1824.

These example yields are compared in FIG. 18B. Graph 1826 of FIG. 18B illustrates a percentage difference versus control procedure using fibronectin (FN) as a coating agent using in various coating procedures and cell loading procedures, and combinations thereof. As shown in graph 1826 of FIG. 18B, compared to the Overnight coating procedure with load with uniform suspension cell loading procedure (LWUS) 1828, the Overnight coating procedure with bulls-eye cell loading procedure (BullsEye) may yield 21% 1832 more cells; the 28-minute bulls-eye coating procedure with load with uniform suspension cell loading procedure (LWUS) may yield 50% 1836 fewer cells; the 28-minute bulls-eye coating procedure (28 min BE) with bulls-eye cell loading procedure (BullsEye) may yield 32% 1840 fewer cells; the 10-minute ultrafiltration coating procedure (10 min) with load with uniform suspension cell loading procedure (LWUS) may yield 60% 1844 fewer cells; and the 10-minute ultrafiltration coating procedure (10 min) with bulls-eye cell loading procedure (BullsEye) may yield 61% 1848 fewer cells.

Example 5

Example results of expanding cells by coating a cell growth surface of a cell expansion system, such as CES 500 (FIG. 5) and/or CES 600 (FIG. 6), for example, with various coating procedures are illustrated in FIGS. 19A and 19B. For example, such cell growth surface coating and resulting cell expansion may use the Quantum® Cell Expansion System manufactured by Terumo BCT, Inc. in Lakewood, Colo. FIGS. 19A and 19B illustrate example results for coating a cell growth surface through a coating procedure with coating using an overnight circulating coating procedure versus a bulls-eye coating procedure, e.g., a 56-minute modified bulls-eye coating procedure (56 min BE). In such procedures, 5 million MSCs may be loaded into the system, and a 5 mg fibronectin (FN) solution may be used for coating the cell growth surface of a hollow fiber bioreactor. In an embodiment, such 5 mg FN solution may be circulated at 20 mL/minute. In the Quantum® System, such 5 mg FN solution may be circulated at 20 mL/minute in the 189 mL IC loop, according to an embodiment. The 56-minute bulls-eye coating (56 min BE) time period used to coat the hollow fibers, e.g., fibers 908 (FIG. 9), may be divided into seven (7) different time periods, each division being minutes (8) minutes long. During each 8-minute divisional time period, the circulation rate for the IC loop 502, 602 may be changed by adjusting the rate and/or direction of the circulation pump 512, 612. For example, the direction and/or circulation rate for the pump 512, 612 for each subsequent time division may be −300 mL/min, 250 mL/min, −200 mL/min, 150 mL/min, −100 mL/min, 50 mL/min, and −25 mL/min. The results from using these coating procedures with fibronectin (FN) may be as shown in FIGS. 19A and 19B.

FIGS. 19A and 19B illustrate example results of using FN to coat the cell growth surface of a plurality of hollow fibers using various coating and cell loading procedures, and combinations thereof.

The Overnight coating procedure with uniform suspension cell loading procedure (LWUS) may outperform the following: the 56-minute bulls-eye coating (56 min BE) procedure with uniform suspension cell loading procedure (LWUS) and the 56-minute bulls-eye coating procedure (56 min BE) with BullsEye loading procedure. As shown in graph 1900 of FIG. 19A, the 56-minute bulls-eye coating procedure (56 min BE) with bulls-eye cell loading procedure (BullsEye) may yield 1.58×108 cells 1904 in a first run and 1.59×108 cells 1908 in a second run. The 56-minute bulls-eye coating procedure (56 min BE) with uniform suspension cell loading (LWUS) may yield 1.38×108 cells 1912. The Overnight coating procedure with uniform suspension cell loading procedure (LWUS) may yield 2.75×108 cells 1916.

These example yields are compared in FIG. 19B. Graph 1920 of FIG. 19B illustrates a percentage difference versus control procedure using fibronectin (FN) as a coating agent using various coating procedures and cell loading procedures, and combinations thereof. As shown in graph 1920 of FIG. 19B, compared to the Overnight coating procedure with load with uniform suspension cell loading procedure (LWUS) 1924, the 56-minute bulls-eye coating procedure (56 min BE) with uniform suspension cell loading procedure (LWUS) may yield 50% 1928 fewer cells; the 56-minute bulls-eye coating procedure (56 min BE) with bulls-eye cell loading procedure (BullsEye) may yield 43% 1932 fewer cells in a first run, and 42% 1936 fewer cells in a second run.

Example 6

The objective of this study is to characterize the expansion of human bone marrow derived mesenchymal stem cells (hMSCs) using two unique cell seeding methodologies in the QUANTUM® cell expansion system.

The current cell loading procedure used on the QUANTUM cell expansion system for pre-selected hMSCs distributes the cells in the bioreactor via uniform cell suspension. The cells are loaded into the IC Circulation loop of the QUANTUM cell expansion system and then circulated at relatively high flow rates (200 mL/min) for two minutes. This circulation method, coinciding with deliberate bioreactor motion, results in a uniform suspension of cells. Once the cells are uniformly suspended, circulation and bioreactor motion stops and the cells settle onto the bioreactor surface.

One limitation of this cell loading procedure is that only the trough of the bioreactor fiber is seeded with cells. hMSCs are frequently seeded at a specified cell density (e.g., 500 cells/cm2). In order to achieve a specified seed density, only approximately 50% of the bioreactor surface area can be considered when determining the appropriate number of cells to load. At 500 cells/cm2, the QUANTUM cell expansion system bioreactor can be seeded with 10.5E+06 cells (500 cells/cm2×21000 cm2). However, only 50% of the bioreactor surface area can be considered "seed able" due to the aforementioned mechanics of the current cell load protocol. In addition, expanding cells attempting to migrate to the "unseedable" surface of the bioreactor must overcome gravity in order to utilize that surface. It is theorized here that migrating cells may take the path of least resistance; resulting in rapid confluence within the cell population compared to those expanded in its flask counter-part.

A total of seven sterilized Quantum CES Disposable sets with a bioreactor may be fibronectin coated (5 mg) overnight. All Quantum systems may be seeded with pre-cultured hMSCs. One Quantum cell expansion system may use the current Load with Circulation Task and serve as the experiment control. Three Quantum cell expansion systems may use "Load with Circulation Task: Modification 1" (Modification 1) and three Quantum cell expansion systems may use "Load with Circulation Task: Modification 2" (Modification 2).

Disposable Sets: All bioreactors may be integrated into a QUANTUM cell expansion system (CES) disposable set and sterilized with ethylene oxide.

Cell Source and Density: The bioreactor that may be used may have a 2.1 m2 inner (IC) surface area. As a result, an adjustment to seeding densities for control flasks may need to be made based on the bioreactor volume fraction of the IC loop. All bioreactors may be uniformly loaded with a maximum of 20E+06 pre-selected MSCs (existing passages 1-3) from a direct re-load of the same cell source. Cells from a single donor are preferred. Seed three (3) T25 control flasks with hMSCs at the same density per cm2 as the bioreactor for comparative purposes.

CES Media IC Input Q Management & Harvest: The media feed rate (IC Input Q) may be doubled when the glucose levels fall below 70 mg/dL; the IC Input Q may be doubled a second time in the course of one day if the glucose values continue to fall below 70 mg/dL. All disposable sets may be harvested at the same time and no later than Day 8 to limit potential aggregation. Cell harvest time may be determined as a result of the metabolic characteristics displayed by the cell cultures. The target harvest time may be post-log phase growth of the cells.

Post-Harvest Evaluation: Evaluations may be performed on each of the harvest products. These evaluations may include cell count and viability.

Quantum CES Cell Load Modification 1

The current cell load procedure may be performed with the following modifications shown in bold. After allowing the cells to attach for 5 minutes, all bioreactors may be rotated 180 degrees to allow unattached cells to settle to the top of the hollow fiber membrane for an additional 5 minutes. Then bioreactor may be rotated back to the home horizontal position and proceed with the expansion protocol. The rationale for the modification is to distribute the cells over the entire surface area of the bioreactor hollow fiber.

Day: 0 Attach Cells with One (1) Rotation

Purpose: enables adherent cells to attach to the bioreactor membrane while allowing flow on the EC circulation loop. The pump flow rate to the IC loop may be set to zero.

Table 34 describes the bags of solution that may be attached to each line when performing Attach Cells. These solutions and corresponding volumes are based on the default settings for this task.

Table 34: Solutions for Attach Cells Modification 1
Table 34: Solutions for Attach Cells

TABLE 34

Solutions for Attach Cells

| Bag | Solution in Bag | Volume (estimate based on factory default) |
| --- | --- | --- |
| Cell Inlet | None | N/A |
| Reagent | None | N/A |
| IC Media | Media with Protein | 6 mL/hour |
| Wash | None | N/A |
| EC Media | None | N/A |

Cells pathway: Task>Load and Attach>Attach Cells

Enter the values for each setting for Attach Cells shown in Protocol Table 35-37.

Table 35: Task>Load and Attach>Attach Cells, Step 1 Modification 1

TABLE 35

Task Settings for Attach Cells, Step 1

| Setting | Factory Default | Laboratory Default | Modifications |
| --- | --- | --- | --- |
| IC Inlet | None | | |
| IC Inlet Rate | 0 | | |
| IC Circulation Rate | 0 | | |

TABLE 35-continued

Task Settings for Attach Cells, Step 1

| Setting | Factory Default | Laboratory Default | Modifications |
|---|---|---|---|
| EC Inlet | EC Media | IC Media | |
| EC Inlet Rate | 0 | | |
| EC Circulation Rate | 0 | | |
| Outlet | EC Waste | | |
| Rocker Control | Stationary (0°) | | Stationary 180° |
| Stop Condition | Manual | | Time: 5 minutes |

Table 36: Task>Load and Attach>Attach Cells, Step 2 Modification 1

TABLE 36

Task Settings for Attach Cells, Step 2

| Setting | Factory Default | Laboratory Default | Modifications |
|---|---|---|---|
| IC Inlet | None | | |
| IC Inlet Rate | 0 | | |
| IC Circulation Rate | 0 | | |
| EC Inlet | EC Media | IC Media | |
| EC Inlet Rate | 0 | | |
| EC Circulation Rate | 0 | | |
| Outlet | EC Waste | | |
| Rocker Control | Stationary (0°) | | |
| Stop Condition | Manual | | Time: 5 minutes |

Table 37: Task>Load and Attach>Attach Cells, Step 3 Modification 1

TABLE 37

Task Settings for Attach Cells, Step 3

| Setting | Factory Default | Laboratory Default | Modifications |
|---|---|---|---|
| IC Inlet | None | | |
| IC Inlet Rate | 0 | | |
| IC Circulation Rate | 0 | | |
| EC Inlet | EC Media | IC Media | |
| EC Inlet Rate | 0.1 | | |
| EC Circulation Rate | 30 | | |
| Outlet | EC Waste | | |
| Rocker Control | Stationary (0°) | | Stationary 180° |
| Stop Condition | Manual | | |

Quantum CES Cell Load Modification 2

The current cell load procedure, pre-selected MSC Expansion Protocol, may be performed with the following modifications shown in bold. Cells may be attached to the top of the hollow fiber by rotating the bioreactor to the 180 degree position during the cell attachment phase (18-24 hours). Then rotate the bioreactor back to the home position and proceed with the expansion protocol. The rationale for the modification is to allow gravity to influence the direction of cell migration toward the empty growth surface during cell expansion.

The force of gravity may be used to "influence" the cell migration during expansion. This may be accomplished by seeding the cells as described in the current cell load procedure, then during expansion the bioreactor may be rotated 180°. In this configuration the unoccupied growth surface of the bioreactor is below the seeded cells. The cells may then expand in the direction of least resistance (e.g., downward, aided by gravity).

Day: 0 Attach Cells with One (1) Rotation

Purpose: enables adherent cells to attach to the bioreactor membrane while allowing flow on the EC circulation loop. The pump flow rate to the IC loop may be set to zero.

Table 38 describes the bags of solution that may be attached to each line when performing Attach Cells. These solutions and corresponding volumes are based on the default settings for this task.

Table 38: Solutions for Attach Cells Modification 2

TABLE 38

Solutions for Attach Cells

| Bag | Solution in Bag | Volume (estimate based on factory default) |
|---|---|---|
| Cell Inlet | None | N/A |
| Reagent | None | N/A |
| IC Media | Media with Protein | 6 mL/hour |
| Wash | None | N/A |
| EC Media | None | N/A |

Cells pathway: Task>Load and Attach>Attach Cells

Table 39: Task>Load and Attach>Attach Cells Modification 2

TABLE 39

Task Settings for Attach Cells, Step 1

| Setting | Factory Default | Laboratory Default | Modifications |
|---|---|---|---|
| IC Inlet | None | | |
| IC Inlet Rate | 0 | | |
| IC Circulation Rate | 0 | | |
| EC Inlet | EC Media | IC Media | |
| EC Inlet Rate | 0.1 | | |
| EC Circulation Rate | 30 | | |
| Outlet | EC Waste | | |
| Rocker Control | Stationary (0°) | | Stationary 180° |
| Stop Condition | Manual | | |

The results may be as follows:

TABLE 40

| Quantum Run | Modification | hMSC Seeding | hMSC Seeding//$cm^2$ | Harvest hMSC | Harvest hMSC/$cm^2$ | Percent Increase |
|---|---|---|---|---|---|---|
| Q621 | Control | 1.05E+07 | 500 | 2.56E+08 | 12,194 | 0% |
| Q622 | Mod 1 | 1.05E+07 | 500 | 3.02E+08 | 14,376 | 18% |
| Q623 | Mod 1 | 1.05E+07 | 500 | | | |
| Q624 | Mod 1 | 1.05E+07 | 500 | 3.49E+08 | 16,596 | 51% |

TABLE 41

| Quantum Run | Modification | hMSC Seeding | hMSC Seeding//cm$^2$ | Harvest hMSC | Harvest hMSC/cm$^2$ | Percent Increase |
|---|---|---|---|---|---|---|
| | Control | 1.05E+07 | 500 | 2.56E+08 | 12,194 | 0% |
| Average | Mod 1 | 1.05E+07 | 500 | 3.40E+08 | 16,197 | 35% |

TABLE 42

| Load Condition | # of Cells Seeded | # Cells Harvested | Doubling Time (hrs) |
|---|---|---|---|
| Control | 10.5 × 10$^6$ | 256 × 10$^6$ | 34.9 |
| Gravity Influenced Expansion (Modification 2) | 10.5 × 10$^6$ | 345 × 10$^6$ | 30.9 |
| Gravity Influenced Expansion (Modification 2) | 10.5 × 10$^6$ | 347 × 10$^6$ | 31.9 |
| Gravity Influenced Expansion (Modification 2) | 10.5 × 10$^6$ | 388 × 10$^6$ | 31.9 |

Example 7

The Bull's Eye cell loading procedure is a series of steps designed to increase cell yield by allowing for a more even distribution of cells within the bioreactor of the QUANTUM® cell expansion system and by reducing the number of cells lost during a seeding process.

The Bull's Eye cell loading technique for the QUANTUM cell expansion system provides a series of steps that include and add to the 'Load Cells with Uniform Suspension' protocol (Quantum Cell Expansion System Operator's Manual for Software Version 2.0) that is commonly used to seed the bioreactor. In Load Cells with Uniform Suspension (LCWUS), suspended cells have a single opportunity to enter and attach to the internal surface of one fiber of the bioreactor after the cell suspension is circulated through the IC loop at 200 mL/min. Bull's Eye may allow cells that do not attach after the initial suspension and those that may be left in the IC loop rather than in the bioreactor to be re-suspended and transported to a different fiber within the bioreactor for subsequent attachment.

The Bull's Eye load may operate on the principle that a cell suspension introduced to the bioreactor via circulation of the IC loop may pass through a different set of bioreactor fibers depending on the rate of circulation of that cell suspension in the IC loop.

Following an initial 200 mL/min suspension cycle in loading cells with uniform suspension (LCWUS), the cell suspension in the IC loop may be circulated alternately in the positive and negative directions at sequentially lower circulation rates: −100 mL/min, 50 mL/min, −25 mL/min. Each progressively slower cycle of the IC loop may allow those cells still left in suspension an additional opportunity to enter and attach to the inner surface of a bioreactor fiber.

Each cycling of the fluid in the IC loop may be followed by a 7-minute cell-attachment period during which the IC circulation rate may be zero. MSC cells have been demonstrated to attach within 5 minutes to the inner surface of a fiber in a bioreactor used in the QUANTUM cell expansion system. As such, the 7-minute attachment may allow for 5 minutes for cell attachment, and 2 extra minutes to allow for slower-attaching cells. The four total cycles of cell suspension and cell attachment in the IC loop may be followed by a 24 hr attachment period after which an appropriate cell feeding schedule may be input as desired.

Day: −1 Coat Bioreactor

Purpose: coats the bioreactor membrane with a reagent.

Step 1: loads a reagent into the IC loop until the bag is empty.

Step 2: chases the reagent from the ARC into the IC loop.

Step 3: circulates the reagent in the IC loop.

Before starting this task, the following preconditions may be satisfied:

Include at least 40 mL of air in the cell inlet bag.

Table 43 describes the bags of solution that may be used to attach to each line when performing Coat Bioreactor. These solutions and corresponding volumes may be based on the default settings for this task.

TABLE 43

Solutions for Coat Bioreactor

| Bag | Solution in Bag | Volume (estimation based on factory default values) |
|---|---|---|
| Cell Inlet | None | N/A |
| Reagent | Fibronectin | 5 mg Fibronectin in 100 mL PBS |
| IC Media | None | N/A |
| Wash | PBS | 0.1 L + 6 mL/hr (overnight) |
| EC Media | None | N/A |

Coat Bioreactor pathway: Task>System Management>Coat Bioreactor

Enter the values for each setting for step 1 shown in Table 44.

Table 44: Step 1 for Coat Bioreactor

TABLE 44

Step 1 for Coat Bioreactor

| Setting | Factory Default | Laboratory Default | Modifications |
|---|---|---|---|
| IC Inlet | Reagent | | |
| IC Inlet Rate | 10 mL/min | | |
| IC Circulation Rate | 100 mL/min | | |
| EC Inlet | None | | |
| EC Inlet Rate | 0 mL/min | | |
| EC Circulation Rate | 30 mL/min | | |
| Outlet | EC Outlet | | |
| Rocker Control | Stationary (0°) | | |
| Stop Condition | Empty Bag | | |

Enter the values for each setting for step 2 shown in Table 45.

TABLE 45

Step 2 Setting for Coat Bioreactor

| Setting | Factory Default | Laboratory Default | Modifications |
|---|---|---|---|
| IC Inlet | Wash | | |
| IC Inlet Rate | 10 mL/min | | |
| IC Circulation Rate | 100 mL/min | | |
| EC Inlet | None | | |
| EC Inlet Rate | 0 mL/min | | |
| EC Circulation Rate | 30 mL/min | | |
| Outlet | EC Outlet | | |
| Rocker Control | Stationary (0°) | | |
| Stop Condition | IC Volume (22 mL) | | |

Enter the values for each setting for step 3 shown in Table 46.

TABLE 46

Step 3 Settings for Coat Bioreactor

| Setting | Factory Default | Laboratory Default | Modifications |
|---|---|---|---|
| IC Inlet | None | | |
| IC Inlet Rate | 0 mL/min | | |
| IC Circulation Rate | 20 mL/min | | |
| EC Inlet | Wash | | |
| EC Inlet Rate | 0.1 mL/min | | |
| EC Circulation Rate | 30 mL/min | | |
| Outlet | EC Outlet | | |
| Rocker Control | Stationary (0°) | | |
| Stop Condition | Manual | | |

Day: 0 IC EC Washout

Purpose: used to replace the fluid on both the IC circulation loop and the EC circulation loop. The replacement volume is specified by the number of IC Volumes and EC Volumes exchanged. Table 47 describes the bags of solution that may be attached to each line when performing IC EC Washout. These solutions and corresponding volumes may be based on the default settings for this task.

TABLE 47

Solutions for IC EC Washout

| Bag | Solution in Bag | Volume (estimation based on factory default values) |
|---|---|---|
| Cell Inlet | None | N/A |
| Reagent | None | N/A |
| IC Media | Media with Protein | 1.4 L |
| Wash | None | N/A |
| EC Media | None | N/A |

IC EC Washout pathway: Task>Washout>IC EC Washout

Confirm the values for each setting for IC EC Washout shown in Table 48.

TABLE 48

Task Settings for IC EC Washout

| Setting | Factory Default | Laboratory Default | Modifications |
|---|---|---|---|
| IC Inlet | IC Media | | |
| IC Inlet Rate | 100 mL/min | | |
| IC Circulation Rate | −17 mL/min | | |
| EC Inlet | EC Media | IC Media | |
| EC Inlet Rate | 148 mL/min | | |
| EC Circulation Rate | −1.7 mL/min | | |
| Outlet | IC and EC Outlet | | |
| Rocker Control | In Motion (−90°, 180°, 1 sec) | | |
| Stop Condition | Exchange (2.5 IC Volumes) (2.5 EC Volumes) | | |

Day: 0 Condition Media

Follow the instructions in this task to allow the media to reach equilibrium with the provided gas supply before loading the cells. This task may include two separate steps:

Step 1: provides rapid contact between the media and the gas supply by using a high EC circulation rate.

Step 2: maintains the system in a proper state until the operator is ready to load the cells.

Table 49 describes the bags of solution that may be attached to each line when performing Condition Media. These solutions and corresponding volumes may be based on the default settings for this task.

TABLE 49

Solutions for Condition Media

| Line | Solution in Bag | Volume (estimation based on factory default values) |
|---|---|---|
| Cell Inlet | None | N/A |
| Reagent | None | N/A |
| IC Media | None | N/A |
| Wash | None | N/A |
| EC Media | Media without Protein | 0.1 L plus 6 mL/hour |

Condition Media pathway: Task>System Management>Condition Media

Enter the values for each setting for step 1 shown in Table 50.

TABLE 50

Step 1 Settings for Condition Media

| Setting | Factory Default | Laboratory Default | Modifications |
|---|---|---|---|
| IC Inlet | None | | |
| IC Inlet Rate | 0 mL/min | | |
| IC Circulation Rate | 100 mL/min | | |
| EC Inlet | EC Media | IC Media | |
| EC Inlet Rate | 0.1 mL/min | | |
| EC Circulation Rate | 250 mL/min | | |
| Outlet | EC Outlet | | |
| Rocker Control | Stationary (0°) | | |
| Stop Condition | Time (10 min) | | |

Enter the values for each setting for step 2 shown in Table 51.

TABLE 51

Step 2 Settings for Condition Media

| Setting | Factory Default | Laboratory Default | Modifications |
|---|---|---|---|
| IC Inlet | None | | |
| IC Inlet Rate | 0 mL/min | | |
| IC Circulation Rate | 100 mL/min | | |
| EC Inlet | EC Media | IC Media | |
| EC Inlet Rate | 0.1 mL/min | | |
| EC Circulation Rate | 30 mL/min | | |
| Outlet | EC Outlet | | |
| Rocker Control | Stationary (0°) | | |
| Stop Condition | Manual | | |

Day: 0 Load Cells with Uniform Suspension

Purpose: loads the cells into the bioreactor from the cell inlet bag until the bag is empty. This task only uses IC circulation to distribute the cells and does not attempt to chase the cells from the line into the bioreactor. This task may include three separate steps.

Step 1: loads the cells from the cell inlet bag into the bioreactor.

Step 2: chases the cells from the ARC to the bioreactor. Larger chase volumes spread the cells and move them towards the IC outlet.

Step 3: promotes distribution of cells across membrane via IC circulation and no IC inlet thus no ultrafiltration.

Before starting this task, the following preconditions may be satisfied:

Include at least 40 mL of air in the cell inlet bag.

Table 52 describes the bags of solution that may be attached to each line when performing Load Cells With Uniform Suspension. These solutions and corresponding volumes may be based on the default settings for this task.

TABLE 52

Solutions for Load Cells With Uniform Suspension

| Line | Solution in Bag | Volume (estimation based on factory default values) |
|---|---|---|
| Cell Inlet | Cells | N/A |
| Reagent | None | N/A |
| IC Media | Media with Protein | 0.2 L |
| Wash | None | N/A |
| EC Media | None | N/A |

Load Cells with Uniform suspension pathway: Task>Load and Attach>Load Cells with Uniform Suspension Confirm the values for each setting for step 1 shown in Table 53.

TABLE 53

Step 1 Settings for Load Cells With Uniform Suspension

| Setting | Factory Default | Laboratory Default | Modifications |
|---|---|---|---|
| IC Inlet | Cell | | |
| IC Inlet Rate | 50 mL/min | | 25 mL/min |

TABLE 53-continued

Step 1 Settings for Load Cells With Uniform Suspension

| Setting | Factory Default | Laboratory Default | Modifications |
|---|---|---|---|
| IC Circulation Rate | 200 mL/min | | 150 mL/min |
| EC Inlet | None | | |
| EC Inlet Rate | 0 mL/min | | |
| EC Circulation Rate | 30 mL/min | | |
| Outlet | EC Outlet | | |
| Rocker Control | In Motion (−90°, 180°, 1 sec) | | |
| Stop Condition | Empty Bag | | |

Confirm the values for each setting for step 2 shown in Table 54.

TABLE 54

Step 2 Settings for Load Cells with Uniform Suspension

| Setting | Factory Default | Laboratory Default | Modifications |
|---|---|---|---|
| IC Inlet | IC Media | | |
| IC Inlet Rate | 50 mL/min | | 25 mL/min |
| IC Circulation Rate | 200 mL/min | | 150 mL/min |
| EC Inlet | None | | |
| EC Inlet Rate | 0 mL/min | | |
| EC Circulation Rate | 30 mL/min | | |
| Outlet | EC Outlet | | |
| Rocker Control | In Motion (−90°, 180°, 1 sec) | | |
| Stop Condition | IC Volume (22 mL) | | |

Confirm the values for each setting for step 3 shown in Table 55.

TABLE 55

Step 3 Settings for Load Cells with Uniform Suspension

| Setting | Factory Default | Laboratory Default | Modifications |
|---|---|---|---|
| IC Inlet | None | | |
| IC Inlet Rate | 0 mL/min | | |
| IC Circulation Rate | 200 mL/min | | |
| EC Inlet | None | | |
| EC Inlet Rate | 0 mL/min | | |
| EC Circulation Rate | 30 mL/min | | |
| Outlet | EC Outlet | | |
| Rocker Control | In Motion (−90°, 180°, 1 sec) | | |
| Stop Condition | Time (2.0 min) | | |

Day: 0 Bull's Eye Attachment

Purpose: allows adherent cells to attach to the bioreactor membrane while allowing flow on the EC circulation loop. The pump flow rate to the IC loop may be set to zero.

Step 1: Allows cells 7 minutes to attach to the inner surface of the bioreactor at 180°.

Step 2: Circulates the IC fluid and the remaining suspended cells at a high rate in a direction opposite to the initial load.

Step 3: This step is a second 7.0 minute allowance for further cell attachment. Those cells that were relocated from the IC loop or from a different region of the bioreactor will be given a chance to settle and adhere to the bioreactor.

Step 4: Again re-circulates those cells remaining in the IC loop and those cells that have yet to attach to a surface. Circulation may be in the positive direction and the circulation rate may be lower this time to avoid removing those cells that have already attached and to seed preferentially regions of the bioreactor that may not have been seeded in previous steps.

Step 5: This step is a third 7.0 minute allowance for further cell attachment. Those cells that were relocated from the IC loop or from a different region of the bioreactor will be given a chance to settle and adhere to the bioreactor.

Step 6: re-circulates those cells remaining in the IC loop and those cells that have yet to attach to a surface. Circulation may be in the negative direction and the circulation rate is lower this time to avoid removing those cells that have already attached.

Step 7: 24 hour attach cells phase. Cells may have 24 hours to anchor solidly to the bioreactor before feeding begins.

Table 56 describes the bags of solution that may be attached to each line when performing Bull's Eye Attachment. These solutions and corresponding volumes may be based on the default settings for this task.

TABLE 56

Solutions for Bull's Eye Attachment

| Bag | Solution in Bag | Volume (estimation based on factory default values) |
| --- | --- | --- |
| Cell Inlet | None | N/A |
| Reagent | None | N/A |
| IC Media | Media with Protein | 6 mL/hour |
| Wash | None | N/A |
| EC Media | None | N/A |

Bull's Eye attachment Cells pathway: Task>Custom>Custom

Enter the values for each setting shown in Table 57.

TABLE 57

Step 1 Task Settings for Bull's Eye Attachment

| Setting | Factory Default | Laboratory Default | Modifications |
| --- | --- | --- | --- |
| IC Inlet | None | | |
| IC Inlet Rate | 0 mL/min | | |
| IC Circulation Rate | 0 mL/min | | |
| EC Inlet | EC Media | | |
| EC Inlet Rate | 0.1 mL/min | | |
| EC Circulation Rate | 30 mL/min | | |
| Outlet | EC Outlet | | |
| Rocker Control | Stationary (0°) | Stationary (180°) | |
| Stop Condition | Time (7.0 min) | | |

Enter the values for each setting shown in Table 58.

TABLE 58

Step 2 Task Settings for Bull's Eye Attachment

| Setting | Factory Default | Laboratory Default | Modifications |
| --- | --- | --- | --- |
| IC Inlet | None | | |
| IC Inlet Rate | 0 mL/min | | |
| IC Circulation Rate | 0 mL/min | | −100 mL/min |
| EC Inlet | None | | |
| EC Inlet Rate | 0 mL/min | | |
| EC Circulation Rate | 0 mL/min | | 30 mL/min |
| Outlet | EC Outlet | | |
| Rocker Control | Stationary | | In Motion (−90°, 180°, 1 sec) |
| Stop Condition | Manual | | Time (2.0 min) |

Enter the values for each setting shown in Table 59.

TABLE 59

Step 3 Task Settings for Bull's Eye Attachment

| Setting | Factory Default | Laboratory Default | Modifications |
| --- | --- | --- | --- |
| IC Inlet | None | | |
| IC Inlet Rate | 0 mL/min | | |
| IC Circulation Rate | 0 mL/min | | |
| EC Inlet | EC Media | IC Media | |
| EC Inlet Rate | 0.1 mL/min | | |
| EC Circulation Rate | 30 mL/min | | |
| Outlet | EC Outlet | | |
| Rocker Control | Stationary (0°) | | |
| Stop Condition | Time (7.0 min) | | |

Enter the values for each setting shown in Table 60.

TABLE 60

Step 4 Task Settings for Bull's Eye Attachment

| Setting | Factory Default | Laboratory Default | Modifications |
| --- | --- | --- | --- |
| IC Inlet | None | | |
| IC Inlet Rate | 0 mL/min | | |
| IC Circulation Rate | 0 mL/min | | 50 mL/min |
| EC Inlet | None | | |
| EC Inlet Rate | 0 mL/min | | |
| EC Circulation Rate | 0 mL/min | | 30 mL/min |
| Outlet | EC Outlet | | |
| Rocker Control | Stationary | | In Motion (−90°, 180°, 1 sec) |
| Stop Condition | Manual | | Time (4.0 min) |

Enter the values for each setting shown in Table 61.

TABLE 61

Step 5 Task Settings for Bull's Eye Attachment

| Setting | Factory Default | Laboratory Default | Modifications |
|---|---|---|---|
| IC Inlet | None | | |
| IC Inlet Rate | 0 mL/min | | |
| IC Circulation Rate | 0 mL/min | | |
| EC Inlet | EC Media | | |
| EC Inlet Rate | 0.1 mL/min | | |
| EC Circulation Rate | 30 mL/min | | |
| Outlet | EC Outlet | | |
| Rocker Control | Stationary (0°) | | |
| Stop Condition | Time (7.0 min) | | |

Enter the values for each setting shown in Table 62.

TABLE 62

Step 6 Task Settings for Bull's Eye Attachment

| Setting | Factory Default | Laboratory Default | Modifications |
|---|---|---|---|
| IC Inlet | None | | |
| IC Inlet Rate | 0 mL/min | | |
| IC Circulation Rate | 0 mL/min | | −25 mL/min |
| EC Inlet | None | | |
| EC Inlet Rate | 0 mL/min | | |
| EC Circulation Rate | 0 mL/min | | 30 mL/min |
| Outlet | EC Outlet | | |
| Rocker Control | Stationary | | In Motion (−90°, 180°, 1 sec) |
| Stop Condition | Manual | | Time (8.0 min) |

Enter the values for each setting shown in Table 63.

TABLE 63

Task Settings for Bull's Eye Attachment

| Setting | Factory Default | Laboratory Default | Modifications |
|---|---|---|---|
| IC Inlet | None | | |
| IC Inlet Rate | 0 mL/min | | |
| IC Circulation Rate | 0 mL/min | | |
| EC Inlet | EC Media | IC Media | |
| EC Inlet Rate | 0.1 mL/min | | |
| EC Circulation Rate | 30 mL/min | | |
| Outlet | EC Outlet | | |
| Rocker Control | Stationary (0°) | | |
| Stop Condition | Manual | | Time (1440.0 min) |

Day: 1 Feed Cells

Purpose: continuously adds a low flow rate to the IC circulation loop and/or the EC circulation loop. There are several outlet settings that can be used to remove the fluid added to the system during this task.

Table 64 describes the bags of solution that may be attached to each line when performing Feed Cells. These solutions and corresponding volumes may be based on the default settings for this task.

TABLE 64

Solutions for Feed Cells

| Bag | Solution in Bag | Volume (estimation based on factory default values) |
|---|---|---|
| Cell Inlet | None | N/A |
| Reagent | None | N/A |
| IC Media | Media with Protein | 6 mL/hour |
| Wash | None | N/A |
| EC Media | None | N/A |

Confirm the values for each setting for step 1 for shown in Table 65.

TABLE 65

Task Settings for Feed Cells

| Setting | Factory Default | Laboratory Default | Modifications |
|---|---|---|---|
| IC Inlet | IC Media | | |
| IC Inlet Rate | 0.1 mL/min | | |
| IC Circulation Rate | 20 mL/min | | |
| EC Inlet | None | | |
| EC Inlet Rate | 0 mL/min | | |
| EC Circulation Rate | 30 mL/min | | |
| Outlet | IC Outlet | | |
| Rocker Control | Stationary (0°) | | |
| Stop Condition | Manual | | |

Increase IC Inlet rate as needed.

Release Adherent Cells and Harvest

Purpose: releases cells from the membrane, leaving the cells in the IC loop and transfers cells in suspension from the IC circulation loop, including cells in the bioreactor, into the harvest bag.

Step 1: performs the IC EC Washout task in preparation for adding a reagent. For example, the system replaces IC EC media with PBS to remove protein, Ca++, and Mg++ in preparation for adding trypsin.

Step 2: loads a reagent into the system until the bag is empty.

Step 3: chases the reagent into the IC loop.

Step 4: mixes the reagent within the IC loop.

Step 5: transfers cells in suspension from the IC circulation loop, including cells in the bioreactor, to the harvest bag.

Before starting this task, the following preconditions may be satisfied:

Include at least 40 mL of air on the cell inlet bag.

Table 66 describes the bags of solution that may be attached to each line when performing Release Adherent Cells And Harvest. These solutions and corresponding volumes may be based on the default settings for this task.

TABLE 66

Solutions for Release Adherent Cells And Harvest

| Bag | Solution in Bag | Volume (estimation based on factory default values) |
|---|---|---|
| Cell Inlet | None | N/A |
| Reagent | Trypsin | 180 mL |

TABLE 66-continued

Solutions for Release Adherent Cells And Harvest

| Bag | Solution in Bag | Volume (estimation based on factory default values) |
|---|---|---|
| IC Media | Media with Protein | 0.6 L |
| Wash | PBS | 1.4 L |
| EC Media | None | N/A |

Release Adherent Cells pathway: Task>Release and Harvest>Release Adherent Cells And Harvest Confirm the values for each setting for step 1 shown in Table 67.

TABLE 67

Step 1 Settings for Release Adherent Cells And Harvest

| Setting | Factory Default | Laboratory Default | Modifications |
|---|---|---|---|
| IC Inlet | Wash | | |
| IC Inlet Rate | 100 mL/min | | |
| IC Circulation Rate | −17 mL/min | | |
| EC Inlet | Wash | | |
| EC Inlet Rate | 148 mL/min | | |
| EC Circulation Rate | −1.7 mL/min | | |
| Outlet | IC and EC Outlet | | |
| Rocker Control | In Motion (−90°, 180°, 1 sec) | | |
| Stop Condition | Exchange (2.5 IC Volumes) (2.5 EC Volumes) | | |

Confirm the values for each setting for step 2 shown in Table 68.

TABLE 68

Step 2 Settings for Release Adherent Cells And Harvest

| Setting | Factory Default | Laboratory Default | Modifications |
|---|---|---|---|
| IC Inlet | Reagent | | |
| IC Inlet Rate | 50 mL/min | | |
| IC Circulation Rate | 300 mL/min | | |
| EC Inlet | None | | |
| EC Inlet Rate | 0 mL/min | | |
| EC Circulation Rate | 30 mL/min | | |
| Outlet | EC Outlet | | |
| Rocker Control | In Motion (−90°, 180°, 1 sec) | | |
| Stop Condition | Empty Bag | | |

Confirm the values for each setting for step 3 shown in Table 69.

TABLE 69

Step 3 Settings for Release Adherent Cells And Harvest

| Setting | Factory Default | Laboratory Default | Modifications |
|---|---|---|---|
| IC Inlet | Wash | | |
| IC Inlet Rate | 50 mL/min | | |
| C Circulation Rate | 300 mL/min | | |

TABLE 69-continued

Step 3 Settings for Release Adherent Cells And Harvest

| Setting | Factory Default | Laboratory Default | Modifications |
|---|---|---|---|
| EC Inlet | None | | |
| EC Inlet Rate | 0 mL/min | | |
| EC Circulation Rate | 30 mL/min | | |
| Outlet | EC Outlet | | |
| Rocker Control | In Motion (−90°, 180°, 1 sec) | | |
| Stop Condition | IC Volume (22 mL) | | |

Confirm the values for each setting for step 4 shown in Table 70.

TABLE 70

Step 4 Settings for Release Adherent Cells And Harvest

| Setting | Factory Default | Laboratory Default | Modifications |
|---|---|---|---|
| IC Inlet | None | | |
| IC Inlet Rate | 0 mL/min | | |
| IC Circulation Rate | 300 mL/min | | |
| EC Inlet | None | | |
| EC Inlet Rate | 0 mL/min | | |
| EC Circulation Rate | 30 mL/min | | |
| Outlet | EC Outlet | | |
| Rocker Control | In Motion (−90°, 180°, 1 sec) | | |
| Stop Condition | Time (4 min) | | |

Confirm the values for each setting for step 5 shown in Table 71.

TABLE 71

Step 5 Settings for Release Adherent Cells And Harvest

| Setting | Factory Default | Laboratory Default | Modifications |
|---|---|---|---|
| IC Inlet | IC Media | | |
| IC Inlet Rate | 400 mL/min | | |
| IC Circulation Rate | −70 mL/min | | |
| EC Inlet | EC Media | IC Media | |
| EC Inlet Rate | 60 mL/min | | |
| EC Circulation Rate | 30 mL/min | | |
| Outlet | Harvest | | |

TABLE 71-continued

Step 5 Settings for Release Adherent Cells And Harvest

| Setting | Factory Default | Laboratory Default | Modifications |
|---|---|---|---|
| Rocker Control | In Motion (−90°, 180°, 1 sec) | | |
| Stop Condition | IC Volume (378 mL) | | |

The results of the study may be as follows:

TABLE 72

| Load | Time (days) | #Cells Loaded | #Cells Harvested | Viability | Agg (0-5) | 69% Adjusted Doubling Time (Hrs) | Unadjusted Doubling Time (Hrs) | Mean Flask Doubling Time (Hrs) |
|---|---|---|---|---|---|---|---|---|
| BullsEye | 4.8 | 1.52E+06 | 1.97E+08 | 98.1% | 2 | 27.2 | 31.2 | 24.1 |
| BullsEye | 4.8 | 1.52E+06 | 2.05E+08 | 98.0% | 2 | 26.8 | 30.7 | 24.1 |
| BullsEye | 4.8 | .52E+06 | 2.01E+08 | 99.3% | 2 | 27.1 | 31.0 | 24.1 |
| Control | 4.8 | 1.52E+06 | 1.38E+08 | 99.3% | 2 | 31.0 | 36.2 | 24.1 |

The Bull's Eye load may be evaluated using MSC from four different donors. Yields from Bull's Eye loaded harvests may be consistently higher than the yields loaded using LCWUS and cultured under identical conditions. The mean cell yield increase using Bull's Eye (n=6) vs. LCWUS (n=4) may be 25%.

Viability of MSC samples from the IC loop taken immediately after performing the Bull's Eye load may be 100%. Viability of MSC from Bull's Eye harvests may be over 98% for all samples. MSC from Bull's Eye harvests may display typical morphology in culture, and all MSC biomarkers measured by flow cytometry may conform to ISCT standards.

Example 8

The same protocol as described above with respect to EXAMPLE 7 may be used to study modifications to the Bulls Eye attachment protocol. The modifications to the Bulls Eye attachment (Bulls Eye II), and to the protocol described above, include eliminating the attachments phases after the circulation rates: 100 ml/min; −50 ml/min; and 25 ml/min. That is, instead of having 7 minute stop conditions as described above, there is no stop condition so that the next circulation rate follows the previous circulation rate. A control, as well as an original Bulls Eye run (Bulls Eye I) may also be performed as a comparison.

The results of this study may be as follows:

TABLE 73

| Load | Time (days) | #Cells Loaded | #Cells Harvested | Viability | Agg (0-5) | 69% Adjusted Doubling Time (Hrs) | Unadjusted Doubling Time (Hrs) | Mean Flask Doubling Time (Hrs) |
|---|---|---|---|---|---|---|---|---|
| BullsEye I | 4.9 | 1.52E+07 | 2.60E+08 | 99.2% | 0 | 25.4 | 28.7 | 26.0 (500 cells/cm2) |
| Control | 4.9 | 1.52E+07 | 1.94E+08 | 97.5% | 1 | 27.9 | 32.0 | 5.5 (345 cells/cm2) |
| BullsEye II | 4.9 | 1.52E+07 | 2.10E+08 | 98.1% | 1 | 27.2 | 31.1 | ? |
| BullsEye II | 4.9 | 1.52E+07 | 2.07E+08 | 98.7% | 1 | 27.3 | 31.2 | ? |

It will be apparent to those skilled in the art that various modifications and variations can be made to the methods and structure of the present invention without departing from its scope. Thus it should be understood that the present invention is not be limited to the specific examples given. Rather, the present invention is intended to cover modifications and variations within the scope of the following claims and their equivalents.

As used herein, "at least one," "one or more," and "and/or" are open-ended expressions that are both conjunctive and disjunctive in operation. For example, each of the expressions "at least one of A, B and C," "at least one of A, B, or C," "one or more of A, B, and C," "one or more of A, B, or C" and "A, B, and/or C" can mean A alone, B alone, C alone, A and B together, A and C together, B and C together, or A, B and C together.

While example embodiments and applications of the present invention have been illustrated and described, it is to be understood that the invention is not limited to the precise configuration and resources described above. Various modifications, changes, and variations apparent to those skilled in the art may be made in the arrangement, operation, and details of the methods and systems of the present invention disclosed herein without departing from the scope of the present invention.

What is claimed is:

1. A method of coating a bioreactor, the method comprising:
    introducing a first fluid into the bioreactor and while introducing the first fluid into the bioreactor:
        circulating a second fluid at a first flow rate through the bioreactor of a cell expansion system, wherein the second fluid comprises a reagent;
        while circulating, maintaining the bioreactor in a first orientation for a first period of time to allow at least a first portion of the reagent to coat the bioreactor;
        after the first period of time, circulating the second fluid at a second flow rate slower than the first flow rate through the bioreactor of the cell expansion system for a second period of time to allow a second portion of the reagent to coat the bioreactor;

wherein introduction of the first fluid promotes coating of the bioreactor by ultrafiltration;
stopping the introduction of the first fluid; and
circulating a third fluid through the bioreactor to remove a portion of the reagent not coated on the bioreactor.

2. The method of claim 1, wherein the circulating the second fluid at the second flow rate is in a direction opposite a direction of the circulating the second fluid at the first flow rate.

3. The method of claim 2, further comprising rotating the bioreactor to a second orientation that is about 180 degrees from the first orientation after the first period of time and before the circulating the second fluid at the second flow rate.

4. The method of claim 3, after the second period of time, circulating the second fluid at a third flow rate slower than the second flow rate through the bioreactor of the cell expansion system for a third period of time to allow a third portion of the reagent to coat the bioreactor.

5. The method of claim 4, wherein the circulating the second fluid at the third flow rate is in the same direction as the direction of the circulating the second fluid at the first flow rate.

6. The method of claim 5, further comprising rotating the bioreactor back to the first orientation after the second period of time and before the circulating the second fluid at the third flow rate.

7. The method of claim 6, after the third period of time, circulating the second fluid at a fourth flow rate slower than the third flow rate through the bioreactor of the cell expansion system for a fourth period of time to allow a fourth portion of the reagent to coat the bioreactor.

8. The method of claim 7, wherein the circulating the second fluid at the fourth flow rate is in the opposite direction as the direction of the circulating the second fluid at the first flow rate.

9. The method of claim 8, further comprising rotating the bioreactor back to the second orientation after the third period of time and before the circulating the second fluid at the fourth flow rate.

10. The method of claim 9, after the fourth period of time, circulating the second fluid at a fifth flow rate slower than the fourth flow rate through the bioreactor of the cell expansion system for a fifth period of time to allow a fifth portion of the reagent to coat the bioreactor.

11. The method of claim 10, wherein the circulating the second fluid at the fifth flow rate is in the same direction as the direction of the circulating the second fluid at the first flow rate.

12. The method of claim 11, further comprising rotating the bioreactor back to the first orientation after the fourth period of time and before the circulating the second fluid at the fifth flow rate.

13. The method of claim 12, after the fifth period of time, circulating the second fluid at a sixth flow rate slower than the fifth flow rate through the bioreactor of the cell expansion system for a sixth period of time to allow a sixth portion of the reagent to coat the bioreactor.

14. The method of claim 13, wherein the circulating the second fluid at the sixth flow rate is in the opposite direction as the direction of the circulating the second fluid at the first flow rate.

15. The method of claim 14, further comprising rotating the bioreactor back to the second orientation after the fifth period of time and before the circulating the second fluid at the sixth flow rate.

16. The method of claim 15, after the sixth period of time, circulating the second fluid at a seventh flow rate slower than the sixth flow rate through the bioreactor of the cell expansion system for a seventh period of time to allow a seventh portion of the reagent to coat the bioreactor.

17. The method of claim 16, wherein the circulating the second fluid at the seventh flow rate is in the same direction as the direction of the circulating the second fluid at the first flow rate.

18. The method of claim 17, further comprising rotating the bioreactor back to the first orientation after the sixth period of time and before the circulating the second fluid at the seventh flow rate.

19. The method of claim 18, wherein the method is completed in less than sixty minutes.

* * * * *